United States Patent
Alleca et al.

(10) Patent No.: US 12,233,275 B2
(45) Date of Patent: Feb. 25, 2025

(54) AUTOMATED EXTERNAL DEFIBRILLATOR AND POWER SUPPLY ADAPTED FOR NON-CLINICAL USE

(71) Applicant: ZOLL Medical Corporation, Chelmsford, MA (US)

(72) Inventors: Kenneth R. Alleca, Billerica, MA (US); Melissa M. Dascoli, Wakefield, MA (US); Timothy F. Stever, Lowell, MA (US); Charles Sawyer, Sudbury, MA (US); Mohamed Abdelaziz, Nashua, NH (US); Christine O'Toole, West Roxbury, MA (US); Elijah White, Wellesley, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 338 days.

(21) Appl. No.: 17/672,066

(22) Filed: Feb. 15, 2022

(65) Prior Publication Data
US 2022/0257961 A1 Aug. 18, 2022

Related U.S. Application Data

(60) Provisional application No. 63/149,895, filed on Feb. 16, 2021.

(51) Int. Cl.
*A61N 1/39* (2006.01)
(52) U.S. Cl.
CPC ......... *A61N 1/3975* (2013.01); *A61N 1/3904* (2017.08); *A61N 1/3925* (2013.01); *A61N 1/3993* (2013.01)

(58) Field of Classification Search
None
See application file for complete search history.

(56) References Cited

U.S. PATENT DOCUMENTS

| | | | |
|---|---|---|---|
| 4,566,457 A * | 1/1986 | Stemple | A61N 1/3931 607/142 |
| 5,611,815 A | 3/1997 | Cole et al. | |
| 5,662,690 A | 9/1997 | Cole et al. | |
| 5,733,310 A | 3/1998 | Lopin et al. | |

(Continued)

*Primary Examiner* — Eric D. Bertram
(74) *Attorney, Agent, or Firm* — The Webb Law Firm

(57) ABSTRACT

Some embodiments of the current disclosure are directed toward defibrillation and defibrillation equipment, and more particularly, an automated external defibrillator (AED) and a non-clinical power adapter therefor. In some embodiments, an AED may include an electrical connector to receive a battery pack, at least one capacitor to store energy, an electrotherapy delivery circuit to deliver the energy externally as electrotherapy, at least one discharge circuit to internally discharge energy stored in the capacitor(s), a non-clinical power adapter to be received by the electrical connector, and at least one processor. The processor(s) may determine whether the non-clinical power adapter is electrically coupled to the electrical connector, determine whether the automated external defibrillator recognizes the non-clinical power adapter, and/or enable power to be supplied to the automated external defibrillator from the non-clinical power adapter if the automated external defibrillator recognizes the non-clinical power adapter.

41 Claims, 24 Drawing Sheets

(56) References Cited

U.S. PATENT DOCUMENTS

| | | |
|---|---|---|
| 5,733,370 A | 3/1998 | Chen et al. |
| 5,836,993 A | 11/1998 | Cole |
| 6,125,298 A | 9/2000 | Olson et al. |
| 6,127,063 A | 10/2000 | Kowalsky et al. |
| 6,438,415 B1 | 8/2002 | Powers |
| 8,179,087 B2* | 5/2012 | Neumiller ............. H01M 10/44 |
| | | 607/60 |
| 8,183,823 B2* | 5/2012 | Neumiller ............ A61N 1/3975 |
| | | 607/60 |
| 9,576,502 B2 | 2/2017 | Griesser et al. |
| 10,143,387 B2 | 12/2018 | Tan et al. |
| 10,300,293 B2 | 5/2019 | Dascoli et al. |
| 2004/0143297 A1* | 7/2004 | Ramsey, III ......... A61N 1/3975 |
| | | 607/5 |
| 2009/0295326 A1 | 12/2009 | Daynes et al. |
| 2010/0198286 A1* | 8/2010 | Neumiller ............ A61N 1/3931 |
| | | 607/5 |
| 2010/0198287 A1* | 8/2010 | Neumiller ................ H02J 7/02 |
| | | 607/5 |
| 2010/0324612 A1 | 12/2010 | Matos |
| 2019/0247672 A1 | 8/2019 | Elghazzawi et al. |

\* cited by examiner

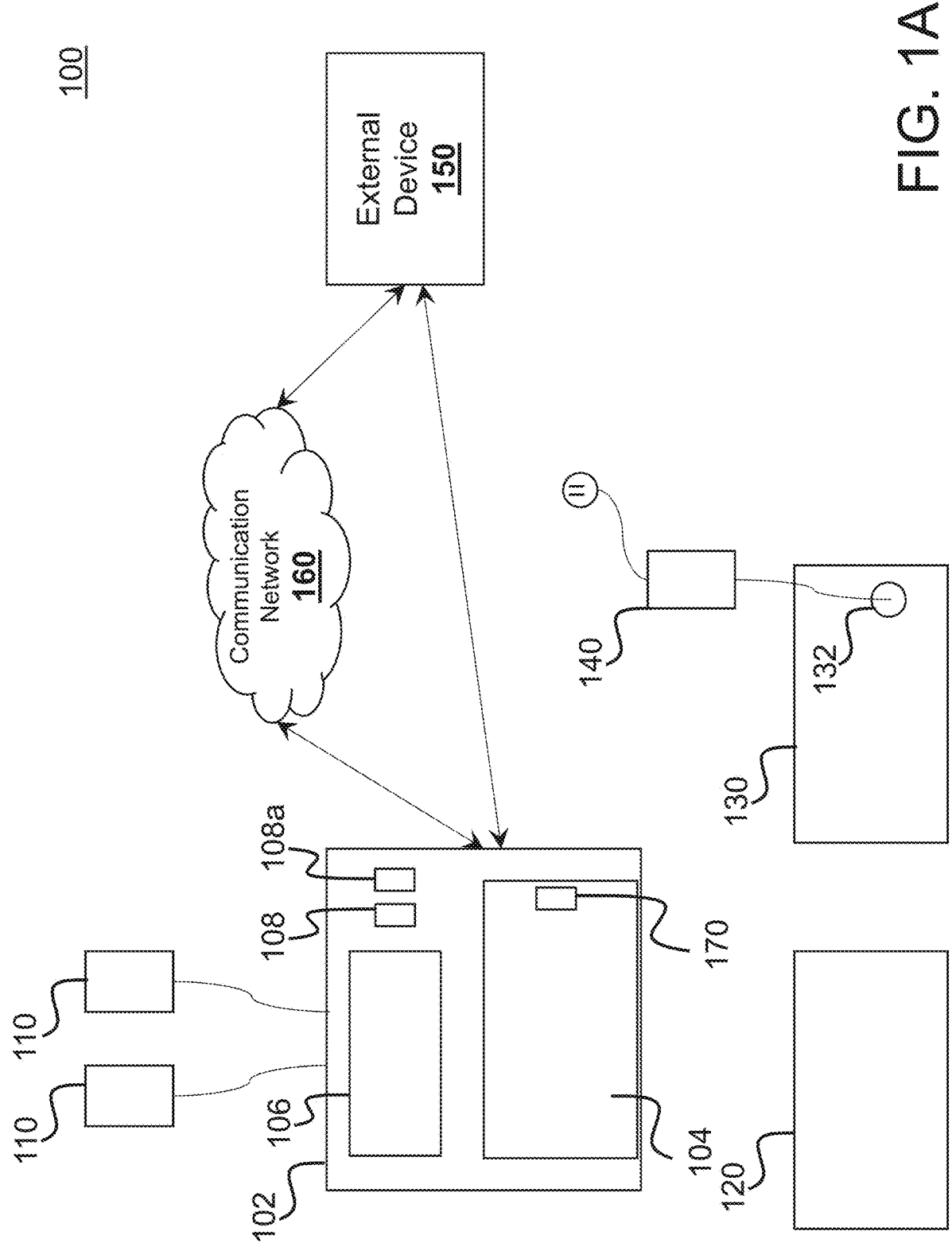

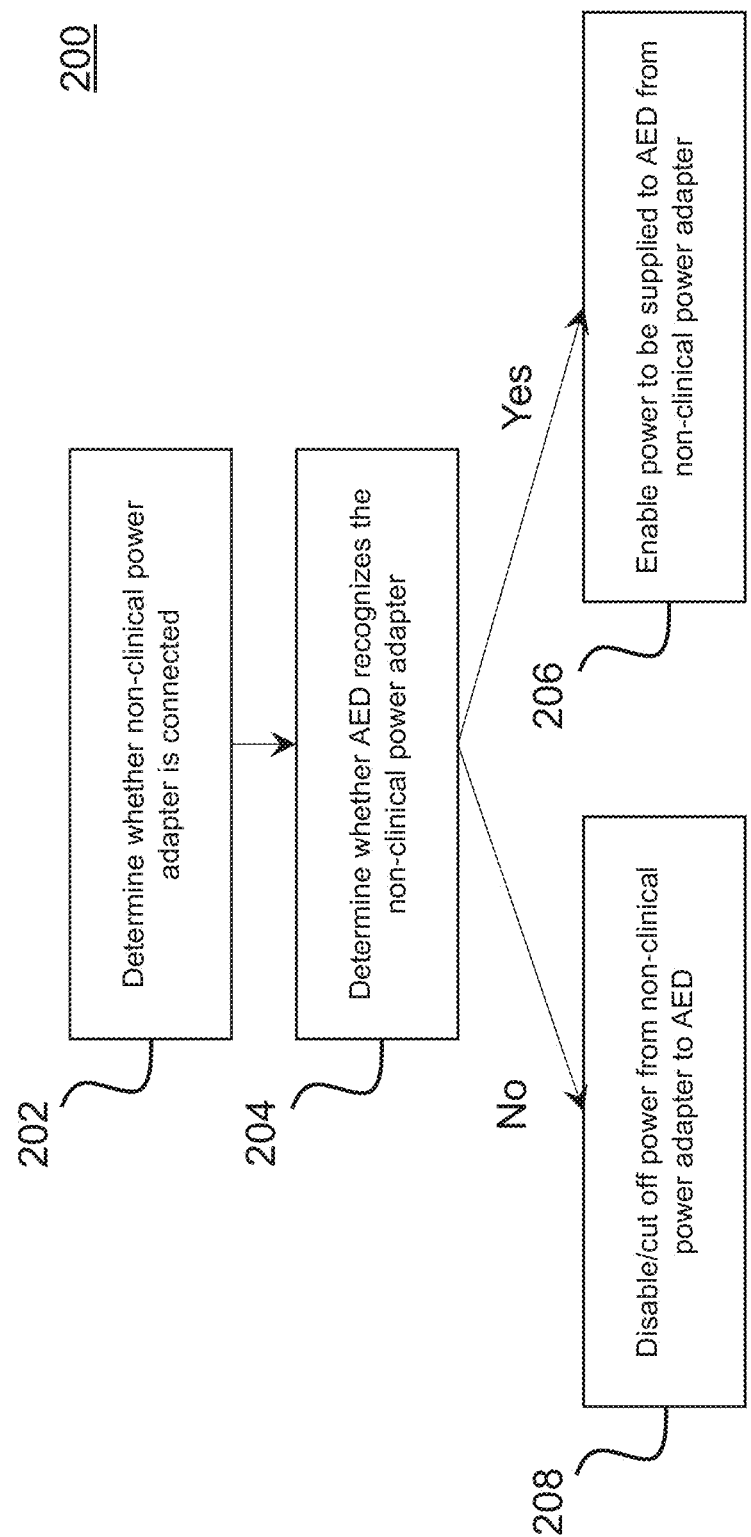

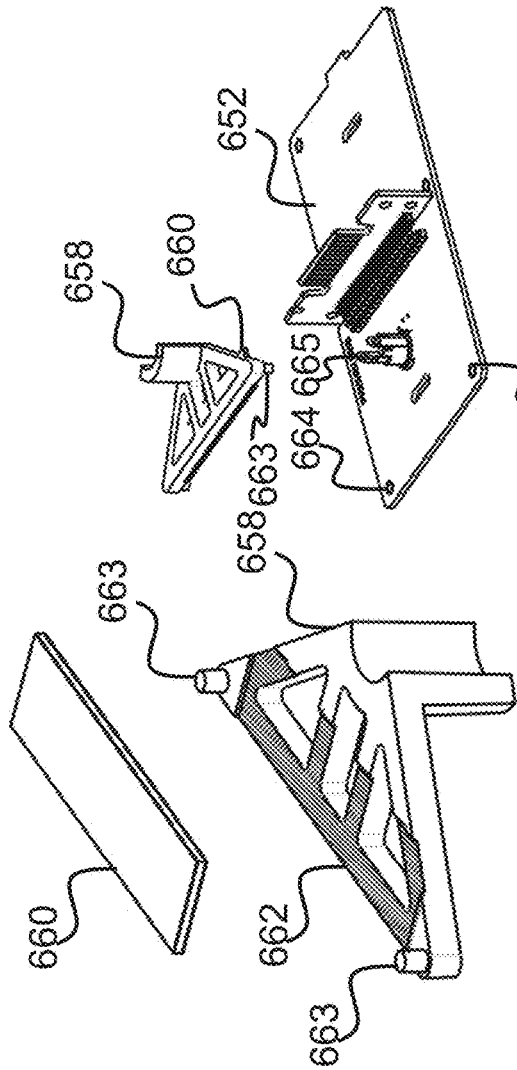
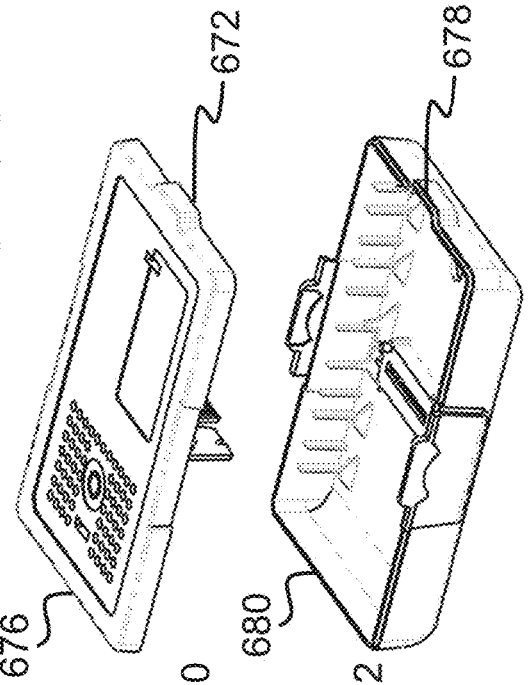
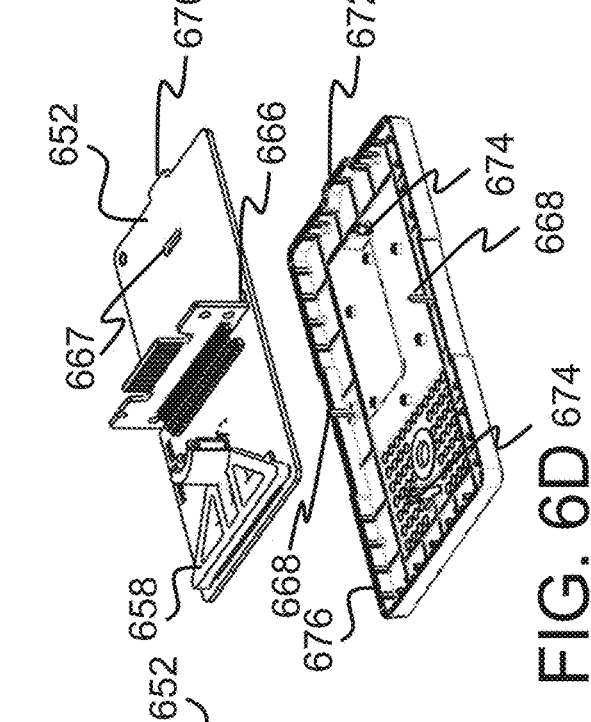
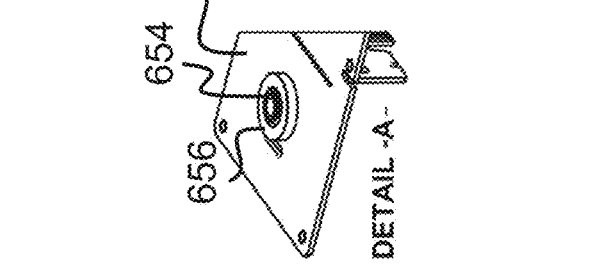

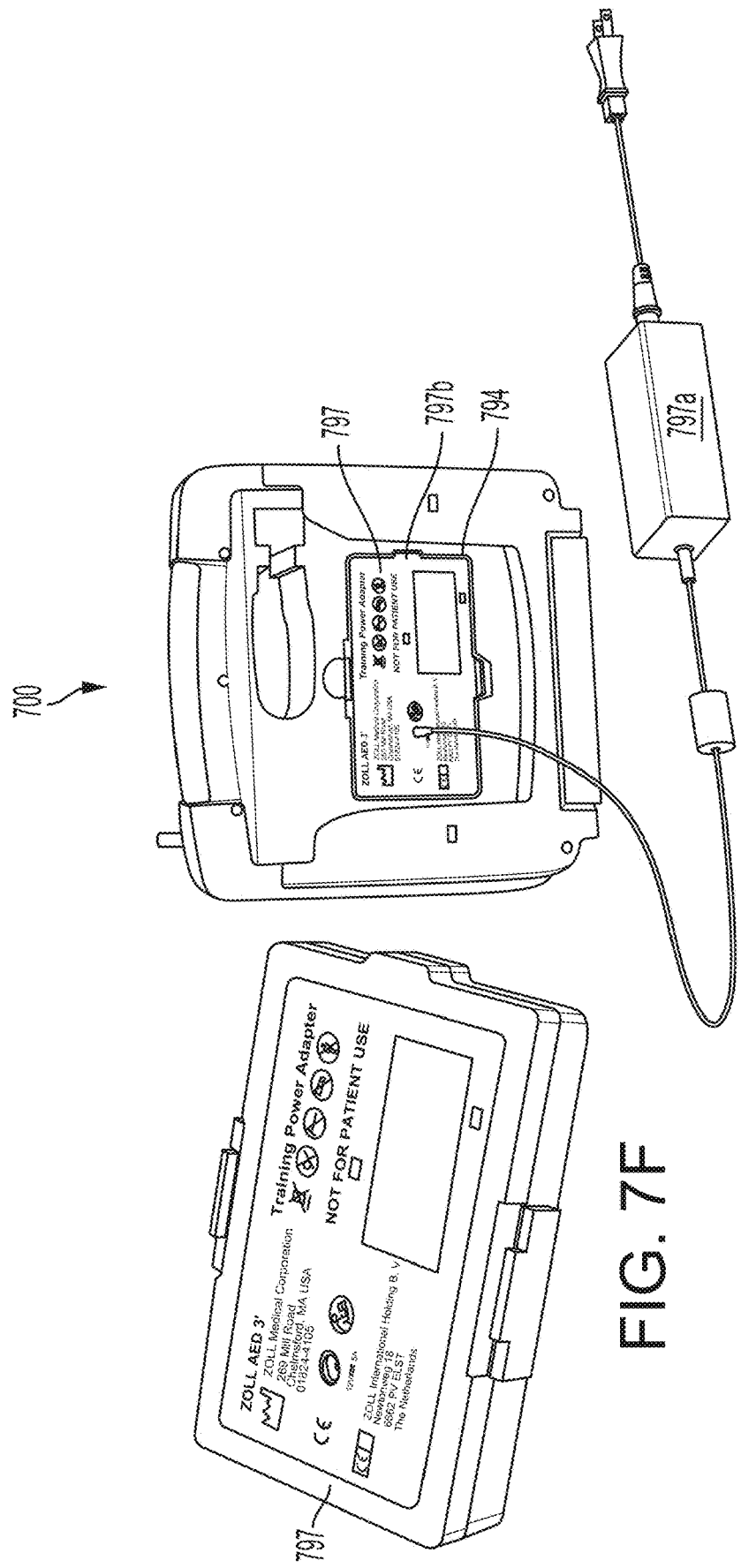

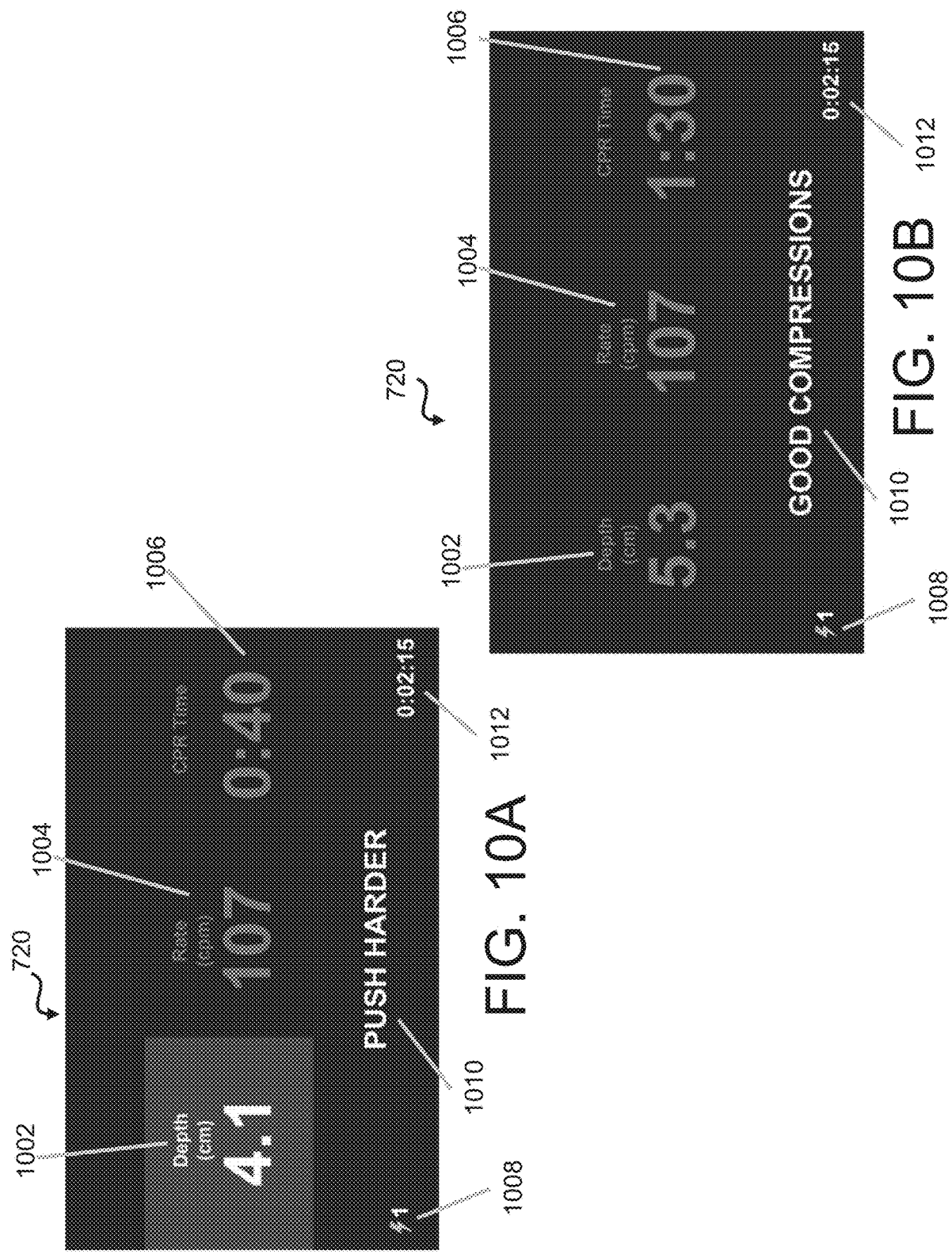

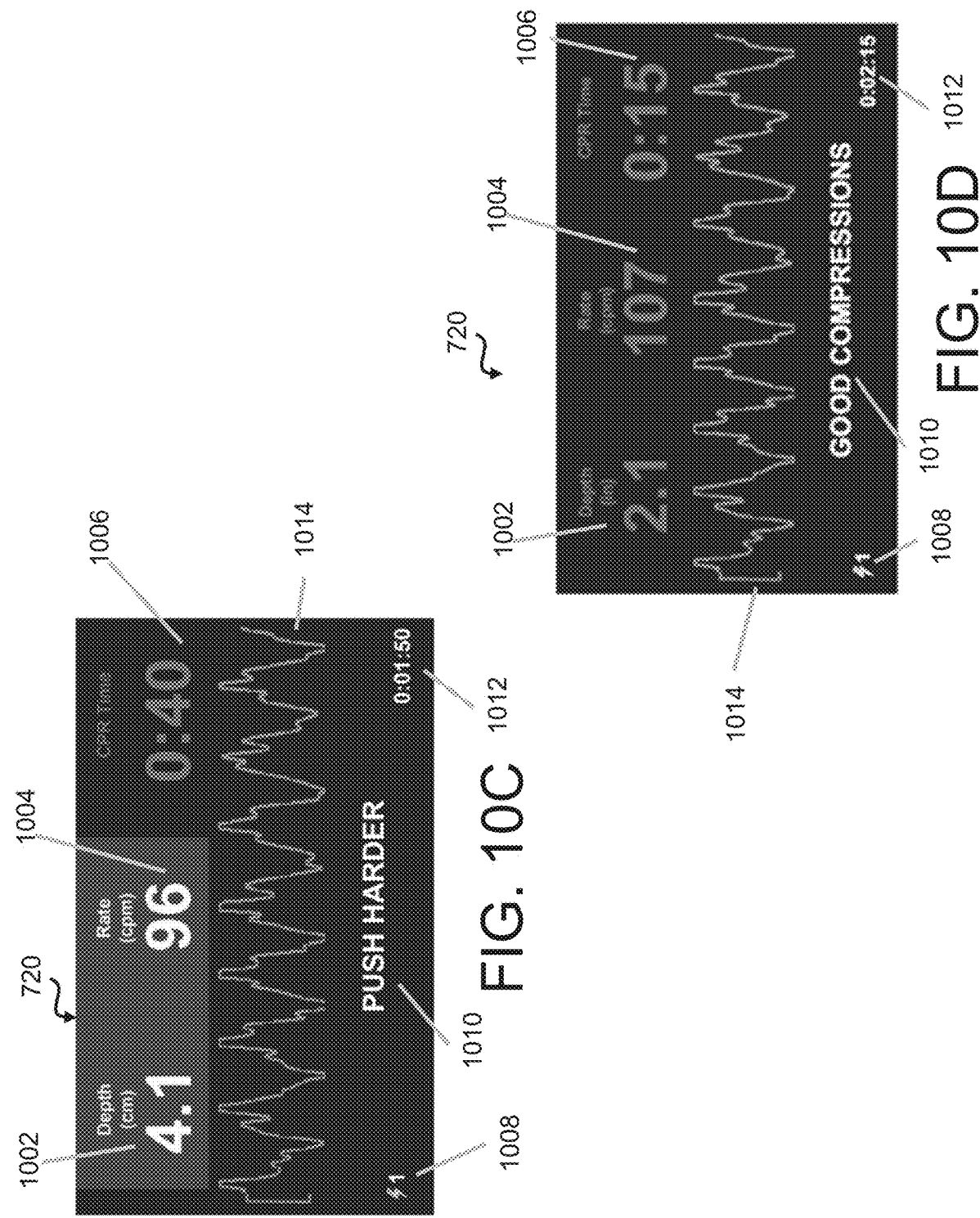

AUTOMATED EXTERNAL DEFIBRILLATOR AND POWER SUPPLY ADAPTED FOR NON-CLINICAL USE

CROSS-REFERENCE TO RELATED APPLICATION

The present application claims the benefit of U.S. Provisional Patent Application No. 63/149,895, filed Feb. 16, 2021, the disclosure of which is hereby incorporated by reference in its entirety.

FIELD OF THE DISCLOSURE

Embodiments of the current disclosure are directed toward defibrillation and defibrillation equipment, and more particularly, an automated external defibrillator and a power supply adapted for non-clinical use.

BACKGROUND OF THE DISCLOSURE

There is a wide variety of electronic and mechanical devices for monitoring and/or treating patients' medical conditions. In some examples, depending on the underlying medical condition being monitored and/or treated, medical devices such as cardiac monitors or defibrillators may be externally connected to the patient. In some cases, physicians may use medical devices alone or in combination with drug therapies to treat conditions such as cardiac arrhythmias.

Such patients can suffer from cardiac arrhythmias which may lead to sudden cardiac arrest. One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim typically has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur in a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. External defibrillators (such as manual defibrillators or publicly accessible automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an external defibrillator, e.g., by providing a therapeutic shock to the heart in an attempt to restore normal rhythm. Example external automated external defibrillators, cardiac monitoring and/or treatment devices include the ZOLL AED Plus® defibrillator available from ZOLL Medical Corporation and the ZOLL AED 3® defibrillator available from ZOLL Medical Corporation.

SUMMARY OF SOME OF THE EMBODIMENTS

Embodiments of the current disclosure include an automated external defibrillator and power adapters associated therewith. In some embodiments, the automated external defibrillator and power adapters associated therewith may include an electrical connector configured to receive a battery pack; at least one capacitor configured to store energy and an electrotherapy delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to: determine whether the non-clinical power adapter is electrically coupled to the electrical connector, determine whether the automated external defibrillator recognizes the non-clinical power adapter, and enable power to be supplied to the automated external defibrillator from the non-clinical power adapter if the automated external defibrillator recognizes the non-clinical power adapter.

In some embodiments, a housing defines a cavity to receive the battery pack, the electrical connector is within the cavity, the non-clinical power adapter is configured to be received in the cavity, and the at least one capacitor and the at least one discharge circuit are within the housing.

In some embodiments, the battery pack comprises a first alignment feature and the cavity comprises a second alignment feature corresponding to the first alignment feature, and the non-clinical power adapter comprises a third alignment feature corresponding to the second alignment feature.

In some embodiments, the first alignment feature and the third alignment feature each comprises a protrusion and the second alignment feature comprises an indentation configured to receive the protrusion.

In some embodiments, the non-clinical power adapter comprises: a power adapter housing comprising a bottom enclosure and a top cover; and a circuit board comprising an input connection configured to receive power from a power supply, at least one voltage regulator, and an output connection configured to connect to the electrical connector.

In some embodiments, the power adapter further comprises: a support bracket to support the circuit board within the power adapter housing; a first adhesive fastener connecting the circuit board to the support bracket; and a second adhesive fastener connecting the circuit board to the top cover.

In some embodiments, the circuit board comprises at least one first alignment feature and the support bracket comprises at least one second alignment feature corresponding to the at least one first alignment feature.

In some embodiments, the at least one first alignment feature comprises a plurality of holes defined by the circuit board and the at least one second alignment feature comprises a plurality of protrusions configured to be received by the plurality of holes.

In some embodiments, the circuit board comprises at least one first alignment feature and the top cover comprises at least one second alignment feature corresponding to the at least one first alignment feature.

In some embodiments, the at least one first alignment feature comprises at least one hole defined by the circuit board and at least one protrusion at an edge of the circuit board, and the at least one second alignment feature comprises at least one snap hook configured to be received by the at least one hole and at least one indentation configured to receive the at least one protrusion.

In some embodiments, the bottom enclosure comprises at least one first alignment feature and the top cover comprises at least one second alignment feature corresponding to the at least one first alignment feature.

In some embodiments, the at least one first alignment feature comprises a first indentation, and the at least one second alignment feature comprises a second indentation configured to align with the first indentation.

In some embodiments, the battery pack comprises a disposable battery pack.

In some embodiments, the power adapter comprises a size and shape corresponding to the battery pack.

In some embodiments, the non-clinical power adapter comprises a first color and the battery pack comprises a second color different than the first color.

In some embodiments, the at least one capacitor comprises at least one high voltage capacitor.

In some embodiments, the at least one high voltage capacitor is configured to store an amount of energy sufficient to deliver a defibrillating shock.

In some embodiments, the amount of energy comprises at least 50 J.

In some embodiments, the amount of energy comprises at least one of up to 50 J, up to 70 J, up to 85 J, up to 100 J, up to 120 J, up to 150 J, or up to 200 J.

In some embodiments, the electrotherapy comprises at least one of 120 J, 150 J, or 200 J in an adult mode or at least one of 50 J, 70 J, or 85 J in a pediatric mode.

In some embodiments, at least one electrode connector is configured to connect at least one electrode to the automated external defibrillator.

In some embodiments, enabling power to be supplied to the automated external defibrillator from the non-clinical power adapter comprises enabling the automated external defibrillator to operate in a non-clinical mode.

In some embodiments, enabling the automated external defibrillator to operate in a non-clinical mode comprises at least one of: disabling delivery of energy externally as electrotherapy, charging the at least one capacitor to a predetermined threshold that is less than a minimum energy setting for clinical use, or discharging the stored energy from the at least one capacitor internally through the at least one discharge circuit.

In some embodiments, discharging the stored energy from the at least one capacitor internally through the at least one discharge circuit comprises discharging the stored energy from the at least one capacitor internally through the at least one discharge circuit in response to a control on an exterior of the automated external defibrillator.

In some embodiments, the control comprises a shock button.

In some embodiments, the predetermined threshold comprises at least one of less than 50 J, less than 20 J, less than 10 J, less than 5 J, less than 2 J, 0.1 J to 5 J, or 0.1 J to 2 J.

In some embodiments, the predetermined threshold comprises less than 10 J.

In some embodiments, the predetermined threshold comprises 2 J.

In some embodiments, a plurality of electrical components other than the at least one capacitor are included, and enabling the automated external defibrillator to operate in a non-clinical mode comprises enabling power to be supplied to the plurality of electrical components from the non-clinical power adapter.

In some embodiments, enabling power to be supplied to the plurality of electrical components comprises operating the plurality of electrical components as the plurality of electrical components operate in a clinical mode.

In some embodiments, the at least one processor is further configured to: disable the power being supplied to the automated external defibrillator from the non-clinical power adapter if the automated external defibrillator does not recognize the non-clinical power adapter.

In some embodiments, a communication line connects the electrical connector and a switching element of the non-clinical power adapter, and an input/output (I/O) line connects the switching element and a voltage regulator of the non-clinical power adapter, disabling the power being supplied to the automated external defibrillator from the non-clinical power adapter comprises communicating with the switching element via the communication line to set the I/O line to a first logical voltage, and enabling power to be supplied to the automated external defibrillator from the non-clinical power adapter comprises communicating with the switching element via the communication line to maintain the I/O line at a second logical voltage.

In some embodiments, the first logical voltage comprises at least one of a low logical voltage, less than 2.5 V, less than 3.3 V, or less than 5 V, and the second logical voltage comprises at least one of a high logical voltage, greater than 2.5 V, greater than 3.3 V, or greater than 5 V.

In some embodiments, the voltage regulator is configured to supply power from the non-clinical power adapter to the automated external defibrillator when the I/O line is set to the second logical voltage and to stop supplying power from the non-clinical power adapter to the automated external defibrillator when the I/O line is set to the first logical voltage.

In some embodiments, the switching element comprises a battery monitor circuit, and the battery monitor circuit is configured to disable the voltage regulator by setting the I/O line to the first logical voltage.

In some embodiments, determining whether the automated external defibrillator recognizes the non-clinical power adapter comprises determining whether the automated external defibrillator is compatible with the non-clinical power adapter.

In some embodiments, determining whether the automated external defibrillator is compatible with the non-clinical power adapter comprises determining whether software of the automated external defibrillator recognizes the non-clinical power adapter;

In some embodiments, determining whether software of the automated external defibrillator recognizes the non-clinical power adapter comprises determining whether a version of the software installed on the automated external defibrillator recognizes the non-clinical power adapter.

In some embodiments, determining whether the automated external defibrillator is compatible with the non-clinical power adapter comprises at least one of: determining whether software of the automated external defibrillator is compatible with the non-clinical power adapter; determining whether hardware of the automated external defibrillator is compatible with the non-clinical power adapter; or any combination thereof.

In some embodiments, determining whether the software of the automated external defibrillator is compatible with the non-clinical power adapter comprises determining whether a version of the software installed on the automated external defibrillator is compatible with the non-clinical power adapter.

In some embodiments, determining whether the hardware of the automated external defibrillator is compatible with the non-clinical power adapter comprises determining whether pins of the electrical connector are compatible with the non-clinical power adapter.

In some embodiments, the non-clinical power adapter comprises a memory storing at least one identifier of the non-clinical power adapter, and determining whether the non-clinical power adapter is electrically coupled to the electrical connector comprises reading the at least one identifier from the memory.

In some embodiments, the memory comprises an electrically erasable programmable read-only memory (EEPROM).

In some embodiments, the non-clinical power adapter is configured to supply power having a first voltage and a first current, and at least one of the first voltage or the first current is different than a second voltage or a second current, respectively, of power supplied by the battery pack.

In some embodiments, the first voltage is 12 V, the first current is at least one of 3 A or 5 A, the second voltage is 12 V, and the second current is 6.5 A.

In some embodiments, determining whether the non-clinical power adapter is electrically coupled to the electrical connector comprises detecting that the at least one of the first voltage or the first current is different than the second voltage or the second current, respectively.

Embodiments of the current disclosure include an automated external defibrillator and power adapters associated therewith. In some embodiments, the automated external defibrillator and power adapters associated therewith may include an electrical connector configured to receive a battery pack; at least one capacitor configured to store energy and an electrical delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to determine whether the non-clinical power adapter is electrically coupled to the electrical connector, and in response to the determination: disable delivery of energy externally as electrotherapy, charge the at least one capacitor to a predetermined threshold that is less than a minimum energy setting for clinical use, and discharge the stored energy from the at least one capacitor internally through the at least one discharge circuit.

In some embodiments, the predetermined threshold comprises at least one of less than 50 J, less than 20 J, less than 10 J, less than 5 J, less than 2 J, 0.1 J to 5 J, or 0.1 J to 2 J.

In some embodiments, a plurality of electrical components other than the at least one capacitor are included, and the at least one processor is further configured to enable power to be supplied to the plurality of electrical components from the non-clinical power adapter.

In some embodiments, discharging the stored energy from the at least one capacitor internally through the at least one discharge circuit comprises discharging the stored energy from the at least one capacitor internally through the at least one discharge circuit in response to a first control on an exterior of the automated external defibrillator.

In some embodiments, the first control comprises a shock button.

In some embodiments, the shock button comprises a light, and the energy stored in the at least one capacitor enables the light to turn on before the button is pressed and the energy stored by the at least one capacitor is discharged through the discharge circuit in response to the shock button being pressed.

In some embodiments, a second control is included, and the at least one processor is further configured to switch from an adult mode to a pediatric mode in response to the second control.

In some embodiments, the second control comprises a child button.

In some embodiments, a display is included on an exterior of the automated external defibrillator, and the at least one processor is further configured to, in response to determining the non-clinical power adapter is electrically coupled to the electrical connector, display a message indicating that the automated external defibrillator is not enabled for clinical use on the display.

In some embodiments, a speaker is included, and the at least one processor is further configured to, in response to determining the non-clinical power adapter is electrically coupled to the electrical connector, play an announcement indicating that the automated external defibrillator is not enabled for clinical use from the speaker.

Embodiments of the current disclosure include an automated external defibrillator and power adapters associated therewith. In some embodiments, the automated external defibrillator and power adapters associated therewith may include an electrical connector configured to receive a battery pack; at least one capacitor configured to store energy and an electrical delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to determine whether the non-clinical power adapter is electrically coupled to the electrical connector, and in response to the determination: maintain a plurality of non-clinical features of the automated external defibrillator, the plurality of non-clinical features comprising at least one of: diagnostic testing of the automated external defibrillator, configurability of the automated external defibrillator, data transfer between the automated external defibrillator and an external device, training operations of the automated external defibrillator, or any combination thereof; and disable delivery of the energy externally as electrotherapy.

In some embodiments, the at least one processor is further configured to: charge the at least one capacitor to a predetermined threshold that is less than a minimum energy setting for clinical use, and discharge the stored energy from the at least one capacitor internally through the at least one discharge circuit.

In some embodiments, the at least one processor is further configured to maintain at least one clinical feature other than delivery of the energy externally as electrotherapy.

In some embodiments, the at least one clinical feature comprises at least one of an electrocardiogram (ECG) or shock analysis feature, a resuscitation prompting feature, a resuscitation feedback feature, or any combination thereof.

In some embodiments, the ECG or shock analysis feature comprises at least one of: detecting a heart rhythm via at least one electrode connected to the automated external defibrillator; detecting an ECG via the at least one electrode;

determining whether the heart rhythm or the ECG is shockable based on analyzing the heart rhythm or the ECG; detecting an electrode type of the at least one electrode; receiving impedance data from the at least one electrode; determining whether the at least one electrode is properly attached based on the impedance data; or any combination thereof.

In some embodiments, a display is included on the exterior of the automated external defibrillator, and the resuscitation prompting feature comprises displaying on the display a graphical user interface comprising at least one prompt for performing at least one of chest compressions or cardiopulmonary resuscitation (CPR).

In some embodiments, a speaker is included, and the resuscitation prompting feature comprises at least one of playing from the speaker at least one announcement for performing the at least one of the chest compressions or the CPR, playing from the speaker a metronome tone for performance of the chest compressions, or any combination thereof.

In some embodiments, the resuscitation feedback feature comprises at least one of: receiving accelerometer data from a chest compression sensor connected to an automated external defibrillator; receiving other sensor data from at least one other sensor connected to the automated external defibrillator; displaying on a display on the exterior of the automated external defibrillator feedback data for at least one of the chest compressions or cardiopulmonary resuscitation (CPR); playing via a speaker at least one announcement for feedback for the at least one of the chest compressions or the CPR; or any combination thereof.

In some embodiments, displaying on the display the feedback data for the at least one of the chest compressions or the CPR comprises at least one of: displaying on the display a graphical user interface comprising at least one prompt for adjusting or maintaining performance of the at least one of chest compressions or the CPR; displaying on the display the graphical user interface comprising a depth indicator of depth of the chest compressions; displaying on the display the graphical user interface comprising an event time indicator of elapsed time of an event during which the at least one of the chest compressions or the CPR is being performed; displaying on the display the graphical user interface comprising a shock indicator of at least one of a number of defibrillating shocks or a number of discharges of the energy stored in the at least one capacitor.

In some embodiments, the training operations of the automated external defibrillator comprise using the at least one clinical feature as the at least one clinical feature operates in a clinical mode while delivery of the energy externally as electrotherapy is disabled.

In some embodiments, the diagnostic testing of the automated external defibrillator comprises at least one of: testing the battery pack; determining whether the battery pack is expired; testing whether sufficient power is being supplied to the automated external defibrillator; testing whether at least one electrode is properly connected to the automated external defibrillator; determining whether the at least one electrode is expired; testing electrocardiogram (ECG) circuitry of the automated external defibrillator; testing the at least one capacitor; testing the discharge circuitry; testing the at least one processor; testing chest compression or cardiopulmonary resuscitation (CPR) feedback circuitry; testing a speaker of the automated external defibrillator or audio circuitry thereof; performing a simulator test; performing other internal diagnostic testing of the automated external defibrillator; or any combination thereof.

In some embodiments, the configurability of the automated external defibrillator comprises at least one of: configuring a language setting; configuring a lay rescuer setting; configuring a breathing check setting; configuring a chest compression feedback setting or a cardiopulmonary resuscitation (CPR) feedback setting; configuring a date setting; configuring a time setting; configuring a number of clinical cases setting; configuring a self-test interval setting; configuring an automated self-test report setting; configuring an audio recording setting; configuring a resuscitation prompting setting; configuring a passcode; configuring a device identifier; configuring an energy level setting for at least one of an adult mode or a pediatric mode; configuring a breath prompting setting; configuring a continue resuscitation prompting setting; configuring a resuscitation prompting interval setting; configuring a start with resuscitation setting; configuring a no-shock period setting; configuring a post-shock period setting; configuring a wireless network setting; or any combination thereof.

In some embodiments, the data transfer between the automated external defibrillator and an external device comprises at least one of: communicating diagnostic testing data based on the diagnostic testing of the automated external defibrillator to the external device; communicating patient data to the external device; communicating clinical event data to the external device; communicating voice data to the external device; communicating audio data to the external device; communicating device history data to the external device; receiving at least one software update from the external device; receiving at least one software upgrade from the external devices; or any combination thereof.

In some embodiments, the data transfer between the automated external defibrillator and an external device comprises at least one of: communicating with the external device via a wireless network; communicating with the external device via a wired network; communicating with the external device via a universal serial bus (USB) port; communicating with the external device via a communication interface; or any combination thereof.

In some embodiments, the external device comprises a computing device hosting a clinical archive.

In some embodiments, the computing device comprises a server.

In some embodiments, a display is included on an exterior of the automated external defibrillator, and the at least one processor is further configured to, in response to determining the non-clinical power adapter is electrically coupled to the electrical connector, display a message indicating that the automated external defibrillator is not enabled for clinical use on the display.

In some embodiments, a speaker is included, and the at least one processor is further configured to, in response to determining the non-clinical power adapter is electrically coupled to the electrical connector, play an announcement indicating that the automated external defibrillator is not enabled for clinical use from the speaker.

In some embodiments, a memory and a communication interface are included, and the at least one processor is further configured to: record at least one of diagnostic testing data based on the diagnostic testing of the automated external defibrillator to the external device, patient data, clinical event data, device history data, voice data, audio data; or any combination thereof in the memory; and in response to determining the non-clinical power adapter is electrically coupled to the electrical connector, communicate the at least one of the diagnostic testing data, patient data, clinical event data, device history data, or any combination thereof to the external device via the communication interface.

Embodiments of the current disclosure include an automated external defibrillator and power adapters associated therewith. In some embodiments, the automated external defibrillator and power adapters associated therewith may include an electrical connector configured to receive a battery pack; at least one capacitor configured to store energy and an electrical delivery circuit configured to deliver the energy externally as electrotherapy to a patient; at least discharge circuit configured to internally discharge energy stored in the at least one capacitor, wherein the internally discharged energy is not provided to the patient; a non-clinical power adapter configured to be received by the electrical connector, the non-clinical power adapter comprising: an input connection configured to receive power from a power supply; a voltage regulator configured to receive power having a voltage range from the input connection and supply power having a voltage within the voltage range to an output connection connected to the electrical connector; and a switching element connected to the voltage regulator via an input/output (I/O) line, the switching element configured to disable power being supplied to the automated external defibrillator from the non-clinical power adapter by setting the I/O line to a first logical voltage, and the switching element configured to enable power to be supplied to the automated external defibrillator from the non-clinical power adapter by maintaining the I/O line at a second logical voltage.

In some embodiments, at least one processor is connected to the switching element via a communication line of the electrical connector, the at least one processor configured to disable power being supplied to the automated external defibrillator from the non-clinical power adapter by communicating with the switching element via the communication line to set the I/O line to the first logical voltage, and the at least one processor configured to enable power to be supplied to the automated external defibrillator from the non-clinical power adapter by communicating with the switching element via the communication line to maintain the I/O line at the second logical voltage.

In some embodiments, the at least one processor is further configured to: determine whether the non-clinical power adapter is electrically coupled to the electrical connector; determine whether the automated external defibrillator recognizes the non-clinical power adapter, and enable power to be supplied to the automated external defibrillator from the non-clinical power adapter if the automated external defibrillator recognizes the non-clinical power.

In some embodiments, the first logical voltage comprises at least one of a low logical voltage, less than 2.5 V, less than 3.3 V, or less than 5 V, and the second logical voltage comprises at least one of a high logical voltage, greater than 2.5 V, greater than 3.3 V, or greater than 5 V.

In some embodiments, the voltage regulator is configured to supply power from the non-clinical power adapter to the automated external defibrillator when the I/O line is set to the second logical voltage and to stop supplying power from the non-clinical power adapter to the automated external defibrillator when the I/O line is set to the first logical voltage.

In some embodiments, the switching element comprises a battery monitor circuit, wherein the battery monitor circuit is configured to disable the voltage regulator by setting the I/O line to the first logical voltage.

In some embodiments, a second voltage regulator is configured to receive power having the voltage range from the input connection and to supply power having a second voltage less than the voltage range to at least one electronic component of the non-clinical power adapter.

In some embodiments, the voltage is 12 V, and the second voltage is 3.3 V.

In some embodiments, the at least one electronic component comprises at least one of a memory, the switching element, or any combination thereof.

In some embodiments, the memory comprises an electrically erasable programmable read-only memory (EEPROM).

In some embodiments, at least one processor is included, the at least one electronic component comprises the memory, the memory stores at least one identifier of the non-clinical power adapter, and the at least one processor is configured to read the identifier from the memory to determine the non-clinical power adapter is electrically coupled to the electrical connector.

In some embodiments, the voltage regulator is configured to supply power having the voltage and a selected current, and wherein at least one of the voltage or the selected current is different than a battery pack voltage or a battery pack current, respectively, of power supplied by the battery pack.

In some embodiments, the voltage is 12 V, the selected current is at least one of 3 A or 5 A, the battery pack voltage is 12 V, and the battery pack current is 6.5 A.

In some embodiments, the power supply comprises a direct current (DC) power supply.

In some embodiments, the power supply comprises a voltage converter configured to convert alternating current (AC) input power to DC output power.

In some embodiments, the battery pack comprises a disposable battery pack.

In some embodiments, the non-clinical power adapter comprises a size and shape corresponding to the battery pack.

In some embodiments, the non-clinical power adapter comprises a first color and wherein the battery pack comprises a second color different than the first color.

In some embodiments, the non-clinical power adapter further comprises: a power adapter housing comprising a bottom enclosure and a top cover; and a circuit board comprising the input connection, the voltage regulator, the switching element, the I/O line, and the output connection.

In some embodiments, the non-clinical power adapter further comprises: a support bracket to support the circuit board within the power adapter housing; a first adhesive fastener connecting the circuit board to the support bracket; and a second adhesive fastener connecting the circuit board to the top cover.

Embodiments of the current disclosure include an automated external defibrillator and power adapters associated therewith. In some embodiments, the automated external defibrillator and power adapters associated therewith may include an electrical connector configured to receive a first power supply; at least one capacitor configured to store energy and an electrotherapy delivery circuit configured to deliver the energy externally as electrotherapy to a patient; at least one discharge circuit configured to internally discharge energy stored in the at least one capacitor, wherein the energy is not provided to the patient when internally discharged; a second power supply; and at least one circuit configured to: charge the at least one capacitor with power from the first power supply; and power a plurality of non-clinical features with the second power supply, the plurality of non-clinical features comprising at least one of: diagnostic testing of the automated external defibrillator, configurability of the automated external defibrillator, data transfer between the automated external defibrillator and an external device, training operations of the automated external defibrillator, or any combination thereof.

In some embodiments, charging the at least one capacitor comprises charging the at least one capacitor to a predetermined threshold that is greater than or equal to a minimum energy setting for clinical use if the automated external defibrillator is in a clinical mode.

In some embodiments, the electrotherapy delivery circuit is configured to deliver the energy externally as the electrotherapy to the patient in response to a control on an exterior of the automated external defibrillator if the automated external defibrillator is in the clinical mode.

In some embodiments, charging the at least one capacitor comprises charging the at least one capacitor to a predetermined threshold that is less than a minimum energy setting for clinical use if the automated external defibrillator is in a non-clinical mode.

In some embodiments, the discharge circuit is configured to internally discharge the energy stored in the at least one capacitor in response to a control on an exterior of the automated external defibrillator if the automated external defibrillator is in the non-clinical mode.

In some embodiments, delivery of the energy externally as the electrotherapy is disabled if the automated external defibrillator is in the non-clinical mode.

In some embodiments, the first power supply comprises a battery pack and wherein the second power supply comprises a non-clinical power adapter.

In some embodiments, the non-clinical power adapter comprises a voltage converter configured to convert alternating current (AC) input power to direct current (DC) output power.

In some embodiments, the first power supply comprises a battery pack and wherein the second power supply comprises a second battery pack.

Further embodiments or aspects are set forth in the following numbered clauses:

Clause 1: An automated external defibrillator, comprising: an electrical connector configured to receive a battery pack; at least one capacitor configured to store energy and an electrotherapy delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to: determine whether the non-clinical power adapter is electrically coupled to the electrical connector, determine whether the automated external defibrillator recognizes the non-clinical power adapter, and enable power to be supplied to the automated external defibrillator from the non-clinical power adapter if the automated external defibrillator recognizes the non-clinical power adapter.

Clause 2: The automated external defibrillator of clause 1, further comprising a housing defining a cavity to receive the battery pack, wherein the electrical connector is within the cavity, wherein the non-clinical power adapter is configured to be received in the cavity, and wherein the at least one capacitor and the at least one discharge circuit are within the housing.

Clause 3: The automated external defibrillator of any preceding clause, wherein the battery pack comprises a first alignment feature and the cavity comprises a second alignment feature corresponding to the first alignment feature, and wherein the non-clinical power adapter comprises a third alignment feature corresponding to the second alignment feature.

Clause 4: The automated external defibrillator of any preceding clause, wherein the first alignment feature and the third alignment feature each comprises a protrusion and wherein the second alignment feature comprises an indentation configured to receive the protrusion.

Clause 5: The automated external defibrillator of any preceding clause, wherein the non-clinical power adapter comprises: a power adapter housing comprising a bottom enclosure and a top cover; and a circuit board comprising an input connection configured to receive power from a power supply, at least one voltage regulator, and an output connection configured to connect to the electrical connector.

Clause 6: The automated external defibrillator of any preceding clause, wherein the power adapter further comprises: a support bracket to support the circuit board within the power adapter housing; a first adhesive fastener connecting the circuit board to the support bracket; and a second adhesive fastener connecting the circuit board to the top cover.

Clause 7: The automated external defibrillator of any preceding clause, wherein the circuit board comprises at least one first alignment feature and the support bracket comprises at least one second alignment feature corresponding to the at least one first alignment feature.

Clause 8: The automated external defibrillator of any preceding clause, wherein the at least one first alignment feature comprises a plurality of holes defined by the circuit board and wherein the at least one second alignment feature comprises a plurality of protrusions configured to be received by the plurality of holes.

Clause 9: The automated external defibrillator of any preceding clause, wherein the circuit board comprises at least one first alignment feature and the top cover comprises at least one second alignment feature corresponding to the at least one first alignment feature.

Clause 10: The automated external defibrillator of any preceding clause, wherein the at least one first alignment feature comprises at least one hole defined by the circuit board and at least one protrusion at an edge of the circuit board, and wherein the at least one second alignment feature comprises at least one snap hook configured to be received by the at least one hole and at least one indentation configured to receive the at least one protrusion.

Clause 11: The automated external defibrillator of any preceding clause, wherein the bottom enclosure comprises at least one first alignment feature and the top cover comprises at least one second alignment feature corresponding to the at least one first alignment feature.

Clause 12: The automated external defibrillator of any preceding clause, wherein the at least one first alignment feature comprises a first indentation, and wherein the at least one second alignment feature comprises a second indentation configured to align with the first indentation.

Clause 13: The automated external defibrillator of any preceding clause, wherein the battery pack comprises a disposable battery pack.

Clause 14: The automated external defibrillator of any preceding clause, wherein the power adapter comprises a size and shape corresponding to the battery pack.

Clause 15: The automated external defibrillator of any preceding clause, wherein the non-clinical power adapter comprises a first color and wherein the battery pack comprises a second color different than the first color.

Clause 16: The automated external defibrillator of any preceding clause, wherein the at least one capacitor comprises at least one high voltage capacitor.

Clause 17: The automated external defibrillator of any preceding clause, wherein the at least one high voltage capacitor is configured to store an amount of energy sufficient to deliver a defibrillating shock.

Clause 18: The automated external defibrillator of any preceding clause, wherein the amount of energy comprises at least 50 J.

Clause 19: The automated external defibrillator of any preceding clause, wherein the amount of energy comprises at least one of up to 50 J, up to 70 J, up to 85 J, up to 100 J, up to 120 J, up to 150 J, or up to 200 J.

Clause 20: The automated external defibrillator of any preceding clause, wherein the electrotherapy comprises at least one of 120 J, 150 J, or 200 J in an adult mode or at least one of 50 J, 70 J, or 85 J in a pediatric mode.

Clause 21: The automated external defibrillator of any preceding clause, further comprising at least one electrode connector configured to connect at least one electrode to the automated external defibrillator.

Clause 22: The automated external defibrillator of any preceding clause, wherein enabling power to be supplied to the automated external defibrillator from the non-clinical power adapter comprises enabling the automated external defibrillator to operate in a non-clinical mode.

Clause 23: The automated external defibrillator of any preceding clause, wherein enabling the automated external defibrillator to operate in a non-clinical mode comprises at least one of: disabling delivery of energy externally as electrotherapy, charging the at least one capacitor to a predetermined threshold that is less than a minimum energy setting for clinical use, or discharging the stored energy from the at least one capacitor internally through the at least one discharge circuit.

Clause 24: The automated external defibrillator of any preceding clause, wherein discharging the stored energy from the at least one capacitor internally through the at least one discharge circuit comprises discharging the stored energy from the at least one capacitor internally through the at least one discharge circuit in response to a control on an exterior of the automated external defibrillator.

Clause 25: The automated external defibrillator of any preceding clause, wherein the control comprises a shock button.

Clause 26: The automated external defibrillator of any preceding clause, wherein the predetermined threshold comprises at least one of less than 50 J, less than 20 J, less than 10 J, less than 5 J, less than 2 J, 0.1 J to 5 J, or 0.1 J to 2 J.

Clause 27: The automated external defibrillator of any preceding clause, wherein the predetermined threshold comprises less than 10 J.

Clause 28: The automated external defibrillator of any preceding clause, wherein the predetermined threshold comprises 2 J.

Clause 29: The automated external defibrillator of any preceding clause, further comprising a plurality of electrical components other than the at least one capacitor, wherein enabling the automated external defibrillator to operate in a non-clinical mode comprises enabling power to be supplied to the plurality of electrical components from the non-clinical power adapter.

Clause 30: The automated external defibrillator of any preceding clause, wherein enabling power to be supplied to the plurality of electrical components comprises operating the plurality of electrical components as the plurality of electrical components operate in a clinical mode.

Clause 31: The automated external defibrillator of any preceding clause, wherein the at least one processor is further configured to: disable the power being supplied to the automated external defibrillator from the non-clinical power adapter if the automated external defibrillator does not recognize the non-clinical power adapter.

Clause 32: The automated external defibrillator of any preceding clause, further comprising a communication line connecting the electrical connector and a switching element of the non-clinical power adapter and an input/output (I/O) line connecting the switching element and a voltage regulator of the non-clinical power adapter, wherein disabling the power being supplied to the automated external defibrillator from the non-clinical power adapter comprises communicating with the switching element via the communication line to set the I/O line to a first logical voltage, and wherein enabling power to be supplied to the automated external defibrillator from the non-clinical power adapter comprises communicating with the switching element via the communication line to maintain the I/O line at a second logical voltage.

Clause 33: The automated external defibrillator of any preceding clause, wherein the first logical voltage comprises at least one of a low logical voltage, less than 2.5 V, less than 3.3 V, or less than 5 V, and wherein the second logical voltage comprises at least one of a high logical voltage, greater than 2.5 V, greater than 3.3 V, or greater than 5 V.

Clause 34: The automated external defibrillator of any preceding clause, wherein the voltage regulator is configured to supply power from the non-clinical power adapter to the automated external defibrillator when the I/O line is set to the second logical voltage and to stop supplying power from the non-clinical power adapter to the automated external defibrillator when the I/O line is set to the first logical voltage.

Clause 35: The automated external defibrillator of any preceding clause, wherein the switching element comprises a battery monitor circuit, wherein the battery monitor circuit is configured to disable the voltage regulator by setting the I/O line to the first logical voltage.

Clause 36: The automated external defibrillator of any preceding clause, wherein determining whether the automated external defibrillator recognizes the non-clinical power adapter comprises determining whether the automated external defibrillator is compatible with the non-clinical power adapter.

Clause 37: The automated external defibrillator of any preceding clause, wherein determining whether the automated external defibrillator is compatible with the non-clinical power adapter comprises determining whether software of the automated external defibrillator recognizes the non-clinical power adapter;

Clause 38: The automated external defibrillator of any preceding clause, wherein determining whether software of the automated external defibrillator recognizes the non-clinical power adapter comprises determining whether a version of the software installed on the automated external defibrillator recognizes the non-clinical power adapter Clause 39: The automated external defibrillator of any preceding clause, wherein determining whether the automated external defibrillator is compatible with the non-clinical power adapter comprises at least one of: determining whether software of the automated external defibrillator is compatible with the non-clinical power adapter; determining whether hardware of the automated external defibrillator is compatible with the non-clinical power adapter; or any combination thereof.

Clause 40: The automated external defibrillator of any preceding clause, wherein determining whether the software of the automated external defibrillator is compatible with the non-clinical power adapter comprises determining whether a version of the software installed on the automated external defibrillator is compatible with the non-clinical power adapter.

Clause 41: The automated external defibrillator of any preceding clause, wherein determining whether the hardware of the automated external defibrillator is compatible with the non-clinical power adapter comprises determining whether pins of the electrical connector are compatible with the non-clinical power adapter.

Clause 42: The automated external defibrillator of any preceding clause, wherein the non-clinical power adapter comprises a memory storing at least one identifier of the non-clinical power adapter, and wherein determining whether the non-clinical power adapter is electrically coupled to the electrical connector comprises reading the at least one identifier from the memory.

Clause 43: The automated external defibrillator of any preceding clause, wherein the memory comprises an electrically erasable programmable read-only memory (EEPROM).

Clause 44: The automated external defibrillator of any preceding clause, wherein the non-clinical power adapter is configured to supply power having a first voltage and a first current, and wherein at least one of the first voltage or the first current is different than a second voltage or a second current, respectively, of power supplied by the battery pack.

Clause 45: The automated external defibrillator of any preceding clause, wherein the first voltage is 12 V and the first current is at least one of 3 A or 5 A, wherein the second voltage is 12 V and the second current is 6.5 A.

Clause 46: The automated external defibrillator of any preceding clause, wherein determining whether the non-clinical power adapter is electrically coupled to the electrical connector comprises detecting that the at least one of the first voltage or the first current is different than the second voltage or the second current, respectively.

Clause 47: An automated external defibrillator, comprising: an electrical connector configured to receive a battery pack; at least one capacitor configured to store energy and an electrical delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to determine whether the non-clinical power adapter is electrically coupled to the electrical connector, and in response to the determination: disable delivery of energy externally as electrotherapy, charge the at least one capacitor to a predetermined threshold that is less than a minimum energy setting for clinical use, and discharge the stored energy from the at least one capacitor internally through the at least one discharge circuit.

Clause 48: The automated external defibrillator of any preceding clause, wherein the predetermined threshold comprises at least one of less than 50 J, less than 20 J, less than 10 J, less than 5 J, less than 2 J, 0.1 J to 5 J, or 0.1 J to 2 J.

Clause 49: The automated external defibrillator of any preceding clause, further comprising a plurality of electrical components other than the at least one capacitor, wherein the at least one processor is further configured to enable power to be supplied to the plurality of electrical components from the non-clinical power adapter.

Clause 50: The automated external defibrillator of any preceding clause, wherein discharging the stored energy from the at least one capacitor internally through the at least one discharge circuit comprises discharging the stored energy from the at least one capacitor internally through the at least one discharge circuit in response to a first control on an exterior of the automated external defibrillator.

Clause 51: The automated external defibrillator of any preceding clause, wherein the first control comprises a shock button.

Clause 52: The automated external defibrillator of any preceding clause, wherein the shock button comprises a light, and wherein the energy stored in the at least one capacitor enables the light to turn on before the button is pressed and the energy stored by the at least one capacitor is discharged through the discharge circuit in response to the shock button being pressed.

Clause 53: The automated external defibrillator of any preceding clause, further comprising a second control, wherein the at least one processor is further configured to switch from an adult mode to a pediatric mode in response to the second control.

Clause 54: The automated external defibrillator of any preceding clause, wherein the second control comprises a child button.

Clause 55: The automated external defibrillator of any preceding clause, further comprising a display on an exterior of the automated external defibrillator, wherein the at least one processor is further configured to, in response to determining the non-clinical power adapter is electrically coupled to the electrical connector, display a message indicating that the automated external defibrillator is not enabled for clinical use on the display.

Clause 56: The automated external defibrillator of any preceding clause, further comprising a speaker, wherein the at least one processor is further configured to, in response to determining the non-clinical power adapter is electrically coupled to the electrical connector, play an announcement indicating that the automated external defibrillator is not enabled for clinical use from the speaker.

Clause 57: An automated external defibrillator, comprising: an electrical connector configured to receive a battery pack; at least one capacitor configured to store energy and an electrical delivery circuit configured to deliver the energy externally as electrotherapy to a patient; at least one discharge circuit configured to internally discharge energy stored in the at least one capacitor, wherein the energy is not provided to the patient when internally discharged; a non-clinical power adapter configured to be received by the electrical connector; and at least one processor configured to determine whether the non-clinical power adapter is electrically coupled to the electrical connector, and in response to the determination: maintain a plurality of non-clinical features of the automated external defibrillator, the plurality of non-clinical features comprising at least one of: diagnostic testing of the automated external defibrillator, configurability of the automated external defibrillator, data transfer between the automated external defibrillator and an external device, training operations of the automated external defibrillator, or any combination thereof; and disable delivery of the energy externally as electrotherapy.

Clause 58: The automated external defibrillator of any preceding clause, wherein the at least one processor is further configured to: charge the at least one capacitor to a predetermined threshold that is less than a minimum energy setting for clinical use, and discharge the stored energy from the at least one capacitor internally through the at least one discharge circuit.

Clause 59: The automated external defibrillator of any preceding clause, wherein the at least one processor is further configured to maintain at least one clinical feature other than delivery of the energy externally as electrotherapy.

Clause 60: The automated external defibrillator of any preceding clause, wherein the at least one clinical feature comprises at least one of an electrocardiogram (ECG) or shock analysis feature, a resuscitation prompting feature, a resuscitation feedback feature, or any combination thereof.

Clause 61: The automated external defibrillator of any preceding clause, wherein the ECG or shock analysis feature comprises at least one of: detecting a heart rhythm via at least one electrode connected to the automated external defibrillator; detecting an ECG via the at least one electrode; determining whether the heart rhythm or the ECG is shockable based on analyzing the heart rhythm or the ECG; detecting an electrode type of the at least one electrode; receiving impedance data from the at least one electrode; determining whether the at least one electrode is properly attached based on the impedance data; or any combination thereof.

Clause 62: The automated external defibrillator of any preceding clause, further comprising a display on the exterior of the automated external defibrillator, wherein the resuscitation prompting feature comprises displaying on the display a graphical user interface comprising at least one prompt for performing at least one of chest compressions or cardiopulmonary resuscitation (CPR).

Clause 63: The automated external defibrillator of any preceding clause, further comprising a speaker, wherein the resuscitation prompting feature comprises at least one of playing from the speaker at least one announcement for performing the at least one of the chest compressions or the CPR, playing from the speaker a metronome tone for performance of the chest compressions, or any combination thereof.

Clause 64: The automated external defibrillator of any preceding clause, wherein the resuscitation feedback feature comprises at least one of: receiving accelerometer data from a chest compression sensor connected to automated external defibrillator; receiving other sensor data from at least one other sensor connected to the automated external defibrillator; displaying on a display on the exterior of the automated external defibrillator feedback data for at least one of the chest compressions or cardiopulmonary resuscitation (CPR); playing via a speaker at least one announcement for feedback for the at least one of the chest compressions or the CPR; or any combination thereof.

Clause 65: The automated external defibrillator of any preceding clause, wherein displaying on the display the feedback data for the at least one of the chest compressions or the CPR comprises at least one of: displaying on the display a graphical user interface comprising at least one prompt for adjusting or maintaining performance of the at least one of chest compressions or the CPR; displaying on the display the graphical user interface comprising a depth indicator of depth of the chest compressions; displaying on the display the graphical user interface comprising an event time indicator of elapsed time of an event during which the at least one of the chest compressions or the CPR is being performed; displaying on the display the graphical user interface comprising a shock indicator of at least one of a number of defibrillating shocks or a number of discharges of the energy stored in the at least one capacitor.

Clause 66: The automated external defibrillator of any preceding clause, wherein the training operations of the automated external defibrillator comprise using the at least one clinical feature as the at least one clinical feature operates in a clinical mode while delivery of the energy externally as electrotherapy is disabled.

Clause 67: The automated external defibrillator of any preceding clause, wherein the diagnostic testing of the automated external defibrillator comprises at least one of: testing the battery pack; determining whether the battery pack is expired; testing whether sufficient power is being supplied to the automated external defibrillator; testing whether at least one electrode is properly connected to the automated external defibrillator; determining whether the at least one electrode is expired; testing electrocardiogram (ECG) circuitry of the automated external defibrillator; testing the at least one capacitor; testing the discharge circuitry; testing the at least one processor; testing chest compression or cardiopulmonary resuscitation (CPR) feedback circuitry; testing a speaker of the automated external defibrillator or audio circuitry thereof; performing a simulator test; performing other internal diagnostic testing of the automated external defibrillator; or any combination thereof.

Clause 68: The automated external defibrillator of any preceding clause, wherein the configurability of the automated external defibrillator comprises at least one of: configuring a language setting; configuring a lay rescuer setting; configuring a breathing check setting; configuring a chest compression feedback setting or a cardiopulmonary resuscitation (CPR) feedback setting; configuring a date setting; configuring a time setting; configuring a number of clinical cases setting; configuring a self-test interval setting; configuring an automated self-test report setting; configuring an audio recording setting; configuring a resuscitation prompting setting; configuring a passcode; configuring a device identifier; configuring an energy level setting for at least one of an adult mode or a pediatric mode; configuring a breath prompting setting; configuring a continue resuscitation prompting setting; configuring a resuscitation prompting interval setting; configuring a start with resuscitation setting; configuring a no-shock period setting; configuring a post-shock period setting; configuring a wireless network setting; or any combination thereof.

Clause 69: The automated external defibrillator of any preceding clause, wherein the data transfer between the automated external defibrillator and an external device comprises at least one of: communicating diagnostic testing data based on the diagnostic testing of the automated external defibrillator to the external device; communicating patient data to the external device; communicating clinical event data to the external device; communicating voice data to the external device; communicating audio data to the external device; communicating device history data to the external device; receiving at least one software update from the external device; receiving at least one software upgrade from the external devices; or any combination thereof.

Clause 70: The automated external defibrillator of any preceding clause, wherein the data transfer between the automated external defibrillator and an external device comprises at least one of: communicating with the external device via a wireless network; communicating with the external device via a wired network; communicating with the external device via a universal serial bus (USB) port;

communicating with the external device via a communication interface; or any combination thereof.

Clause 71: The automated external defibrillator of any preceding clause, wherein the external device comprises a computing device hosting a clinical archive.

Clause 72: The automated external defibrillator of any preceding clause, wherein the computing device comprises a server.

Clause 73: The automated external defibrillator of any preceding clause, further comprising a display on an exterior of the automated external defibrillator, wherein the at least one processor is further configured to, in response to determining the non-clinical power adapter is electrically coupled to the electrical connector, display a message indicating that the automated external defibrillator is not enabled for clinical use on the display.

Clause 74: The automated external defibrillator of any preceding clause, further comprising a speaker, wherein the at least one processor is further configured to, in response to determining the non-clinical power adapter is electrically coupled to the electrical connector, play an announcement indicating that the automated external defibrillator is not enabled for clinical use from the speaker.

Clause 75: The automated external defibrillator of any preceding clause, further comprising a memory and a communication interface, wherein the at least one processor is further configured to: record at least one of diagnostic testing data based on the diagnostic testing of the automated external defibrillator to the external device, patient data, clinical event data, device history data, voice data, audio data; or any combination thereof in the memory; and in response to determining the non-clinical power adapter is electrically coupled to the electrical connector, communicate the at least one of the diagnostic testing data, patient data, clinical event data, device history data, or any combination thereof to the external device via the communication interface.

Clause 76: An automated external defibrillator, comprising: an electrical connector configured to receive a battery pack; at least one capacitor configured to store energy and an electrical delivery circuit configured to deliver the energy externally as electrotherapy to a patient; at least discharge circuit configured to internally discharge energy stored in the at least one capacitor, wherein the internally discharged energy is not provided to the patient; a non-clinical power adapter configured to be received by the electrical connector, the non-clinical power adapter comprising: an input connection configured to receive power from a power supply; a voltage regulator configured to receive power having a voltage range from the input connection and supply power having a voltage within the voltage range to an output connection connected to the electrical connector; and a switching element connected to the voltage regulator via an input/output (I/O) line, the switching element configured to disable power being supplied to the automated external defibrillator from the non-clinical power adapter by setting the I/O line to a first logical voltage, and the switching element configured to enable power to be supplied to the automated external defibrillator from the non-clinical power adapter by maintaining the I/O line at a second logical voltage.

Clause 77: The automated external defibrillator of any preceding clause, further comprising at least one processor connected to the switching element via a communication line of the electrical connector, the at least one processor configured to disable power being supplied to the automated external defibrillator from the non-clinical power adapter by communicating with the switching element via the communication line to set the I/O line to the first logical voltage, and the at least one processor configured to enable power to be supplied to the automated external defibrillator from the non-clinical power adapter by communicating with the switching element via the communication line to maintain the I/O line at the second logical voltage.

Clause 78: The automated external defibrillator of any preceding clause, wherein the at least one processor is further configured to: determine whether the non-clinical power adapter is electrically coupled to the electrical connector, determine whether the automated external defibrillator recognizes the non-clinical power adapter, and enable power to be supplied to the automated external defibrillator from the non-clinical power adapter if the automated external defibrillator recognizes the non-clinical power.

Clause 79: The automated external defibrillator of any preceding clause, wherein the first logical voltage comprises at least one of a low logical voltage, less than 2.5 V, less than 3.3 V, or less than 5 V, and wherein the second logical voltage comprises at least one of a high logical voltage, greater than 2.5 V, greater than 3.3 V, or greater than 5 V.

Clause 80: The automated external defibrillator of any preceding clause, wherein the voltage regulator is configured to supply power from the non-clinical power adapter to the automated external defibrillator when the I/O line is set to the second logical voltage and to stop supplying power from the non-clinical power adapter to the automated external defibrillator when the I/O line is set to the first logical voltage.

Clause 81: The automated external defibrillator of any preceding clause, wherein the switching element comprises a battery monitor circuit, wherein the battery monitor circuit is configured to disable the voltage regulator by setting the I/O line to the first logical voltage.

Clause 82: The automated external defibrillator of any preceding clause, further comprising a second voltage regulator configured to receive power having the voltage range from the input connection and to supply power having a second voltage less than the voltage range to at least one electronic component of the non-clinical power adapter.

Clause 83: The automated external defibrillator of any preceding clause, wherein the voltage is 12 V, and wherein the second voltage is 3.3 V.

Clause 84: The automated external defibrillator of any preceding clause, wherein the at least one electronic component comprises at least one of a memory, the switching element, or any combination thereof.

Clause 85: The automated external defibrillator of any preceding clause, wherein the memory comprises an electrically erasable programmable read-only memory (EEPROM).

Clause 86: The automated external defibrillator of any preceding clause, further comprising at least one processor, wherein the at least one electronic component comprises the memory, wherein the memory stores at least one identifier of the non-clinical power adapter, and wherein the at least one processor is configured to read the identifier from the memory to determine the non-clinical power adapter is electrically coupled to the electrical connector.

Clause 87: The automated external defibrillator of any preceding clause, wherein the voltage regulator is configured to supply power having the voltage and a selected current, and wherein at least one of the voltage or the selected current is different than a battery pack voltage or a battery pack current, respectively, of power supplied by the battery pack.

Clause 88: The automated external defibrillator of any preceding clause, wherein the voltage is 12 V and the selected current is at least one of 3 A or 5 A, wherein the battery pack voltage is 12 V and the battery pack current is 6.5 A.

Clause 89: The automated external defibrillator of any preceding clause, wherein the power supply comprises a direct current (DC) power supply.

Clause 90: The automated external defibrillator of any preceding clause, wherein the power supply comprises a voltage converter configured to convert alternating current (AC) input power to DC output power.

Clause 91: The automated external defibrillator of any preceding clause, wherein the battery pack comprises a disposable battery pack.

Clause 92: The automated external defibrillator of any preceding clause, wherein the non-clinical power adapter comprises a size and shape corresponding to the battery pack.

Clause 93: The automated external defibrillator of any preceding clause, wherein the non-clinical power adapter comprises a first color and wherein the battery pack comprises a second color different than the first color.

Clause 94: The automated external defibrillator of any preceding clause, wherein the non-clinical power adapter further comprises: a power adapter housing comprising a bottom enclosure and a top cover; and a circuit board comprising the input connection, the voltage regulator, the switching element, the I/O line, and the output connection;

Clause 95: The automated external defibrillator of any preceding clause, wherein the non-clinical power adapter further comprises: a support bracket to support the circuit board within the power adapter housing; a first adhesive fastener connecting the circuit board to the support bracket; and a second adhesive fastener connecting the circuit board to the top cover.

Clause 96: An automated external defibrillator, comprising: an electrical connector configured to receive a first power supply; at least one capacitor configured to store energy and an electrotherapy delivery circuit configured to deliver the energy externally as electrotherapy to a patient; at least one discharge circuit configured to internally discharge energy stored in the at least one capacitor, wherein the energy is not provided to the patient when internally discharged; a second power supply; and at least one circuit configured to: charge the at least one capacitor with power from the first power supply; and power a plurality of non-clinical features with the second power supply, the plurality of non-clinical features comprising at least one of: diagnostic testing of the automated external defibrillator, configurability of the automated external defibrillator, data transfer between the automated external defibrillator and an external device, training operations of the automated external defibrillator, or any combination thereof.

Clause 97: The automated external defibrillator of any preceding clause, wherein charging the at least one capacitor comprises charging the at least one capacitor to a predetermined threshold that is greater than or equal to a minimum energy setting for clinical use if the automated external defibrillator is in a clinical mode.

Clause 98: The automated external defibrillator of any preceding clause, wherein the electrotherapy delivery circuit is configured to deliver the energy externally as the electrotherapy to the patient in response to a control on an exterior of the automated external defibrillator if the automated external defibrillator is in the clinical mode.

Clause 99: The automated external defibrillator of any preceding clause, wherein charging the at least one capacitor comprises charging the at least one capacitor to a predetermined threshold that is less than a minimum energy setting for clinical use if the automated external defibrillator is in a non-clinical mode.

Clause 100: The automated external defibrillator of any preceding clause, wherein the discharge circuit is configured to internally discharge the energy stored in the at least one capacitor in response to a control on an exterior of the automated external defibrillator if the automated external defibrillator is in the non-clinical mode.

Clause 101: The automated external defibrillator of any preceding clause, wherein delivery of the energy externally as the electrotherapy is disabled if the automated external defibrillator is in the non-clinical mode.

Clause 102: The automated external defibrillator of any preceding clause, wherein the first power supply comprises a battery pack and wherein the second power supply comprises a non-clinical power adapter.

Clause 103: The automated external defibrillator of any preceding clause, wherein the non-clinical power adapter comprises a voltage converter configured to convert alternating current (AC) input power to direct current (DC) output power.

Clause 104: The automated external defibrillator of any preceding clause, wherein the first power supply comprises a battery pack and wherein the second power supply comprises a second battery pack.

Some embodiments of the current disclosure may include an automated external defibrillator and power adapter associated therewith according to any one and/or another of the embodiments illustrated, described, and/or disclosed herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A-D show example block diagrams of a system for an automated external defibrillator and/or a non-clinical power adapter therefor, according to some embodiments.

FIG. 2 shows an example flowchart of a process for a non-clinical power adapter for an automated external defibrillator, according to some embodiments.

FIGS. 6A-6G show example diagrams of assembly of a non-clinical power adapter for an automated external defibrillator, according to some embodiments.

FIGS. 7A-7I show example diagrams of an automated external defibrillator and/or a non-clinical power adapter therefor ready for use, according to some embodiments.

FIGS. 10A-10D show example screenshots of a graphical user interface for display on an automated external defibrillator, according to some embodiments.

DETAILED DESCRIPTION OF SOME OF THE EMBODIMENTS

Figure 1B:
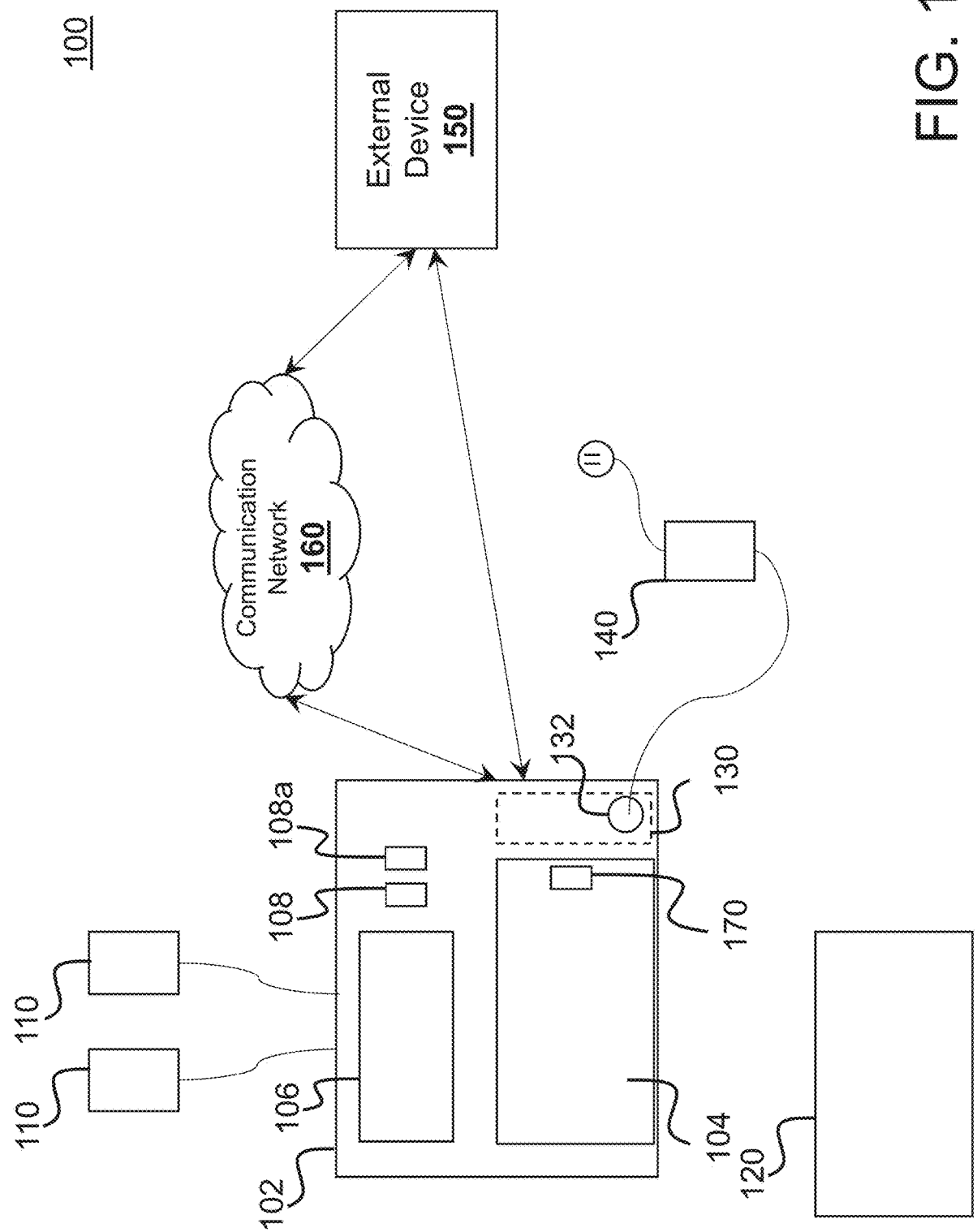

This disclosure relates to an automated external defibrillator (AED) and a non-clinical power adapter therefor. Certain AEDs are powered by battery pack (e.g., a replaceable or rechargeable battery pack). For example, energy from battery pack may be used to charge capacitors and/or to delivery electrotherapy (e.g., a defibrillating shock). Other features (e.g., non-clinical features, such as diagnostic testing, configuring settings, communications, training, and/or the like; other clinical features aside from electrotherapy, such as heart rhythm monitoring, electrocardiogram (ECG) monitoring, and/or the like; any combination thereof; and/or the like) may also consume energy from the battery pack. However, using such other features may deplete the battery pack. For example, using non-clinical features may deplete the battery pack. Additionally or alternatively, it may be desirable to use such other clinical features (e.g., ECG monitoring and/or the like) for other purposes (e.g., training and/or the like), but such use may also deplete the battery pack. As the battery pack is depleted, the battery pack may become unsuitable for use during a clinical event (e.g., may have insufficient energy remaining for charging capacitors and/or delivering electrotherapy), which may be life-threatening if the depletion is unexpected. Further, once the battery pack is depleted, the other features (e.g., non-clinical features, other clinical features, and/or the like) may be unusable until the battery pack is replaced. However, replacing the battery pack may be expensive and/or time consuming.

The AED and the non-clinical power adapter may be configured such that when the non-clinical power adapter is electrically connected to the AED, electrotherapeutic functionality for delivering defibrillation shocks from the AED may be substantially curtailed. Despite inhibiting or otherwise limiting this electrotherapeutic functionality, other non-clinical functions (e.g., configuration, data transfer, self-testing, resuscitation and use training of the AED, etc.) of the AED may remain unaffected without having to use the battery pack for clinical use (separate from the non-clinical power adapter) that provides energy for administering electrotherapeutic defibrillation shocks. Thus, the non-clinical power adapter may provide power to the AED for a user to power on the AED and carry out non-clinical functions, without having to deplete energy from the battery pack that is intended for clinical use.

In various examples, an AED may include an electrical connector configured to receive a battery pack, at least one capacitor configured to store energy, an electrotherapy delivery circuit configured to deliver the energy externally as electrotherapy to a patient, at least one discharge circuit configured to internally discharge energy stored in the capacitor(s), and/or at least one processor. Additionally, a non-clinical power adapter may be configured to be received by the electrical connector of the AED. The processor(s) may be configured to determine whether the non-clinical power adapter is electrically coupled to the electrical connector of the AED and/or to take certain actions based on that determination. Example non-clinical use scenarios when the non-clinical power adapter is electrically coupled to the electrical connected of the AED include, for example, diagnostic testing of the AED, configurability of the AED, data transfer between the AED and an external device, training operations of the AED, any combination thereof, and/or the like.

In some embodiments, an AED may include an electrical connector configured to receive a battery pack, at least one capacitor configured to store energy, an electrotherapy delivery circuit configured to deliver the energy externally as electrotherapy to a patient, at least one discharge circuit configured to internally discharge energy stored in the capacitor(s), and/or at least one processor. Additionally, a non-clinical power adapter may be configured to be received by the electrical connector. The processor(s) may be configured to determine whether the non-clinical power adapter is electrically coupled to the electrical connector, determine whether the AED recognizes the non-clinical power adapter, and enable power to be supplied to the AED from the non-clinical power adapter if the AED recognizes the non-clinical power adapter. Additionally or alternatively, the processor(s) may disable the power being supplied to the AED from the non-clinical power adapter if the AED does not recognize the non-clinical power adapter.

For example, in such embodiments, the AED may detect that the non-clinical power adapter is connected and either disable power from the non-clinical power adapter if the non-clinical power adapter is not recognized or enable power from the non-clinical power adapter if the non-clinical power adapter is recognized (e.g., to power at least a subset of the features of the AED). For the purpose of illustration, the AED may disable power from the non-clinical power adapter if the non-clinical power adapter is not recognized to prevent a user from inadvertently attempting to use the AED for a clinical event while the non-clinical power adapter is connected, for example, to prevent damage to the AED from the unrecognized non-clinical power adapter, and/or the like. Additionally or alternatively, the AED may enable power from the non-clinical power adapter, for example, to power at least a subset of the features of the AED, such as non-clinical features and/or the like without depleting the battery pack.

In some embodiments, an AED may include an electrical connector configured to receive a battery pack, at least one capacitor configured to store energy, an electrotherapy delivery circuit configured to deliver the energy externally as electrotherapy to a patient, at least one discharge circuit configured to internally discharge energy stored in the capacitor(s), and/or at least one processor. Additionally, a non-clinical power adapter may be configured to be received by the electrical connector. The processor(s) may be configured to determine whether the non-clinical power adapter is electrically coupled to the electrical connector. Additionally or alternatively, in response to that determination that the non-clinical power adapter is electrically coupled to the electrical connector, the processor(s) may be configured to disable delivery of energy externally as electrotherapy, charge the capacitor(s) to a predetermined threshold that is less than a minimum energy setting for clinical use, and/or discharge the stored energy from the capacitor(s) internally through the discharge circuit(s).

For example, in such embodiments, the AED may limit the charging of the capacitor(s) when the non-clinical power adapter is connected, may prevent defibrillating electrotherapy when the non-clinical power adapter is connected, and/or may internally discharge the limited amount of energy stored in the capacitor(s). As such, the risk of inadvertently delivering energy externally as electrotherapy may be reduced (e.g., eliminated and/or the like) when the non-clinical power adapter is connected. For the purpose of illustration, prevention of such inadvertent delivering energy externally may be desirable when the AED is being used for non-clinical purposes, such as diagnostic testing, configurability (e.g., configuring settings), data transfer (e.g., communication with an external device), training, any combination thereof, and/or the like. Additionally, limiting the charging of the capacitor(s) may reduce wasting of energy when the AED is being used for non-clinical purposes.

In some embodiments, an AED may include an electrical connector configured to receive a battery pack, at least one capacitor configured to store energy, an electrotherapy delivery circuit configured to deliver the energy externally as electrotherapy to a patient, at least one discharge circuit configured to internally discharge energy stored in the capacitor(s), and/or at least one processor. Additionally, a non-clinical power adapter may be configured to be received by the electrical connector. The processor(s) may be configured to determine whether the non-clinical power adapter is electrically coupled to the electrical connector. Additionally or alternatively, in response to that determination that the non-clinical power adapter is electrically coupled to the electrical connector, the processor(s) may be configured to maintain a plurality of non-clinical features of the AED and/or disable delivery of the energy externally as electrotherapy. For example, the plurality of non-clinical features may include at least one of diagnostic testing of the AED, configurability of the AED, data transfer between the AED and an external device, training operations of the AED, any combination thereof, and/or the like.

For example, in such embodiments, the AED may allow for the use of the non-clinical features without having to use the battery pack for such features, which would otherwise lead to undesirable depletion of the battery pack. Additionally, when the non-clinical power adapter is connected and such non-clinical features are being used, the risk of inadvertently attempting to use the AED to deliver electrotherapeutic energy may be reduced (e.g., eliminated).

In some embodiments, an AED may include an electrical connector configured to receive a battery pack, at least one capacitor configured to store energy, an electrotherapy delivery circuit configured to deliver the energy externally as electrotherapy to a patient, and/or at least one discharge circuit configured to internally discharge energy stored in the capacitor(s). Additionally, a non-clinical power adapter may be configured to be received by the electrical connector. The non-clinical power adapter may include an input connection configured to receive power from a power supply, a voltage regulator configured to receive power having a voltage range from the input connection and supply power having a voltage within the voltage range to an output connection connected to the electrical connector, and a switching element connected to the voltage regulator via an input/output (I/O) line. For example, the switching element may be configured to disable power being supplied to the AED from the non-clinical power adapter by setting the I/O line to a first logical voltage and/or to enable power to be supplied to the AED from the non-clinical power adapter by maintaining the I/O line at a second logical voltage.

For example, in such embodiments, the switching element may either enable power to be supplied from the non-clinical power adapter to the AED (e.g., if the non-clinical power adapter is recognized by the AED and/or if the non-clinical power adapter is compatible with the AED) or disable power from being supplied from the non-clinical power adapter to the AED (e.g., if the non-clinical power adapter is not recognized by the AED and/or if the non-clinical power adapter is not compatible with the AED). For the purpose of illustration, the switching element may disable power from the non-clinical power adapter if the non-clinical power adapter based on receiving a communication (e.g., command and/or the like) from at least one processor of the AED. As such, the switching element may prevent damage to the AED (e.g., if the non-clinical power adapter is unrecognized, incompatible, and/or the like), prevent a user from inadvertently attempting to use the AED for a clinical event while the non-clinical power adapter is connected, and/or the like. Additionally or alternatively, the switching element may enable power from the non-clinical power adapter (e.g., to power at least a subset of the features of the AED, such as non-clinical features and/or the like) without having to use the battery pack intended for clinical use, leading to depletion of that battery pack.

In some embodiments, an AED may include an electrical connector configured to receive a first power supply, at least one capacitor configured to store energy, an electrotherapy delivery circuit configured to deliver the energy externally as electrotherapy to a patient, at least one discharge circuit configured to internally discharge energy stored in the at least one capacitor, a second power supply, and/or at least one circuit. For example, the circuit(s) may charge the at least one capacitor with power from the first power supply. Additionally or alternatively, the circuit(s) may power a plurality of non-clinical features with the second power supply. For example, the non-clinical features may include at least one of diagnostic testing of the AED, configurability of the AED, data transfer between the AED and an external device, training operations of the AED, any combination thereof, and/or the like.

For example, in such embodiments, the AED may power the non-clinical features with a second power supply (e.g., a second battery pack, a power adapter connected to a wall outlet, and/or the like) without depleting the energy of a first power supply (e.g., a disposable or rechargeable battery pack intended for electrotherapeutic clinical use). For the purpose of illustration, the second power supply may have sufficient (e.g., abundant and/or the like) energy to power the non-clinical features. For example, if the second power supply includes a power adapter connected to a wall outlet, the amount of energy available may be practically limitless (e.g., unless there is an outage in a power grid supplying electricity to the wall outlet). Additionally, since the power for the non-clinical features may be supplied by the second power supply, the energy of the first (separate) power supply may be preserved for clinical use. For the purpose of illustration, the first power supply (e.g., a battery pack and/or the like) pack may retain sufficient energy for use during a clinical event (e.g., have sufficient energy remaining for charging capacitors and/or delivering electrotherapy), which may prevent life-threatening situations that may arise if a power supply is unexpectedly or otherwise undesirably depleted.

Referring to FIGS. 1A-D, FIGS. 1A-D show example block diagrams of a system 100 in which the AEDs and/or non-clinical power adapters therefor, as described herein, may be implemented. As shown in FIGS. 1A-D, system 100 may include AED 102, cavity 104, display 106, control 108, second control 108a, electrodes 110, battery pack 120, non-clinical power adapter 130, second battery pack 130a, input connection 132, power supply 140, external device 150, communication network 160, electrical connector 170, second electrical connector 170a, charging circuit 172, capacitor(s) 174, electrotherapy delivery circuit 176, discharge circuit 178, electrode connector 180, processor 182, other electrical components 184, and/or the like.

AED 102 may include one or more devices capable of receiving information from and/or communicating information to external device 150 (e.g., directly, indirectly via communication network 160, and/or the like). For example, AED 102 may include at least one computing device, such as a processor, a communication interface, a portable and/or handheld device (e.g., a computer and/or the like), and/or other like devices, as described herein. In some embodiments, AED 102 may include at least one capacitor 174, which may be configured to store energy. Additionally or alternatively, AED 102 may include electrotherapy delivery circuit 176, which may be configured to deliver the energy (e.g., energy stored by capacitor(s) 174) externally as electrotherapy to a patient. In some embodiments, AED 102 may include at least one discharge circuit 178, which may be configured to internally discharge energy stored in the at least one capacitor (e.g., the energy may not be provided to the patient when internally discharged by discharge circuit 178). For example, discharge circuit 178 may include at least one resistive element (e.g., at least one resistor, a plurality of resistors, a bank of resistors, any combination thereof and/or the like) configured to discharge energy (e.g., convert electrical energy into heat and/or the like). In some embodiments, AED 102 may include at least one processor 182.

In some embodiments, AED 102 may include electrical connector 170, which may be configured to receive battery pack 120 and/or non-clinical power adapter 130. Additionally or alternatively, a housing of AED 102 may define a cavity 104 configured to receive battery pack 120 and/or non-clinical power adapter 130, and/or electrical connector 170 may be disposed within cavity 104 and configured to connect to battery pack 120 and/or non-clinical power adapter 130 when battery pack 120 and/or non-clinical power adapter 130, respectively, is received by (e.g., inserted into) cavity 104. In some embodiments, AED 102 may receive (e.g., via electrical connector 170) power from battery pack 120 and/or non-clinical power adapter 130. Additionally or alternatively, charging circuit 172 may charge capacitor(s) 174 based on (e.g., using) the power received by AED 102 (e.g., electrical connector 170 thereof). In some embodiments, charging circuit 172, capacitor(s) 174, electrotherapy delivery circuit 176, discharge circuit 178, electrode connector 180, processor 182, and/or other electrical components 184 may be included (e.g., completely, partially, and/or the like) within the housing of AED 102.

In some embodiments, AED 102 may include display 106, at least one control 108 (e.g., a button, a switch, and/or the like), any combination thereof, and/or the like. Additionally or alternatively, AED 102 may include at least one other electrical component 184 (e.g., other than capacitor(s) 174). In some embodiments, other electrical component(s) 184 may include at least one of display 106, control 108, electrical connector 170, charging circuit 172, electrotherapy delivery circuit 176, discharge circuit 178, electrode connector 180, and/or processor 182.

In some embodiments, AED 102 may include electrode connector 180. For example, electrode connector 180 may be configured to connect at least one electrode 110 to AED 102. In some non-limiting embodiments, electrotherapy delivery circuit 176 may be configured to deliver energy (e.g., from capacitor(s) 174) via electrode connector 180 to electrode(s) 110, which may deliver the energy externally as electrotherapy to a patient, as described herein.

In some embodiments, capacitor(s) 174 may include at least one high voltage capacitor. For example, the high voltage capacitor(s) may be configured to store an amount of energy sufficient to deliver a defibrillating shock (e.g., a sufficiently high voltage to store such an amount of energy). For the purpose of illustration, the amount of energy may include at least 50 J. Additionally or alternatively, the amount of energy may include at least one of the following: up to 50 J, up to 70 J, up to 85 J, up to 100 J, up to 120 J, up to 150 J, up to 200 J, and/or the like. For example, the electrotherapy (e.g., a defibrillating shock) may include at least one of 120 J, 150 J, or 200 J in an adult mode or at least one of 50 J, 70 J, or 85 J in a pediatric mode. For the purpose of illustration, in adult mode, a first defibrillating shock may be 120 J, a second defibrillating shock may be 150 J, and a third defibrillating shock may be 200 J. Additionally or alternatively, in a pediatric mode, a first defibrillating shock may be 50 J, a second defibrillating shock may be 70 J, and a third defibrillating shock may be 85 J. It can be appreciated that these energy levels for adult and/or pediatric mode may be default energies, and may be pre-configured to different energy levels for each of the successive defibrillating shocks.

Battery pack 120 may be configured to be received by electrical connector 170. For example, battery pack 120 may include a battery pack electrical connector configured to connect (e.g., electrically couple and/or the like) to electrical connector 170. In some embodiments, battery pack 120 may include at least one battery configured to store energy. In some embodiments, battery pack 120 may include a memory (e.g., a read-only memory (ROM), an electrically erasable programmable read-only memory (EEPROM), a flash memory, and/or the like) storing at least one identifier of battery pack 120 (e.g., model number, serial number, any combination thereof, and/or the like). Additionally or alternatively, the memory may include battery data associated with battery pack 120 (e.g., expiration date, capacity, voltage rating, current rating, any combination thereof, and/or the like).

In some embodiments, battery pack 120 may include a disposable (e.g., single use and/or the like) battery pack. Additionally or alternatively, battery pack 120 may include a rechargeable (e.g., multiple use and/or the like) battery pack.

Non-clinical power adapter 130 may be configured to be received by electrical connector 170. For example, non-clinical power adapter 130 may include an output connection configured to connect (e.g., electrically couple and/or the like) to electrical connector 170. In some embodiments, non-clinical power adapter 130 may include a memory (e.g., a read-only memory (ROM), an electrically erasable programmable read-only memory (EEPROM), a flash memory, and/or the like) storing at least one identifier of non-clinical power adapter 130 (e.g., model number, serial number, any combination thereof, and/or the like). Additionally or alternatively, the memory may include additional data associated with non-clinical power adapter 130 (e.g., expiration date, capacity, voltage rating, current rating, any combination thereof, and/or the like).

In some embodiments, non-clinical power adapter 130 may include a size and/or shape corresponding to the size and/or shape of battery pack 120. For example, non-clinical power adapter 130 may have substantially the same size and/or substantially the same shape as battery pack 120 (e.g., the size and/or shape of non-clinical power adapter 130 may allow for non-clinical power adapter 130 to be received in the cavity 104, which may be configured to receive battery pack 120). In some embodiments, non-clinical power adapter 130 may include a first color and battery pack 120 may include a second color different than the first color (e.g., to prevent confusion between non-clinical power adapter 130 and battery pack 120).

In some embodiments, non-clinical power adapter 130 may include input connection 132 configured to receive power from power supply 140. Additionally or alternatively, non-clinical power adapter 130 may include at least one voltage regulator, at least one switching element (e.g., to control at least one of the voltage regulator(s)), and/or the like, as described herein. For example, a voltage regulator of non-clinical power adapter 130 may be configured to receive power having a voltage range from input connection 132 and/or to supply power having a voltage within the voltage range to an output connection connected to electrical connector 170, as described herein. Additionally or alternatively, a switching element may be connected to the voltage regulator (e.g., via an I/O line). The switching element may be configured to disable power being supplied to AED 102 from non-clinical power adapter 130 (e.g., by setting the I/O line to a first logical voltage) and/or to enable power to be supplied to AED 102 from non-clinical power adapter 130 (e.g., by maintaining the I/O line at a second logical voltage), as described herein.

In some embodiments, processor 182 of AED 102 may determine whether non-clinical power adapter 130 is electrically coupled to electrical connector 170, as described herein. Additionally or alternatively, processor 182 may determine whether AED 102 recognizes non-clinical power adapter 130, as described herein. In some embodiments, processor 182 may enable power to be supplied to AED 102 from the non-clinical power adapter 130 if AED 102 recognizes non-clinical power adapter 130, as described herein. Additionally or alternatively, processor 182 may disable the power being supplied to AED 102 from the non-clinical power adapter if AED 102 does not recognize non-clinical power adapter 130, as described herein.

In some embodiments, processor 182 of AED 102 may determine whether non-clinical power adapter 130 is electrically coupled to electrical connector 170, as described herein. Additionally or alternatively, in response to that determination, processor 182 may disable delivery of energy externally as electrotherapy (e.g., disable electrotherapy delivery circuit 176 and/or the like), charge capacitor(s) 174 to a predetermined threshold that is less than a minimum energy setting for clinical use, and/or discharge the stored energy from capacitor(s) 174 internally through discharge circuit 178, as described herein.

In some embodiments, processor 182 of AED 102 may determine whether non-clinical power adapter 130 is electrically coupled to electrical connector 170, as described herein. Additionally or alternatively, in response to that determination, processor 182 may maintain a plurality of non-clinical features of AED 102 and/or disable delivery of energy externally as electrotherapy (e.g., disable electrotherapy delivery circuit 176 and/or the like), as described herein. For example, the non-clinical features may include at least one of: diagnostic testing of the AED, configurability of the AED, data transfer between the AED and an external device, training operations of the AED, any combination thereof, and/or the like, as described herein.

Figure 1C:
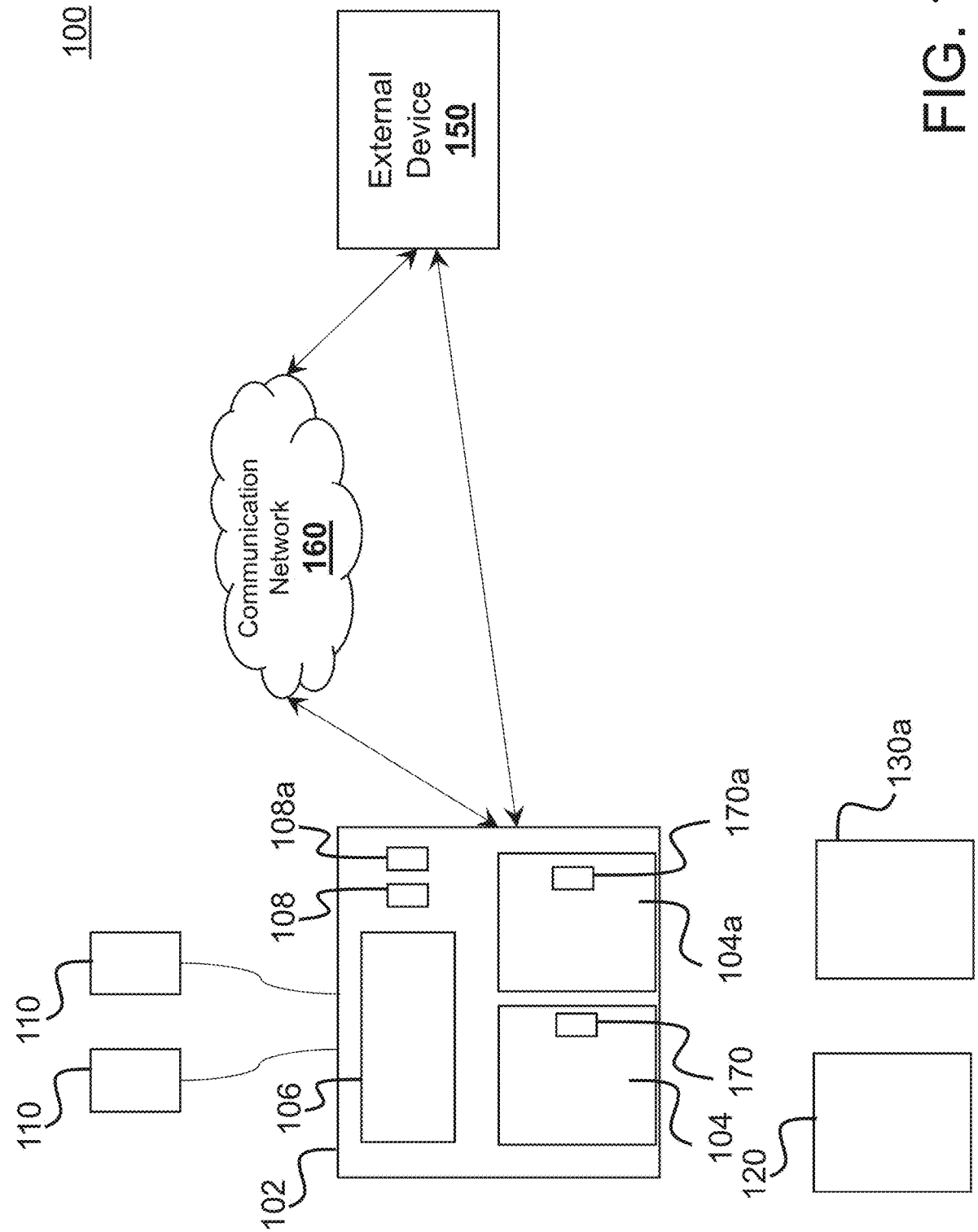
Figure 1D:
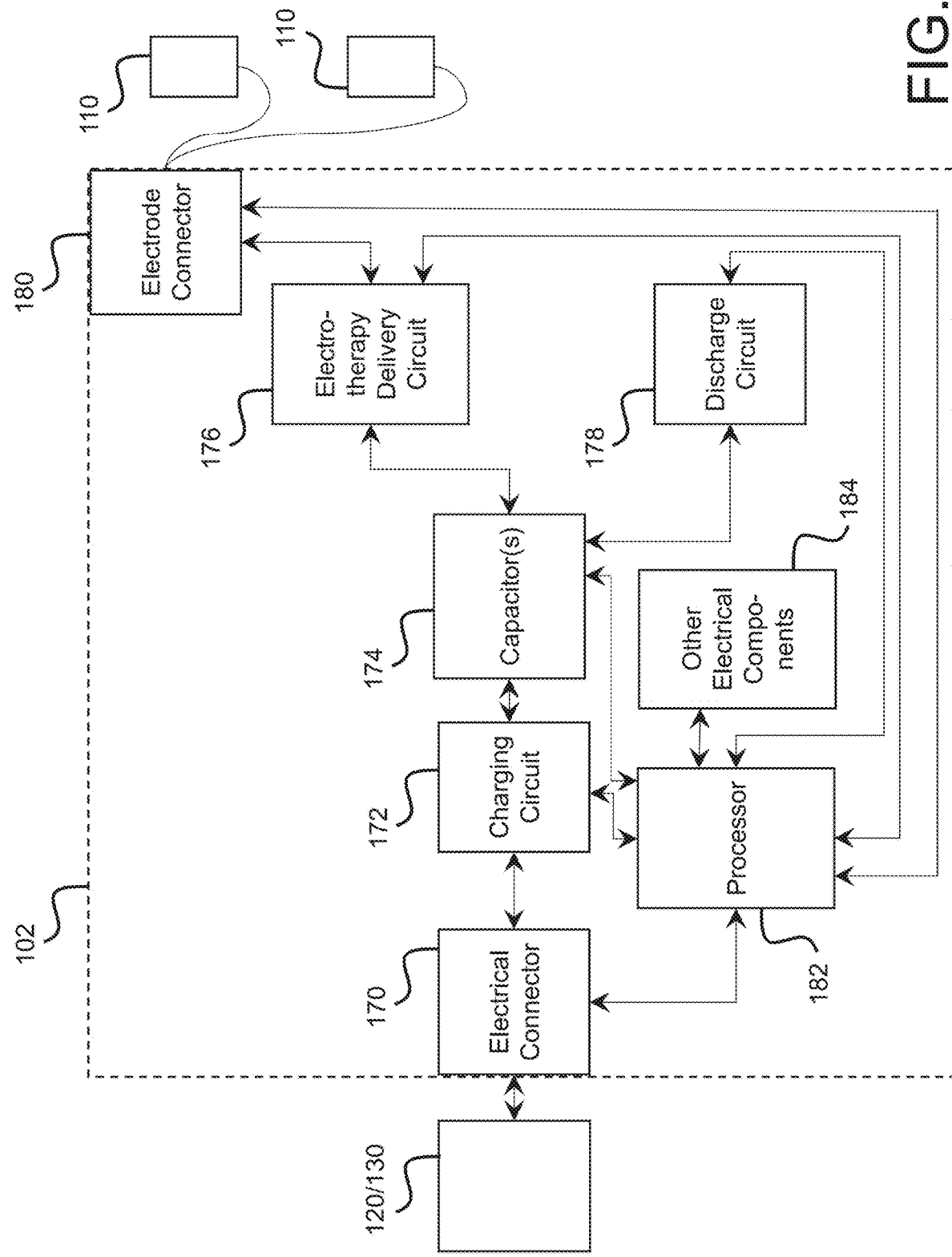

In some embodiments, AED 102 may include electrical connector 170, which may be configured to receive a first power supply (e.g., battery pack 120 and/or the like). Additionally or alternatively, AED 102 may include a second power supply. For example, the second power supply may include at least one of non-clinical power adapter 130, second battery pack 130*a*, any combination thereof, and/or the like. In some embodiments, the second power supply (e.g., non-clinical power adapter 130 and/or the like) may be integrated into AED 102 (e.g., as depicted in FIG. 1B). Additionally or alternatively, the second power supply (e.g., non-clinical power adapter 130, second battery pack 130*a*, and/or the like) may be configured to be received by a second electrical connector 170*a* (e.g., as depicted in FIG. 1C). In some embodiments, AED 102 may include at least one circuit (e.g., charging circuit 172, processor 182, and/or the like) configured to charge capacitor(s) 174 with power from the first power supply (e.g., battery pack 120 and/or the like) and/or to power a plurality of non-clinical features with the second power supply (e.g., non-clinical power adapter 130, second battery pack 130*a*, and/or the like). For example, the non-clinical features may include at least one of diagnostic testing of AED 102, configurability of AED 102, data transfer between AED 102 and external device 150, training operations of AED 102, any combination thereof, and/or the like.

In some embodiments, if AED 102 is in a clinical mode, charging capacitor(s) 174 may include charging capacitor(s) 174 to a predetermined threshold that is greater than or equal to a minimum energy setting for clinical use (e.g., at least 50 J, at least 70 J, at least 85 J, at least 100 J, at least 120 J, at least 150 J, at least 200 J, and/or the like), as described herein. In some embodiments, AED 102 (e.g., electrotherapy delivery circuit 176 thereof) may be configured to deliver the energy externally as electrotherapy to the patient in response to control 180 (e.g., a control on an exterior of AED 102) if the automated external defibrillator is in the clinical mode.

In some embodiments, if AED 102 is in a non-clinical mode, charging capacitor(s) 174 may include charging capacitor(s) 174 to a predetermined threshold that is less than a minimum energy setting for clinical use (e.g., less than 50 J, less than 20 J, less than 10 J, less than 5 J, less than 2 J, 0.1 J to 5 J, 0.1 J to 2 J, any combination thereof, and/or the like), as described herein. In some embodiments, AED 102 (e.g., discharge circuit 178 thereof) may be configured to internally discharge the energy stored in capacitor(s) 174 in response to control 180 (e.g., a control on an exterior of AED 102) if the automated external defibrillator is in the non-clinical mode. Additionally or alternatively, delivery of the energy externally as electrotherapy may be disabled if AED 102 is in the non-clinical mode.

In some embodiments, a first power supply (e.g., for AED 102) may include battery pack 120. Additionally or alternatively, a second power supply (e.g., for AED 102) may include at least one of non-clinical power adapter 130, second battery pack 130a, any combination thereof, and/or the like. For example, non-clinical power adapter 130 may include a voltage converter configured to convert alternating current (AC) input power to direct current (DC) output power (e.g., which may be supplied to AED 102).

External device 150 may include one or more devices capable of receiving information from and/or communicating information to AED 102 (e.g., directly, indirectly via communication network 160, and/or the like). In some embodiments, external device 150 may include a server, a group of servers, and/or other like devices, as described herein. Additionally or alternatively, external device 150 may include at least one other computing device separate from or including the server and/or group of servers, such as a portable and/or handheld device (e.g., a computer, a laptop, a personal digital assistant (PDA), a smartphone, a tablet, and/or the like), a desktop computer, a universal serial bus (USB) drive, a flash drive, and/or other like devices, as described herein. In some embodiments, external device 150 may be associated with a clinical archive, database, and/or the like, as described herein. Additionally or alternatively, external device 150 may be associated with a cardiac monitoring facility and/or the like, as described herein. Additionally or alternatively, the clinical archive, database and/or cardiac monitoring facility may be associated with a provider (e.g., manufacturer, distributor, and/or the like) of AED 102, as described herein. In some embodiments, external device 150 may be associated with a database for managing AEDs, e.g., to ensure that the AEDs are clinically fit for use at any given moment. For example, a non-clinical function of the AEDs may be to upload self-test diagnostic information regarding the readiness status of the AED at the time of uploading. The database for AED management may be used to determine whether one or more of the AEDs in the field need servicing (e.g., replacement of electrodes and/or battery, maintenance/repairs on other clinical related functions, any combination thereof, and/or the like). In some embodiments, the external device 150 may be associated with a database for managing clinical data recorded by AEDs that have been used in a clinical event (e.g., a medical event). For example, when an AED is used during a clinical event, the AED may record a clinical file associated with the event, which may include medical information associated therewith, e.g., the number of defibrillation shocks given to the patient, the particular ECG rhythm associated with each of the defibrillation shocks, chest compression performance information (e.g., average compression depth, average compression rate, pre-shock pause, post-shock pause, compression fraction, any combination thereof, and/or the like). In some embodiments, a non-clinical function of the AEDs (e.g., AED 102) may be to upload clinical event data associated with use of the AED during a clinical event (e.g., a medical event).

Communication network 160 may include one or more wired and/or wireless networks. For example, communication network 160 may include a cellular network (e.g., a long-term evolution (LTE) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network (e.g., a private network associated with a transaction service provider), an ad hoc network, an intranet, the Internet, a fiber optic-based network, a cloud computing network, and/or the like, and/or a combination of these or other types of networks.

Referring now to FIG. 2, FIG. 2 shows an example flowchart of a non-limiting embodiment of a process 200 for a non-clinical power adapter for an AED. In some embodiments, one or more of the steps of process 200 may be performed (e.g., completely, partially, and/or the like) by processor 182. In some embodiments, one or more of the steps of process 200 may be performed (e.g., completely, partially, and/or the like) by another component, another device, another group of components, or another group of devices, separate from or including processor 182, such as AED 102, cavity 104, display 106, control 108, electrodes 110, battery pack 120, non-clinical power adapter 130, second battery pack 130a, input connection 132, power supply 140, external device 150, communication network 160, electrical connector 170, second electrical connector 170a, charging circuit 172, capacitor(s) 174, electrotherapy delivery circuit 176, discharge circuit 178, electrode connector 180, other electrical components 184, and/or the like.

As shown in FIG. 2, at step 202, process 200 may include determining whether a non-clinical power adapter is connected. For example, processor 182 may determine whether non-clinical power adapter 130 is electrically coupled to electrical connector 170.

In some embodiments, non-clinical power adapter 130 may include a memory (e.g., other electrical components 184 may include the memory), which may store at least one identifier (e.g., model number, serial number, any combination thereof, and/or the like) of non-clinical power adapter 130, as described herein. Additionally or alternatively, the memory may include additional data (e.g., expiration date, capacity, voltage rating, current rating, any combination thereof, and/or the like) associated with non-clinical power adapter 130, as described herein. In some embodiments, determining whether non-clinical power adapter 130 is electrically coupled to electrical connector 170 may include reading (e.g., by processor 182) the identifier(s) from the memory. For example, the memory may include an EEPROM and/or the like, as described herein. Additionally or alternatively, a communication line (e.g., a serial communication line, a serial communication bus, an inter-integrated circuit (I2C) line, and/or the like) may connect electrical connector 170 and the memory, and/or processor 182 may be connected to electrical connector 170 (e.g., the communication line(s) thereof). In some embodiments, include reading the identifier(s) from the memory may include the memory communicating and/or processor 182 reading the identifier(s) via the communication line and electrical connector 170.

In embodiments, non-clinical power adapter 130 may be configured to supply power having a first voltage and a first current. Additionally or alternatively, battery pack 120 may be configured to supply power having a second voltage and a second current. In some embodiments, the first voltage and/or the first current may be different than the second voltage and/or the second current, respectively. For example, the first voltage may be 12 V and the first current may be at least one of 3 A or 5 A, and/or the second voltage may be 12 V and the second current may be 6.5 A. In some embodiments, determining whether non-clinical power adapter 130 is electrically coupled to electrical connector 170 may include detecting (e.g., by processor 182 and/or the like) that the first voltage and/or the first current is different than the second voltage and/or the second current, respectively.

As shown in FIG. 2, at step 204, process 200 may include determining whether the AED recognizes the non-clinical power adapter. For example, processor 182 may determine whether AED 102 recognizes non-clinical power adapter 130.

In some embodiments, determining whether AED 102 recognizes the non-clinical power adapter may include determining (e.g., by processor 182) whether AED 102 is compatible with non-clinical power adapter 130. For example, processor 182 may determine whether software of AED 102 recognizes non-clinical power adapter 130 (e.g., the identifier thereof, the first voltage and/or first current thereof, and/or the like). For the purpose of illustration, processor 182 may determine whether a version of the software installed on AED 102 recognizes the non-clinical power adapter. Additionally or alternatively, processor 182 may determine whether software of AED 102 is compatible with non-clinical power adapter 130, whether hardware of AED 102 is compatible with the non-clinical power adapter, any combination thereof, and/or the like. For example, processor 182 may determine whether a version of the software installed on AED 102 is compatible with non-clinical power adapter 130. Additionally or alternatively, processor 182 may determine whether the hardware of AED 102 is compatible with non-clinical power adapter 130 (e.g., based on the first voltage thereof, the first current thereof, based on whether pins of electrical connector 170 are compatible with non-clinical power adapter 130, any combination thereof, and/or the like).

As shown in FIG. 2, at step 206, process 200 may include enabling power to be supplied to the AED from the non-clinical power adapter. For example, processor 182 may enable power to be supplied to AED 102 from non-clinical power adapter 130 if AED 102 recognizes non-clinical power adapter 130.

In some embodiments, enabling power to be supplied to AED 102 from non-clinical power adapter 130 may include enabling (e.g., by processor 182) AED 102 to operate in a non-clinical mode. For example, operating in a non-clinical mode may include at least one of disabling (e.g., by processor 182, electrotherapy delivery circuit 176, and/or the like) delivery of energy externally as electrotherapy, charging (e.g., by processor 182, charging circuit 172, and/or the like) capacitor(s) 174 to a predetermined threshold that is less than a minimum energy setting for clinical use, discharging (e.g., by processor 182, discharge circuit 178, and/or the like) the stored energy from capacitor(s) 174 internally (e.g., through discharge circuit 178), any combination thereof, and/or the like, as described herein. In some embodiments, the stored energy from capacitor(s) 174 may be discharged internally through discharge circuit 172 in response to control 108, as described herein, for example, when AED 102 is operating in a manual or semi-automatic mode. Additionally or alternatively, the stored energy from capacitor(s) 174 may be discharged internally through discharge circuit 172 automatically (e.g., without the need to activate control 108 and/or the like), for example, when AED 102 is operating in an automatic (e.g., fully automatic) mode. In some embodiments, control 108 may include a shock button.

In some embodiments, the predetermined threshold (e.g., for charging capacitor(s) 174) may include at least one of less than 50 J, less than 20 J, less than 10 J, less than 5 J, less than 2 J, 0.1 J to 5 J, 0.1 J to 2 J, any combination thereof, and/or the like. For example, the predetermined threshold may include less than 10 J. Additionally or alternatively, the predetermined threshold may include 2 J.

In some embodiments, AED 102 may include a plurality of electrical components (e.g., other electrical components 184 and/or the like) other than capacitor(s) 174, as described herein. Additionally or alternatively, enabling AED 102 to operate in a non-clinical mode may include enabling (e.g., by processor 182 and/or the like) power to be supplied to the plurality of electrical components (e.g., other electrical components 184 and/or the like) from non-clinical power adapter 130 (e.g., via electrical connection 170 and/or the like). For example, enabling power to be supplied to the plurality of electrical components (e.g., other electrical components 184 and/or the like) may include operating such components as such components operate in a clinical mode. For the purpose of illustration, for training purposes, it may be desirable to operate such components (e.g., chest compression feedback features, resuscitation prompting, ECG analysis, and/or the like) as such components operate in the clinical mode while preventing the possibility of inadvertent shock, as described herein.

As shown in FIG. 2, at step 208, process 200 may include disabling (e.g., cutting off and/or the like) power from the non-clinical power adapter to the AED. For example, processor 182 may disable the power being supplied to AED 102 from non-clinical power adapter 130 if the AED 102 does not recognize non-clinical power adapter 130.

In some embodiments, a communication line (e.g., a serial communication line, a serial communication bus, an inter-integrated circuit (I2C) line, and/or the like) may connect electrical connector 170 and a switching element of non-clinical power adapter 130. Additionally or alternatively, processor 182 may be connected to electrical connector 170 (e.g., the communication line(s) thereof). Additionally or alternatively, an I/O line may connect the switching element and a voltage regulator of non-clinical power adapter 130. In some embodiments, disabling the power being supplied to AED 102 from non-clinical power adapter 130 may include communicating (e.g., by processor 182) with the switching element (e.g., via the communication line, electrical connector 170, and/or the like) to set (e.g., cause the switching elements to set) the I/O line to a first logical voltage. Additionally or alternatively, enabling power to be supplied to AED 102 from the non-clinical power adapter 130 may include communicating (e.g., by processor 182) with the switching element (e.g., via the communication line, electrical connector 170, and/or the like) to maintain (e.g., cause the switching elements to maintain) the I/O line at a second logical voltage. In some embodiments, the voltage regulator of non-clinical power adapter 130 may be configured to supply power (e.g., from non-clinical power adapter 130 to AED 102 and/or the like) when the I/O line is set to the second logical voltage and/or to stop supplying power (e.g., from non-clinical power adapter 130 to AED 102 and/or the like) from the non-clinical power adapter to the automated external defibrillator when the I/O line is set to the first logical voltage. In some embodiments, the first logical voltage may include at least one of a low logical voltage, less than 2.5 V, less than 3.3 V, or less than 5 V. Additionally or alternatively, the second logical voltage may include at least one of a high logical voltage, greater than 2.5 V, greater than 3.3 V, or greater than 5 V. In some embodiments, the switching element may include a battery monitor circuit (e.g., a gas gauge, a fuel gauge, and/or the like). For example, the battery monitor circuit may be repurposed to be used as a switching element, e.g., by using the I/O line thereof. Additionally or alternatively, such repurposing may be desirable when connecting non-clinical power adapter 130 to electrical connector 170 (e.g., which may be configured to receive battery pack 120 that may include a battery monitor circuit that is the same as or similar to the battery monitor circuit in non-clinical power adapter 130), since electrical connector 170 and/or AED 102 may not need to be modified and/or may only need to be slightly modified (e.g., by updating a software version of AED 102 and/or the like without a need to change the hardware of AED 102 and/or the like) to be compatible with non-clinical power adapter 130. In some embodiments, the battery monitor circuit may be configured to disable the voltage regulator of non-clinical power adapter 130 by setting the I/O line to the first logical voltage, as described herein. For example, the I/O line may be set to the second logical voltage (e.g., high logical voltage and/or the like) by default (e.g., at startup, when non-clinical power adapter 130 is initially connected to electrical connector 170, and/or the like), and/or processor 182 may communicate with the battery monitor circuit (e.g., via the communication line, electrical connector 170, and/or the like) to set (e.g., cause the battery monitor circuit to set) the I/O line to the first logical voltage (e.g., low logical voltage and/or the like) to disable power from non-clinical power adapter 130 to AED 102 (e.g., in response a determination by processor 182 that non-clinical power adapter 130 is incompatible with AED 102). Additionally or alternatively, the I/O line may be maintained (e.g., allowed to maintain by processor 182 and/or the like) at the second logical voltage (e.g., high logical voltage and/or the like) to enable power from non-clinical power adapter 130 to AED 102 (e.g., in response a determination by processor 182 that non-clinical power adapter 130 is compatible with AED 102).

Figure 3:
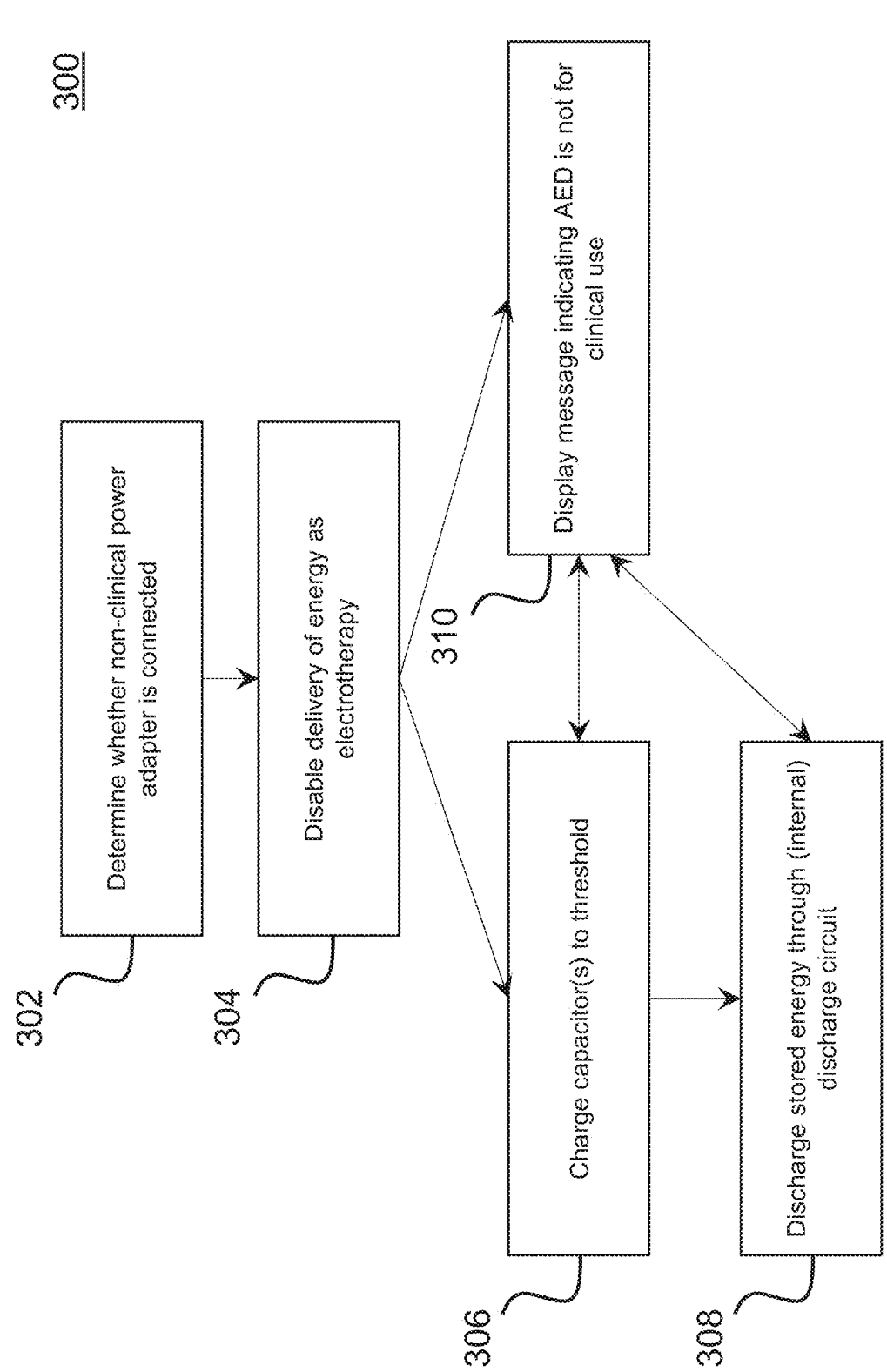
FIG. 3 shows an example flowchart of a process for a non-clinical power adapter for an automated external defibrillator, according to some embodiments.

Referring now to FIG. 3, FIG. 3 shows an example flowchart of a non-limiting embodiment of a process 300 for a non-clinical power adapter for an AED. In some embodiments, one or more of the steps of process 300 may be performed (e.g., completely, partially, and/or the like) by processor 182. In some embodiments, one or more of the steps of process 300 may be performed (e.g., completely, partially, and/or the like) by another component, another device, another group of components, or another group of devices, separate from or including processor 182, such as AED 102, cavity 104, display 106, control 108, electrodes 110, battery pack 120, non-clinical power adapter 130, second battery pack 130*a*, input connection 132, power supply 140, external device 150, communication network 160, electrical connector 170, second electrical connector 170*a*, charging circuit 172, capacitor(s) 174, electrotherapy delivery circuit 176, discharge circuit 178, electrode connector 180, other electrical components 184, and/or the like.

As shown in FIG. 3, at step 302, process 300 may include determining whether a non-clinical power adapter is connected. For example, processor 182 may determine whether non-clinical power adapter 130 is electrically coupled to electrical connector 170 of AED 102, as described herein.

As shown in FIG. 3, at step 304, process 300 may include disabling delivery of energy as electrotherapy. For example, processor 182 may disable delivery of energy externally as electrotherapy (e.g., disable electrotherapy delivery circuit 176, electrode connector 180, any combination thereof, and/or the like), as described herein.

In some embodiments, processor 182 may enable power to be supplied from non-clinical power adapter 130 (e.g., via electrical connector 170) to a plurality of electrical components (e.g., other electrical components 184 and/or the like) other than capacitor(s) 174, as described herein.

As shown in FIG. 3, at step 306, process 300 may include charging the capacitor(s) to a threshold. For example, processor 182 may charge (e.g., cause charging circuit 172 to charge) capacitor(s) 174 to a predetermined threshold that is less than a minimum energy setting for clinical use, as described herein.

In some embodiments, the predetermined threshold may include at least one of less than 50 J, less than 20 J, less than 10 J, less than 5 J, less than 2 J, 0.1 J to 5 J, 0.1 J to 2 J, any combination thereof, and/or the like, as described herein.

As shown in FIG. 3, at step 308, process 300 may include discharging stored energy through a discharge circuit. For example, processor 182 may discharge (e.g., cause discharge circuit 178 to discharge) the stored energy from capacitor(s) 174 internally (e.g., through discharge circuit 178 and/or the like), as described herein.

In some embodiments, processor 182 and/or discharge circuit 178 may discharge the stored energy from capacitor(s) 174 internally (e.g., through discharge circuit 178) in response to a first control 108 on an exterior of AED 102, as described herein. For example, the first control 108 may include a shock button. In some embodiments, the shock button may include a light (e.g., a light emitting diode (LED) and/or the like). For example, the energy stored in capacitor(s) 174 may enable the light to turn on before the button is pressed, and/or the energy stored by capacitor(s) 174 may be discharged (e.g., through discharge circuit 178) in response to the shock button being pressed.

In some embodiments, AED 102 may include a second control 108*a* (e.g., on an exterior of AED 102 and/or the like). For example, second control 108*a* may include a child button. In some embodiments, processor 182 may be configured to switch from an adult mode to a pediatric mode in response to the second control 108*a*.

As shown in FIG. 3, at step 310, process 300 may include displaying a message indicating that the AED is not for clinical use. For example, processor 182 may display (e.g., cause display 106 to display) a message indicating that AED 102 is not enabled for clinical use (e.g., via display 106), as described herein.

In some embodiments, AED 102 may include display 106 on an exterior of AED 102. Additionally or alternatively, processor 182 may (e.g., in response to determining non-clinical power adapter 130 is electrically coupled to electrical connector 170) display (e.g., cause display 106 to display) a message indicating that AED 102 is not enabled for clinical use.

In some embodiments, AED 102 may include a speaker. Additionally or alternatively, processor 182 may (e.g., in response to determining non-clinical power adapter 130 is electrically coupled to electrical connector 170) play (e.g., cause the speaker to play) an announcement indicating that AED 102 is not enabled for clinical use.

Figure 4:
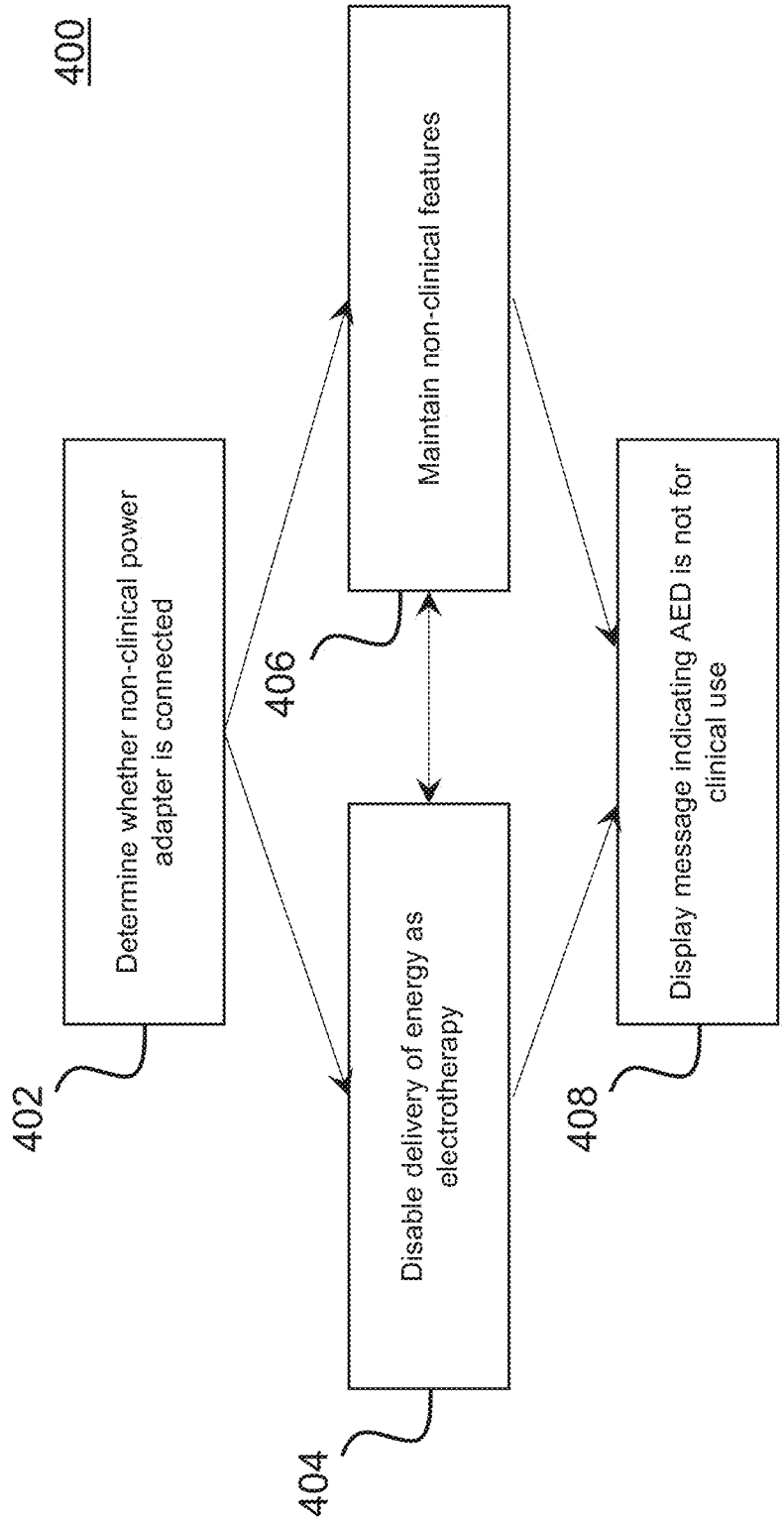
FIG. 4 shows an example flowchart of a process for a non-clinical power adapter for an automated external defibrillator, according to some embodiments.

Referring now to FIG. 4, FIG. 4 shows an example flowchart of a non-limiting embodiment of a process 400 for a non-clinical power adapter for an AED. In some embodiments, one or more of the steps of process 400 may be performed (e.g., completely, partially, and/or the like) by processor 182. In some embodiments, one or more of the steps of process 400 may be performed (e.g., completely, partially, and/or the like) by another component, another device, another group of components, or another group of devices, separate from or including processor 182, such as AED 102, cavity 104, display 106, control 108, electrodes 110, battery pack 120, non-clinical power adapter 130, second battery pack 130*a*, input connection 132, power supply 140, external device 150, communication network 160, electrical connector 170, second electrical connector 170*a*, charging circuit 172, capacitor(s) 174, electrotherapy delivery circuit 176, discharge circuit 178, electrode connector 180, other electrical components 184, and/or the like.

As shown in FIG. 4, at step 402, process 400 may include determining whether a non-clinical power adapter is connected. For example, processor 182 may determine whether non-clinical power adapter 130 is electrically coupled to electrical connector 170 of AED 102, as described herein.

As shown in FIG. 4, at step 404, process 400 may include disabling delivery of energy as electrotherapy. For example, processor 182 may disable delivery of energy externally as electrotherapy (e.g., disable electrotherapy delivery circuit 176, electrode connector 180, any combination thereof, and/or the like), as described herein.

In some embodiments, processor 182 and/or charging circuit 172 may charge capacitor(s) 174 to a predetermined threshold that is less than a minimum energy setting for clinical use, as described herein. Additionally or alternatively, processor 182 and/or discharge circuit 178 may discharge the stored energy from the capacitor(s) 174 internally (e.g., through discharge circuit 178), as described herein.

In some embodiments, processor 182 may be further configured to maintain at least one clinical feature other than delivery of the energy externally as electrotherapy, as described herein. For example, such clinical feature(s) may include at least one of an electrocardiogram (ECG) or shock analysis feature, a resuscitation prompting feature, a resuscitation feedback (e.g., chest compression feedback) feature, or any combination thereof.

In some embodiments, the ECG or shock analysis feature may include at least one of detecting (e.g., by processor 182 and/or other electrical components 184) a heart rhythm via at least one electrode 110 connected to AED 102 (e.g., via electrode connector 180), detecting an ECG via the electrode(s) 110, determining (e.g., by processor 182) whether the heart rhythm or the ECG is shockable based on analyzing the heart rhythm or the ECG, detecting (e.g., by processor 182 and/or other electrical components 184) an electrode type of the at least one electrode, receiving (e.g., by processor 182 and/or other electrical components 184) impedance data from the at least one electrode, determining (e.g., by processor 182) whether the at least one electrode is properly attached based on the impedance data, any combination thereof, and/or the like. In some embodiments, in a training scenario, AED 102 may be coupled to an ECG simulator that outputs a particular ECG rhythm that AED 102 (e.g., processor 182 thereof) may analyze, and/or AED 102 (e.g., processor 182 thereof) may provide (e.g., based on the simulated ECG rhythm) an indication of whether the simulated ECG rhythm is shockable or non-shockable. As such, a user being trained may be able to proceed through the appropriate (e.g., corresponding) resuscitation prompts depending on what simulated ECG rhythm is selected. For example, in a training scenario, if the simulated ECG rhythm is of a shockable nature, then AED 102 may prompt the user that a shockable rhythm is detected and to press the shock button (e.g., control 108) when ready and then commence chest compressions immediately afterward. Additionally or alternatively, if the simulated ECG rhythm is of a non-shockable nature, then AED 102 may prompt the user that no shock is advised and then to proceed to chest compressions immediately afterward.

In some embodiments, the resuscitation prompting feature(s) may include displaying (e.g., by processor 182 via display 106) a graphical user interface comprising at least one prompt for performing at least one of chest compressions or cardiopulmonary resuscitation (CPR). Additionally or alternatively, AED 102 may include a speaker, and/or the resuscitation prompting feature(s) may include at least one of playing (e.g., by processor 182 via the speaker) at least one announcement for performing the at least one of the chest compressions or the CPR, playing (e.g., by processor 182 via the speaker) a metronome tone for performance of the chest compressions, providing chest compression feedback for the user to stay within a target range of chest compression depth and a target range of chest compression rate, any combination thereof, and/or the like.

In some embodiments, the resuscitation feedback feature(s) may include at least one of receiving (e.g., by processor 182 and/or the like) accelerometer data from a chest compression sensor (e.g., a chest compression sensor separate from, connected to, and/or integrated with at least one of the electrode(s) 110) connected to AED 102 and/or held or otherwise placed on the sternum of the patient during chest compressions, receiving (e.g., by processor 182 and/or the like) other sensor data from at least one other sensor connected to AED 102, displaying (e.g., by processor 182 via display 106 and/or the like) feedback data for at least one of the chest compressions or CPR, playing (e.g., by processor 182 via a speaker and/or the like) at least one announcement for feedback for the at least one of the chest compressions or the CPR, any combination thereof, and/or the like. For example, processor 182 may cause display 106 to display a graphical user interface comprising at least one prompt for adjusting and/or maintaining performance of the chest compressions and/or the CPR. Additionally or alternatively, the graphical user interface (e.g., displayed by processor 182 via display 106 and/or the like) may include a depth indicator of depth of the chest compressions. Additionally or alternatively, the graphical user interface (e.g., displayed by processor 182 via display 106 and/or the like) may include an event time indicator of elapsed time of an event (e.g., a clinical event, a training event, and/or the like) during which the chest compressions and/or the CPR is being performed. Additionally or alternatively, the graphical user interface (e.g., displayed by processor 182 via display 106 and/or the like) may include a shock indicator of a number of defibrillating shocks (or a number of discharges of the energy stored in capacitor(s) 174 via discharge circuit 178, e.g., during a non-clinical and/or training event).

In some embodiments, training operations of AED 102 may include using the at least one clinical feature (e.g., that is maintained, enabled and/or the like) as such feature operates in a clinical mode (e.g., while delivery of the energy externally as electrotherapy is disabled).

As shown in FIG. 4, at step 406, process 400 may include maintaining non-clinical features. For example, processor 182 may maintain a plurality of non-clinical features of AED 102.

In some embodiments, as discussed herein, the plurality of non-clinical features may include at least one of diagnostic testing of AED 102, configurability of AED 102, data transfer between AED 102 and external device 150, training operations of AED 102, or any combination thereof.

In some embodiments, the diagnostic testing of AED 102 may include at least one of testing (e.g., by processor 182, other electrical components 184, AED 102, and/or the like) whether sufficient power is being supplied to AED 102 (e.g., by battery pack 120, non-clinical adapter 130, and/or second battery pack 130a), testing (e.g., by processor 182, other electrical components 184, AED 102, and/or the like) whether at least one electrode 110 is properly connected (e.g., via electrode connector 180) to AED 102, determining (e.g., by processor 182 and/or the like) whether the electrode(s) 110 are expired, testing (e.g., by processor 182, other electrical components 184, AED 102, and/or the like) ECG circuitry (e.g., which may be part of other electrical components 184 and/or the like) of AED 102, testing (e.g., by processor 182, other electrical components 184, AED 102, and/or the like) capacitor(s) 174, testing (e.g., by processor 182, other electrical components 184, AED 102, and/or the like) discharge circuit 178, testing (e.g., by processor 182, other electrical components 184, AED 102, and/or the like) processor 182, testing (e.g., by processor 182, other electrical components 184, AED 102, and/or the like) chest compression or CPR feedback circuitry (e.g., which may be part of other electrical components 184 and/or the like), testing (e.g., by processor 182, other electrical components 184, AED 102, and/or the like) a speaker (e.g., which may be part of other electrical components 184 and/or the like) and/or audio circuitry (e.g., which may be part of other electrical components 184 and/or the like) of AED 102, testing (e.g., by processor 182, other electrical components 184, AED 102, and/or the like) battery pack 120 (and/or non-clinical adapter 130 and/or second battery pack 130*a*), determining (e.g., by processor 182 and/or the like) whether battery pack 120 (and/or non-clinical adapter 130 and/or second battery pack 130*a*) is expired or below a threshold energy level, performing (e.g., by processor 182, other electrical components 184, AED 102, and/or the like) a simulator test, performing (e.g., by processor 182, other electrical components 184, AED 102, and/or the like) other internal diagnostic testing of AED 102, any combination thereof, and/or the like.

In some embodiments, configurability of AED 102 may include at least one of configuring (e.g., by processor 182, display 106 (which may be a touchscreen display), and/or the like) a language setting, configuring (e.g., by processor 182, display 106, and/or the like) a lay rescuer setting, configuring (e.g., by processor 182, display 106, and/or the like) a breathing check setting, configuring (e.g., by processor 182, display 106, and/or the like) a chest compression feedback setting or a CPR feedback setting, configuring (e.g., by processor 182, display 106, and/or the like) a date setting, configuring (e.g., by processor 182, display 106, and/or the like) a time setting, configuring (e.g., by processor 182, display 106, and/or the like) a number of clinical cases setting, configuring (e.g., by processor 182, display 106, and/or the like) a self-test interval setting, configuring (e.g., by processor 182, display 106, and/or the like) an automated self-test report setting, configuring (e.g., by processor 182, display 106, and/or the like) an audio recording setting, configuring (e.g., by processor 182, display 106, and/or the like) a resuscitation prompting setting, configuring (e.g., by processor 182, display 106, and/or the like) a passcode, configuring (e.g., by processor 182, display 106, and/or the like) a device identifier, configuring (e.g., by processor 182, display 106, and/or the like) an energy level setting for at least one of an adult mode or a pediatric mode, configuring (e.g., by processor 182, display 106, and/or the like) a breath prompting setting, configuring (e.g., by processor 182, display 106, and/or the like) a continue resuscitation prompting setting, configuring (e.g., by processor 182, display 106, and/or the like) a resuscitation prompting interval setting, configuring (e.g., by processor 182, display 106, and/or the like) a start with resuscitation setting, configuring (e.g., by processor 182, display 106, and/or the like) a no-shock period setting, configuring (e.g., by processor 182, display 106, and/or the like) a post-shock period setting, configuring (e.g., by processor 182, display 106, and/or the like) a wireless network setting, any combination thereof, and/or the like. In some embodiments, the language setting may include selecting at least one language. For example, a user may select one language, up to three languages (e.g., in an order of priority), and/or the like. In some embodiments, the lay rescuer setting may include enabling or disabling lay rescuer (e.g., non-professional) prompts. For example, when enabled, lay rescuer prompts may include prompts (e.g., displayed messages on display 106, announced prompts from a speaker, and/or the like) intended for a lay (e.g., non-professional) user, such as "STAY CALM," "CHECK RESPONSIVENESS," "CALL FOR HELP," and/or the like. In some embodiments, the breathing check setting may include enabling or disabling prompts to check breathing. For example, when enabled, prompts to check breathing may include prompts to "OPEN AIRWAY," "CHECK BREATHING," and/or the like. In some embodiments, a chest compression feedback setting or a CPR feedback setting may include selecting units (e.g., inches, centimeters, and/or the like) for chest compression depth indicators. In some embodiments, a date setting may include setting and/or selecting the date. In some embodiments, a time setting may include setting and/or selecting the time and/or setting and/or selecting the time zone. In some embodiments, a number of clinical cases setting may include setting a number of patient cases that are stored in memory. For example, the number of patient cases may be 1, 2, and/or the like. In some embodiments, a self-test interval setting may include setting and/or selecting a period of time between automated self-tests (e.g., when the AED is in a standby state). For example, the period may be 1 day, 7 days, and/or the like. In some embodiments, an automated self-test report setting may include enabling or disabling automated reporting of diagnostic testing data after self-testing (e.g., periodic self-tests by the AED). For example, when enabled, after completion of a self-test, the AED may attempt to communicate diagnostic testing data to at least one external device (e.g., connect to a wireless network and wirelessly communicate the diagnostic testing data to the external device(s)). In some embodiments, an audio recording setting may include enabling or disabling recording of audio during a clinical event. In some embodiments, a resuscitation prompting setting may include selecting an option for the GUI displayed during a clinical event. For example, the options may include a lay rescuer option (e.g., displaying text prompts and graphics according to a lay rescuer mode), a CPR only option (e.g., displaying text prompts and/or CPR feedback graphics according to a professional mode), a CPR and ECG option (e.g., displaying text prompts, ECG rhythm, and/or CPR feedback graphics according to a professional mode). In some embodiments, a passcode may include setting and/or inputting a passcode to enter a supervisor mode. For example, the passcode may include numeric digits (e.g., 4 numeric digits, 6 numeric digits, and/or the like), an alphanumeric passcode, any combination thereof, and/or the like. In some embodiments, a device identifier may include setting and/or inputting a device identifier (e.g., alphanumeric string, name, and/or the like) for the AED. In some embodiments, an energy level setting may include setting and/or selecting energy levels (e.g., in joules (J) and/or the like) for first, second, and/or third defibrillation shocks for at least one of an adult mode or a pediatric mode. In some embodiments, a breath prompting setting may include enabling or disabling prompts to give breaths during resuscitation (e.g., CPR and/or the like). For example, when enabled, the prompts may include an instruction indicating to the rescuer to give breaths to the patient (e.g., "Give Two Breaths") after a predetermined number of chest compressions (e.g., every 30 recognized chest compressions and/or the like). In some embodiments, a continue resuscitation prompting setting may include enabling or disabling prompts to continue resuscitation (e.g., "CONTINUE CPR" and/or the like) at selectable periods (e.g., based on the resuscitation prompting interval setting) if resuscitation actions (e.g., chest compressions and/or the like) stop during a resuscitation interval. In some embodiments, configuring a resuscitation prompting interval setting may include setting and/or selecting the period for the prompts to continue resuscitation. In some embodiments, configuring a start with resuscitation setting may include enabling, disabling, and/or selecting a duration for a period during which the AED will instruct the user to begin by performing resuscitation (e.g., CPR and/or the like), e.g., once pads (e.g., electrodes, sensors, and/or the like) are attached to the patient. For example, the selections for the start with resuscitation setting may include off, 30 seconds, 60 seconds, 90 seconds, 120 seconds, 150 seconds, 180 seconds, and/or the like. In some embodiments, configuring a no-shock period setting may include setting and/or selecting the period (e.g., length) of a CPR interval following a determination by the AED to not shock the patient. For example, the periods for the no-shock period setting may include 60 seconds, 90 seconds, 120 seconds, 150 seconds, 180 seconds, and/or the like. In some embodiments, configuring a post-shock period setting may include setting and/or selecting the period (e.g., length) of a CPR interval following delivery of a defibrillation shock from the AED to the patient. For example, the periods for the post-shock period setting may include 60 seconds, 90 seconds, 120 seconds, 150 seconds, 180 seconds, and/or the like. In some embodiments, the wireless network setting may include setting and/or selecting at least one of a network identifier (e.g., Service Set Identifier (SSID)) for a wireless network, a password for the wireless network, server settings for the wireless network and/or an external device connected thereto (e.g., an address (e.g., domain and/or web address) for the server, a user identifier (e.g., username) for connecting to and/or authenticating with the server, a password and/or passcode associated with the user identifier, and/or the like), an Internet protocol (IP) address (e.g., local IP address, gateway IP address, a primary and/or secondary domain name server (DNS) IP address, and/or the like), a subnet mask, any combination thereof, and/or the like.

In some embodiments, data transfer between AED 102 and external device 150 may include at least one of communicating diagnostic testing data based on the diagnostic testing of AED 102 to external device 150, communicating patient data to external device 150, communicating clinical event data to external device 150, communicating voice data to external device 150, communicating audio data to external device 150, communicating device history data to external device 150, receiving at least one software update from external device 150, receiving at least one software upgrade from external device 150, any combination thereof, and/or the like. In some embodiments, diagnostic testing data may include data associated with at least one diagnostic test (e.g., self-test and/or the like) by the AED. In some embodiments, patient data may include at least one of a number of shocks delivered to a patient, impedance of the patient, an indication of attachment of pads (e.g., electrodes, sensors, and/or the like) to the patient, sensor data from sensors connected to the patient, ECG data and/or heart rhythm data from the patient, results of ECG analysis and/or heart rhythm analysis for the patient, resuscitation data (e.g., CPR feedback data and/or the like) for the patient, and/or the like. In some embodiments, clinical event data may include at least one of elapsed time data (e.g., time since the AED was powered on, since the AED was placed into a clinical mode, since the beginning of a clinical event, and/or the like), ECG data and/or heart rhythm data of a patient, a number of defibrillation shocks delivered to the patient, an indication of selected energy for the defibrillation shocks delivered to the patient, impedance of the patient, audio prompt data associated with audio prompts outputted to the user during the clinical event, audio recording data associated with audio recorded during the clinical event, power on data associated with a date and/or time when the AED was powered on, an indication of whether defibrillation pads were attached to the patient, results of ECG analysis and/or heart rhythm analysis, resuscitation data (e.g., CPR feedback data and/or the like) for the clinical event, errors logged during the clinical event, and/or the like. In some embodiments, audio data may include audio prompt data associated with audio prompts outputted to the user during the clinical event, audio recording data associated with audio recorded during the clinical event, and/or the like. In some embodiments, voice data may include audio recording data associated with audio recorded during the clinical event, and/or the like. In some embodiments, device history data may include an identifier (e.g., serial number, model number, and/or the like) of the AED, battery status data (e.g., remaining charge, expiration date, and/or the like) associated with the battery pack, electrode assembly data associated with the electrodes and/or sensors thereof (e.g., expiration date, indication of whether defibrillation pads were attached to the patient, and/or the like), hardware date (e.g., revision number, version number, and/or the like), software data (e.g., revision number, version number and/or the like), diagnostic testing data associated with diagnostic testing (e.g., self-testing and/or the like) of the AED and/or the date and/or time of the respective (e.g., most recent diagnostic test), error code date (e.g., associated with error codes in a most recent self-test and/or the like).

In some embodiments, data transfer between AED 102 and external device 150 may include communicating with external device 150 via a wireless network, communicating with external device 150 via a wired network, communicating with external device 150 via a universal serial bus (USB) port, communicating with external device 150 via a communication interface, any combination thereof, and/or the like.

In some embodiments, AED 102 may include (e.g., other electrical components 184 may include) a memory and/or a communication interface. Additionally or alternatively, AED 102 may record at least one of diagnostic testing data based on the diagnostic testing of AED 102, patient data, clinical event data, device history data, voice data, audio data, any combination thereof, and/or the like in the memory. Additionally or alternatively, in response to determining non-clinical power adapter 130 is electrically coupled to electrical connector 170, AED 102 may communicate the diagnostic testing data, patient data, clinical event data, device history data, any combination thereof, and/or the like to external device 150 via the communication interface.

As shown in FIG. 4, at step 408, process 400 may include displaying a message indicating that the AED is not for clinical use. For example, processor 182 may display (e.g., cause display 106 to display) a message indicating that AED 102 is not enabled for clinical use (e.g., via display 106).

In some embodiments, AED 102 may include display 106 on an exterior of AED 102. Additionally or alternatively, AED 102 (e.g., processor 182 thereof) may, in response to determining non-clinical power adapter 130 is electrically coupled to electrical connector 170, display a message indicating that AED 102 is not enabled for clinical use on display 106. In some embodiments, the message indicating that AED 102 is not enabled for clinical use may be displayed continuously on the screen while the AED is on and during its use, or may be displayed in a more intermittent or limited fashion, such as only when the AED is powered on and/or during the shock analysis portion of the resuscitation prompting, or the like.

In some embodiments, AED 102 may include (e.g., other electrical components 184 may include) a speaker. Additionally or alternatively, AED 102 (e.g., processor 182 thereof) may, in response to determining non-clinical power adapter 130 is electrically coupled to electrical connector 170, play an announcement indicating that AED 102 is not enabled for clinical use, that the AED is set to a non-clinical mode, and/or that the electrotherapeutic energy delivery capability has been disabled from the speaker.

Figure 5:
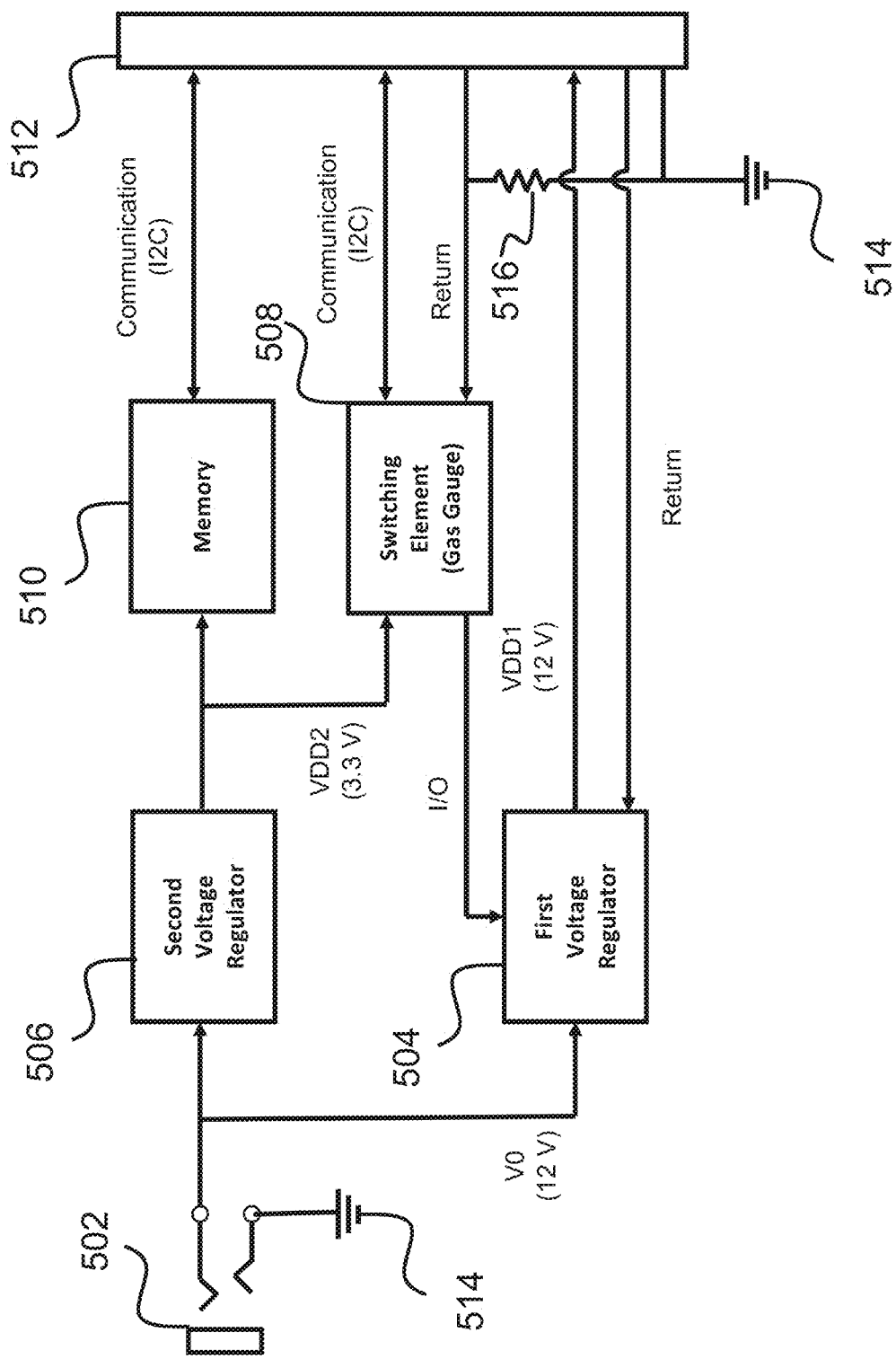
FIG. 5 shows an example block diagram of components of a non-clinical power adapter for an automated external defibrillator, according to some embodiments.

Referring now to FIG. 5, FIG. 5 shows an example block diagram of components of a non-limiting embodiment of a non-clinical power adapter 500 for an AED. In some embodiments, non-clinical power adapter 500 may be the same as or similar to non-clinical power adapter 130. In some embodiments, non-clinical power adapter 500 may include input connection 502, first voltage regulator 504, second voltage regulator 506, switching element 508, memory 510, output connection 512, ground 514, current sense resistor 516, and/or the like.

In some embodiments, input connection 502 may be configured to receive power from (e.g., electrically couple to and/or the like) a power supply (e.g., power supply 140 and/or the like). For example, the power from the power supply may have a voltage (VO) with a voltage range (e.g., 12 V DC plus or minus a first tolerance). Additionally or alternatively, at least one voltage regulator may receive (e.g., by electrical coupling and/or the like) the power (e.g., having a voltage with in the voltage range) from input connection 502. For example, first voltage regulator 504 may be configured to receive power from input connection 502 and/or to supply power having a first voltage (VDD1) within the voltage range to output connection 502. For example, first voltage regulator 504 may be configured to receive power having a voltage of approximately 12 V DC (e.g., plus or minus the first tolerance) and to supply power having precisely 12 V DC (and/or 12 V DC plus or minus a second tolerance that is less than the first tolerance). Additionally or alternatively, second voltage regulator 506 may be configured to receive (e.g., by electrical coupling and/or the like) power (e.g., having a voltage with in the voltage range) from input connection 502 and to supply power having a second voltage (VDD2) less than the voltage range to at least one electronic component (e.g., switching element 508, memory 510, and/or the like) of non-clinical power adapter 500. For example, second voltage regulator 506 may be configured to receive power having a voltage of approximately 12 V DC (e.g., plus or minus the first tolerance) and to supply power of a lower voltage suitable for digital logic (e.g., 3.3 V DC and/or the like) to the electronic component(s) (e.g., switching element 508, memory 510, and/or the like).

In some embodiments, switching element 508 may be connected to first voltage regulator 504 via an input/output (I/O) line. For example, switching element 508 may be configured to disable power being supplied to the AED (e.g., AED 102) from non-clinical power adapter 500 by setting the I/O line to a first logical voltage, as described herein. Additionally or alternatively, switching element 508 may be configured to enable power to be supplied to the AED (e.g., AED 102) from non-clinical power adapter 500 by maintaining the I/O line at a second logical voltage, as described herein.

In some embodiments, output connection 512 may be connected to an electrical connector (e.g., electrical connector 170) of an AED (e.g., AED 102)

In some embodiments, an AED (e.g., AED 102) may include at least one processor (e.g., processor 182) connected to switching element 508 via a communication line (e.g., a I2C line and/or the like, as described herein) from an electrical connector (e.g., electrical connector 170 of AED 102), as described herein. In some embodiments, the processor (e.g., processor 182) may disable power being supplied to the AED (e.g., AED 102) from non-clinical power adapter 500 by communicating with switching element 508 via the communication line (e.g., I2C line and/or the like) to set an I/O line of (e.g., connected to) switching element 508 to a first logical voltage, as described herein. For example, the I/O line may be set to the second logical voltage (e.g., high logical voltage and/or the like) by default, and/or the processor (e.g., processor 182) may communicate with switching element 508 to set the I/O line to the first logical voltage (e.g., low logical voltage and/or the like) to disable power from non-clinical power adapter 500 to the AED (e.g., AED 102), as described herein. Additionally or alternatively, the processor (e.g., processor 182) may enable power to be supplied to the AED (e.g., AED 102) from non-clinical power adapter 500 by communicating with switching element 508 via the communication line (e.g., I2C line and/or the like) to maintain an I/O line of (e.g., connected to) switching element 508 at a second logical voltage, as described herein. For example, the I/O line may be maintained (e.g., allowed to maintain by processor 182 and/or the like) at the second logical voltage (e.g., high logical voltage and/or the like) to enable power from non-clinical power adapter 500 to the AED (e.g., AED 102), as described herein. In some embodiments, the first logical voltage may include at least one of a low logical voltage, less than 2.5 V, less than 3.3 V, less than 5 V, any combination thereof, and/or the like, and/or the second logical voltage may include at least one of a high logical voltage, greater than 2.5 V, greater than 3.3 V, greater than 5 V, any combination thereof, and/or the like, as described herein.

In some embodiments, first voltage regulator 504 may be configured to supply power from non-clinical power adapter 500 to the AED (e.g., AED 102) when the I/O line is set to the second logical voltage and to stop supplying power from non-clinical power adapter 500 to the AED (e.g., AED 102) when the I/O line is set to the first logical voltage, as described herein.

In some embodiments, switching element 508 may include a battery monitor circuit (e.g., a gas gauge and/or the like), as described herein. Additionally or alternatively, the battery monitor circuit (e.g., switching element 508) may be configured to disable first voltage regulator 504 by setting the I/O line to the first logical voltage, as described herein.

In some embodiments, second voltage regulator 506 may be configured to receive power (e.g., having a voltage range) from input connection 502 and to supply power having a second voltage less than the voltage range to at least one electronic component (e.g., memory 510, switching element 508, and/or the like) of non-clinical power adapter 500. For example, the second voltage may include 3.3 V.

In some embodiments, memory 510 may include an EEPROM, as described herein.

In some embodiments, memory 510 may store at least one identifier of non-clinical power adapter 500, as described herein. Additionally or alternatively, a processor (e.g., processor 182 of AED 102) may read the identifier from memory 510 to determine non-clinical power adapter 500 is electrically coupled to an electrical connector (e.g., electrical connector 170).

In some embodiments, first voltage regulator 504 may be configured to supply power having a selected voltage and a selected current. Additionally or alternatively, the selected voltage and/or the selected current may be different than a battery pack voltage or a battery pack current, respectively, of power supplied by a battery pack (e.g., battery pack 120), as described herein. For example, the selected voltage may be 12 V and the selected current may be at least one of 3 A or 5 A, and/or the battery pack voltage may be 12 V and the battery pack current may be 6.5 A.

In some embodiments, the power supply connected to input connection 502 may include a DC power supply, as described herein. Additionally or alternatively, the power supply may include a voltage converter configured to convert AC input power to DC output power, as described herein. For example, the power supply may receive AC input power (e.g., from an electrical outlet, a wall outlet, and/or the like) and/or may convert the AC input power to DC output power (e.g., approximately 12 V DC and/or the like) to be supplied to input connection 502.

In some embodiments, non-clinical power adapter 500 may supply power to an AED (e.g., AED 102) for operation in a non-clinical mode (e.g., diagnostic testing mode, configurability mode, data transfer mode, training mode, and/or the like, as described herein). In some embodiments, non-clinical power adapter 500 may be powered from a power supply (e.g., a 12 V AC-DC power supply and/or the like). Additionally or alternatively, when non-clinical power adapter 500 is connected to (e.g., powering and/or the like) the AED (e.g., AED 102), the AED may limit (e.g., reduce, eliminate, and/or prevent) charging of the capacitor(s) of the AED, as described herein. Additionally or alternatively, when non-clinical power adapter 500 is connected to (e.g., powering and/or the like) the AED (e.g., AED 102), the AED may still perform other functions (e.g., non-clinical functions and/or the like, as described herein). Additionally or alternatively, when non-clinical power adapter 500 is connected to (e.g., powering and/or the like) the AED (e.g., AED 102), the AED may perform diagnostic testing (e.g., self-testing and/or the like), such as charging the capacitor(s) of the AED to a predetermined voltage (e.g., 250 V) for the bridge testing (e.g., if the power supply is able to provide power having at least 2 A of current, at least 3 A of current, and/or the like).

In some embodiments, memory 510 (e.g., EEPROM) may be the same memory as used by a battery pack (e.g., battery pack 120) for the AED (e.g., AED 102). Additionally or alternatively, switching element 508 may be the same battery monitor circuit (e.g., gas gauge and/or the like) as used by a battery pack (e.g., battery pack 120) for the AED (e.g., AED 102).

In some embodiments, the AED (e.g., AED 102) may disable power from non-clinical power adapter 500 if non-clinical power adapter 500 is not recognized by (e.g., not compatible with) the AED, as described herein. In some embodiments, the non-clinical power adapter 500 may disable power to the AED 102 if the non-clinical power adapter 500 is not recognized (e.g., not compatible with) the AED.

In some embodiments, input connection 502 may include a DC power jack. For example, input connection 502 may include a 2.0 mm center pin jack (e.g., which may be compatible with the power supply (e.g., power supply 140)

connected thereto. In some embodiments, input connection 502 may include a transient voltage suppressor (TVS) for protection (e.g., to protect a 12 V pin thereof).

In some embodiments, second voltage regulator 506 may supply 3.3 V to power memory 510 (e.g., EEPROM) and/or switching element 508 (e.g., gas gauge). For example, second voltage regulator 506 may continuously provide power to memory 510 and/or switching element 510 (e.g., regardless of whether power from first voltage regulator 504 is enabled or disabled).

In some embodiments, first voltage regulator 504 may include a high current, low drop out voltage regulator. Additionally or alternatively, first voltage regulator 504 may provide 12 V to power the AED (e.g., AED 102). In some embodiments, first voltage regulator 504 may include an enable pin connected to the I/O line from switching element 508. In some embodiments, when voltage on the I/O line (and by connection to the enable pin) is set to a low logical voltage, power from first voltage regulator 504 may be disabled, as described herein.

In some embodiments, the output (Vout) of first voltage regulator 504 may be set based on at least one resistor (e.g., first resistor R1, second resistor R2, and/or the like). For example, the output (Vout) of first voltage regulator 504 may be set as follows:

$$R1 = R2\left(\frac{Vout}{1.24} - 1\right)$$

In some embodiments, first voltage regulator 504 may require a minimum load current (e.g., 10 mA and/or the like) to stay in regulation. In some embodiments the resistor values (e.g., first resistor R1, second resistor R2, and/or the like) may be chosen to set the output (Vout) to 12 V and provide a load current (e.g., 10.8 mA and/or the like) greater than the minimum load current (e.g., when the non-clinical power adapter 500 is installed in an AED and/or when the AED is powered off). In some embodiments, a fast acting fuse (e.g., 3 A fuse and/or the like) connected to first voltage regulator 504 may disable power to the AED in the event of a fault condition.

In some embodiments, memory 510 (e.g., EEPROM) may store data (e.g., identifier data, manufacturing data, usage data, and/or the like), as described herein. Additionally or alternatively, memory 510 may store a battery type identifier recognizable by the AED (e.g., AED 102) in a battery type identifier field, which may be read by the AED (e.g., to determine the type of battery connected thereto). In some embodiments, the battery type identifier of non-clinical power adapter 500 may identify non-clinical power adapter 500 as a non-clinical power adapter.

In some embodiments, switching element 508 (e.g., the gas gauge) may be intended to monitor available capacity in a battery pack (e.g., battery pack 120) for the AED (e.g., AED 102). Additionally or alternatively, a return path (e.g. Return) from output connection 512 and/or first voltage regulator 504 may pass through current sense resistor 516, which may be connected to switching element 508 (e.g., an input pin, current sensing pin, and/or the like of the gas gauge). This may allow for repurposing a gas gauge to be used as switching element 508. Additionally or alternatively, although non-clinical power adapter 500 does not contain any battery cells, the AED may continue to use algorithms associated with the battery pack (e.g., algorithms to adjust battery capacity based on runtime and/or the like). In some embodiments, disconnecting the power supply from non-clinical power adapter 500 (e.g., from input connection 502 thereof) may remove power from switching element 508 (e.g., the gas gauge), and the sensed battery capacity (e.g., not actual capacity, but faked capacity based on the current through current sense resistor 516) may be reset to full at next power up. In some embodiments, removing components connected to switching element 508 and/or connecting a pull-down resistor thereto may prevent runtime capacity depletion.

In some embodiments, an I/O pin of switching element 508 (e.g., gas gauge) connected to the I/O line (which may be connected to first voltage regulator 504) may be used to enable or disable the output of first voltage regulator 504. In some embodiments, the I/O pin may be an open drain pin and/or may include (e.g., have attached thereto) a pull-up resistor to set the I/O line high. Additionally or alternatively, a similar gas gauge in a battery pack (e.g., battery pack 120) for the AED (e.g., AED 102) may have a pull-down resistor connected to the I/O pin. In some embodiments, the AED (e.g., AED 102) may set this I/O pin and/or I/O line to a low logical voltage after a time interval (e.g., approximately 10 seconds and/or the like) after insertion of a battery pack (e.g., unless the AED recognizes that non-clinical power adapter 500 has been inserted and is recognized). Additionally or alternatively, if the AED determines that non-clinical power adapter 500 has been inserted and is not recognized by (e.g., compatible with) the AED, the I/O pin and/or I/O line may be set to the low logical voltage after a time interval (e.g., approximately 10 seconds and/or the like). For example, the output of first voltage regulator 504 may remain disabled until switching element 508 (e.g., gas gauge) is reset (e.g., by disconnecting the power supply from non-clinical power adapter 500 and/or input connection 502 thereof). Additionally or alternatively, if the AED determines that non-clinical power adapter 500 has been inserted and is recognized by (e.g., compatible with) the AED, the I/O pin and/or I/O line may be maintained at and/or set to a high logical voltage, and/or the output of first voltage regulator 504 may remain enabled (e.g., to power the AED).

Referring now to FIGS. 6A-6G, FIGS. 6A-6G show example diagrams of assembly of a non-clinical power adapter for an AED. In some embodiments, the non-clinical power adapter depicted in FIGS. 6A-6G may be the same as or similar to non-clinical power adapter 130 and/or non-clinical power adapter 500. In some non-limiting embodiments, the non-clinical power adapter may include circuit board 652, fastener 654, first adhesive fastener 656, support bracket 658, second adhesive fastener 660, recessed area 662, protrusions 663, tooling holes 664, protrusion 665, hole 666, elongated hole 667, alignment pin 668, protrusion 670, indentation 672, snap hook 674, top cover 676, indentation 678, bottom enclosure 680, barcode label 682, and/or main label 684.

In some embodiments, a power adapter housing may include bottom enclosure 680 and top cover 676. Additionally or alternatively, circuit board 652 may include electronic components, such as an input connection (e.g., input connection 502) to receive power from a power supply, at least one voltage regulator (e.g., first voltage regulator 504, second voltage regulator 506, and/or the like), an output connection (e.g., output connection 512) configured to connect to an electrical connector (e.g., electrical connector 170 of AED 102), any combination thereof, and/or the like, as described herein. In some embodiments, support bracket 658 may support circuit board 652 within the power adapter housing (e.g., within bottom enclosure 680 and top cover 676). For example, second adhesive fastener 660 may connect circuit board 652 to support bracket 658. Additionally or alternatively, first adhesive fastener 656 may connect circuit board 652 to top cover 676.

In some embodiments, as shown in FIG. 6A, first adhesive fastener 656 (e.g., a double-sided adhesive fastener and/or the like) may be attached to circuit board 652. For example, first adhesive fastener 656 may include an annular double-sided adhesive fastener, and/or a first side of first adhesive fastener 656 may be attached to circuit board 652 surrounding fastener 654 (e.g., hex nut 654 and/or the like).

In some embodiments, as shown in FIG. 6B, second adhesive fastener 660 (e.g., a double-sided adhesive fastener and/or the like) may be attached to recessed area 662 of support bracket 658. For example, a first side of second adhesive fastener 660 may be attached recessed area 662 of support bracket 658. Additionally or alternatively, support bracket 658, when attached to circuit board 652, may be proximate to and/or may at least partially surround protrusion 665.

In some embodiments, as shown in FIG. 6C, support bracket 658 may be attached to circuit board 652. For example, the first side of second adhesive 660 may be attached to support bracket 658, and a second side of second adhesive 660 may be attached to circuit board 652. In some embodiments, circuit board 652 may include at least one first alignment feature (e.g., tooling holes 664), and/or support bracket 658 may include at least one second alignment feature (e.g., protrusions 663) corresponding to the first alignment feature(s). For example, tooling holes 664 may be defined in circuit board 652, and/or protrusions 663 may be configured to be received by tooling holes 664.

In some embodiments, as shown in FIG. 6D, circuit board 652 (with support bracket 658 attached thereto) may be attached to top cover 676. For example, the first side of first adhesive fastener 656 may be attached to circuit board 652, and a second side of first adhesive fastener 656 may be attached to circuit board top cover 676. In some embodiments, circuit board 652 may include at least one alignment feature (e.g., hole(s) 666, elongated hole(s) 667, protrusion 670, and/or the like), and/or top cover 676 may include at least one corresponding alignment feature (e.g., alignment pin 668, snap hook 674, indentation 672, and/or the like, respectively) corresponding to the alignment feature(s) of circuit board 652. For example, circuit board 652 may include hole(s) 666 and top cover 676 may include alignment pin(s) 668 configured to be received in the hole(s) 666. Additionally or alternatively, circuit board 652 may include elongated hole(s) 667 and top cover 676 may include snap hooks(s) 674 configured to be received in elongated hole(s) 667. Additionally or alternatively, circuit board 652 may include protrusion 670 and top cover 676 may include indentation 672 configured to receive protrusion 670.

In some embodiments, as shown in FIG. 6E, bottom enclosure 680 may include an alignment feature (e.g., indentation 678) and top cover 676 may include another alignment feature (e.g., indentation 672) corresponding to the alignment feature of bottom enclosure 680. For example, indentation 672 may be configured to align with indentation 678 and/or the like.

Figure 6G:
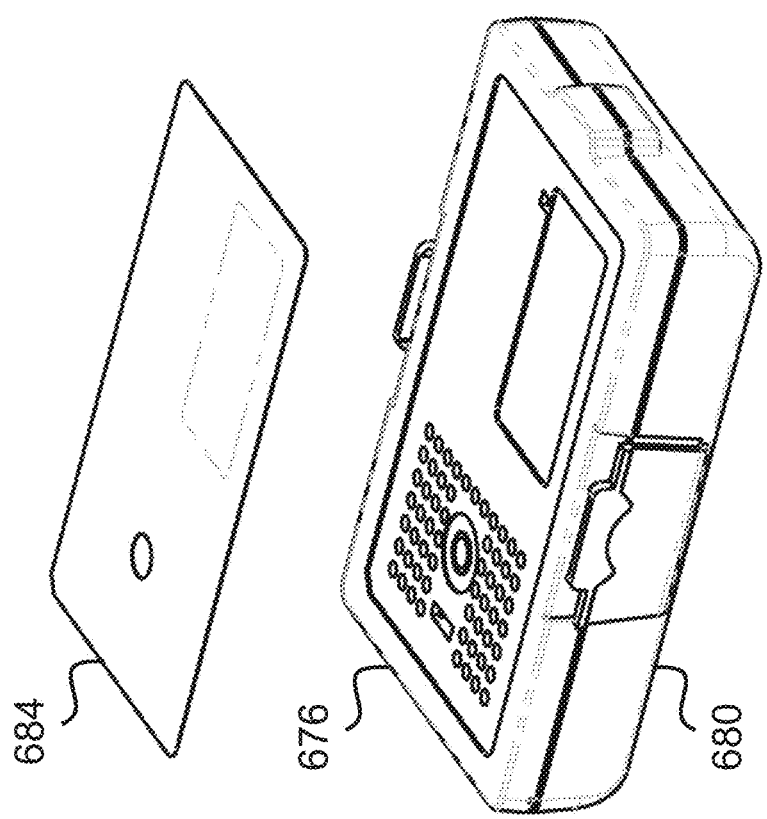
Figure 6F:
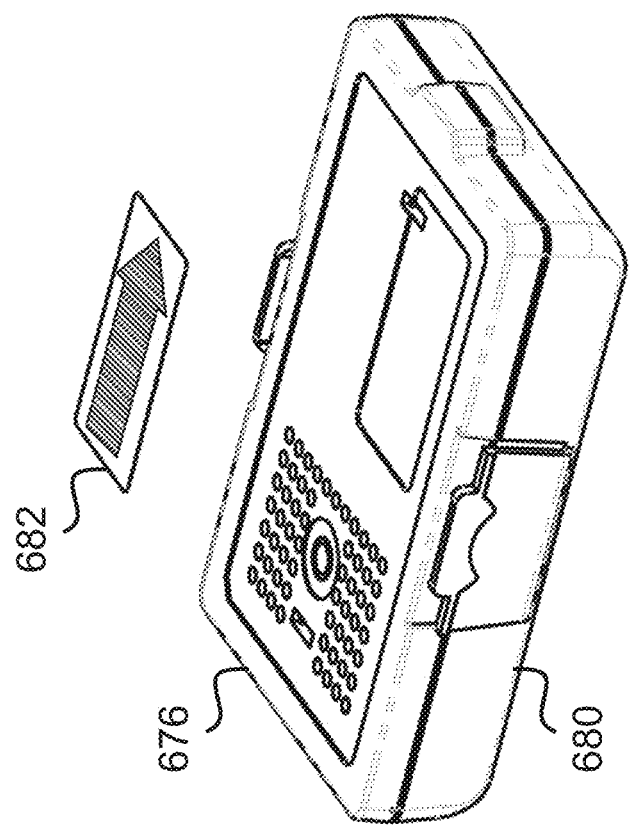
Figure 7A:
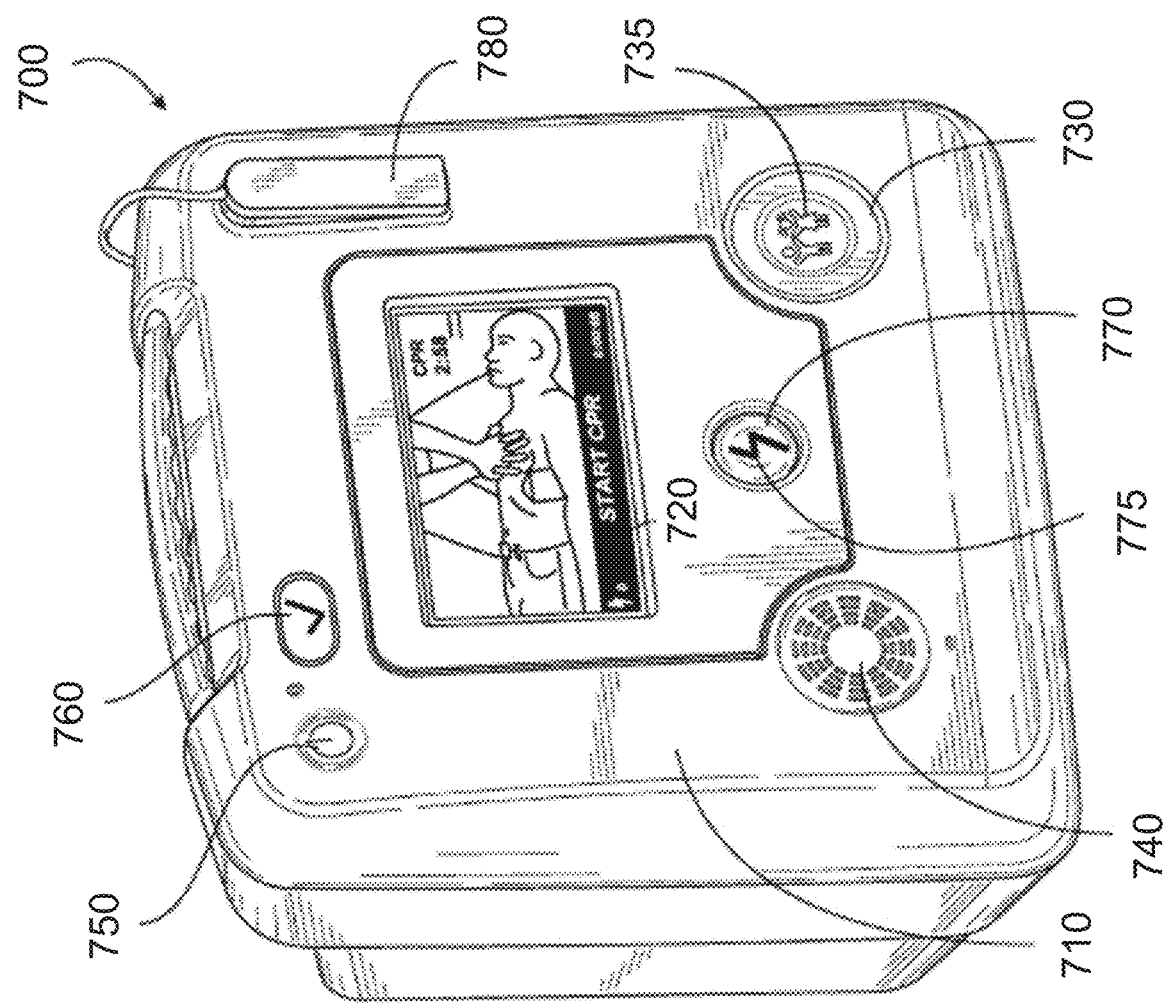
Figure 7B:
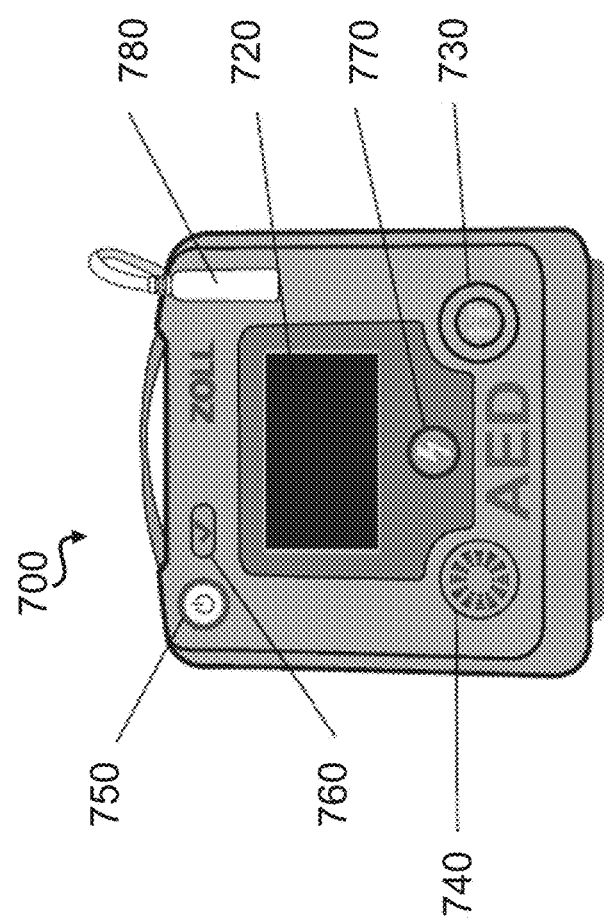
Figure 7C:
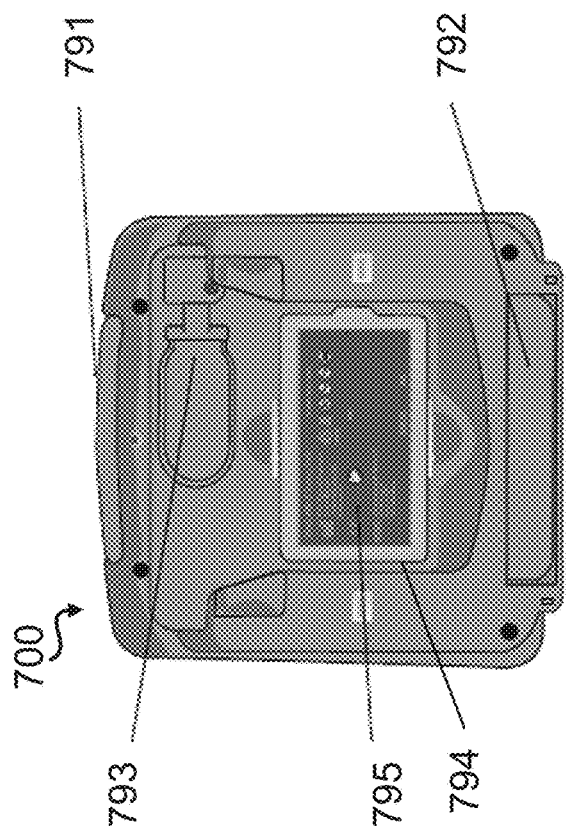
Figures 7D, 7E:
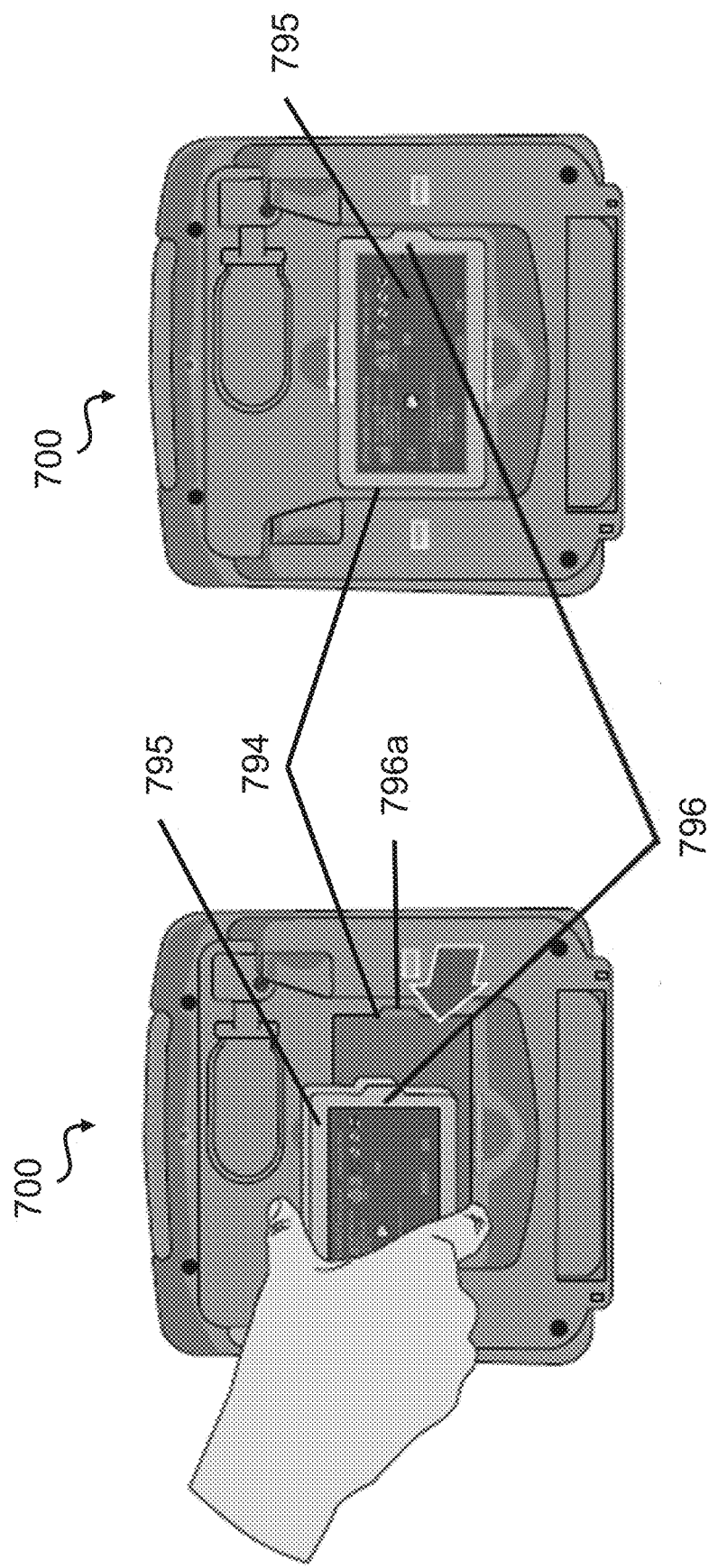
Figure 7I:
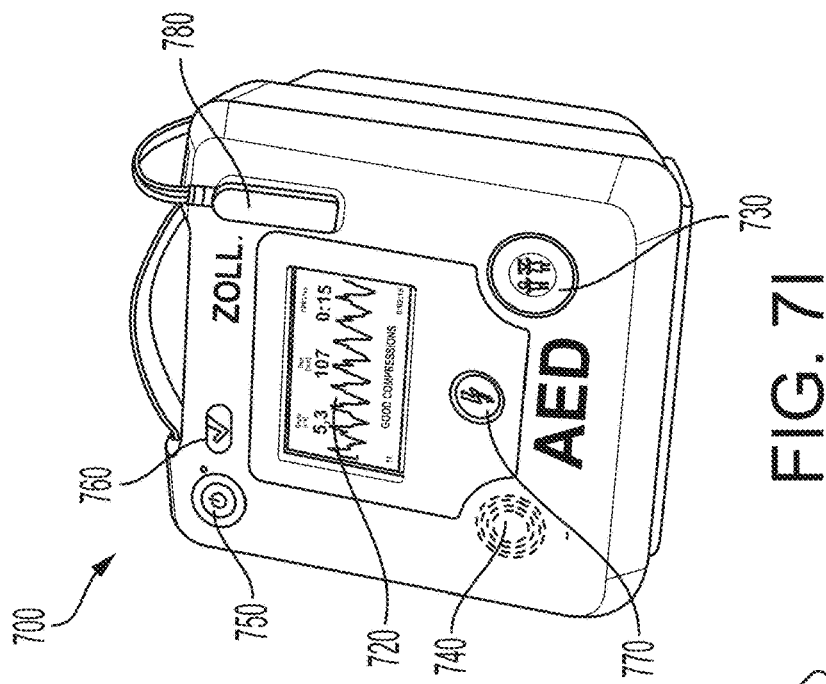
Figure 7H:
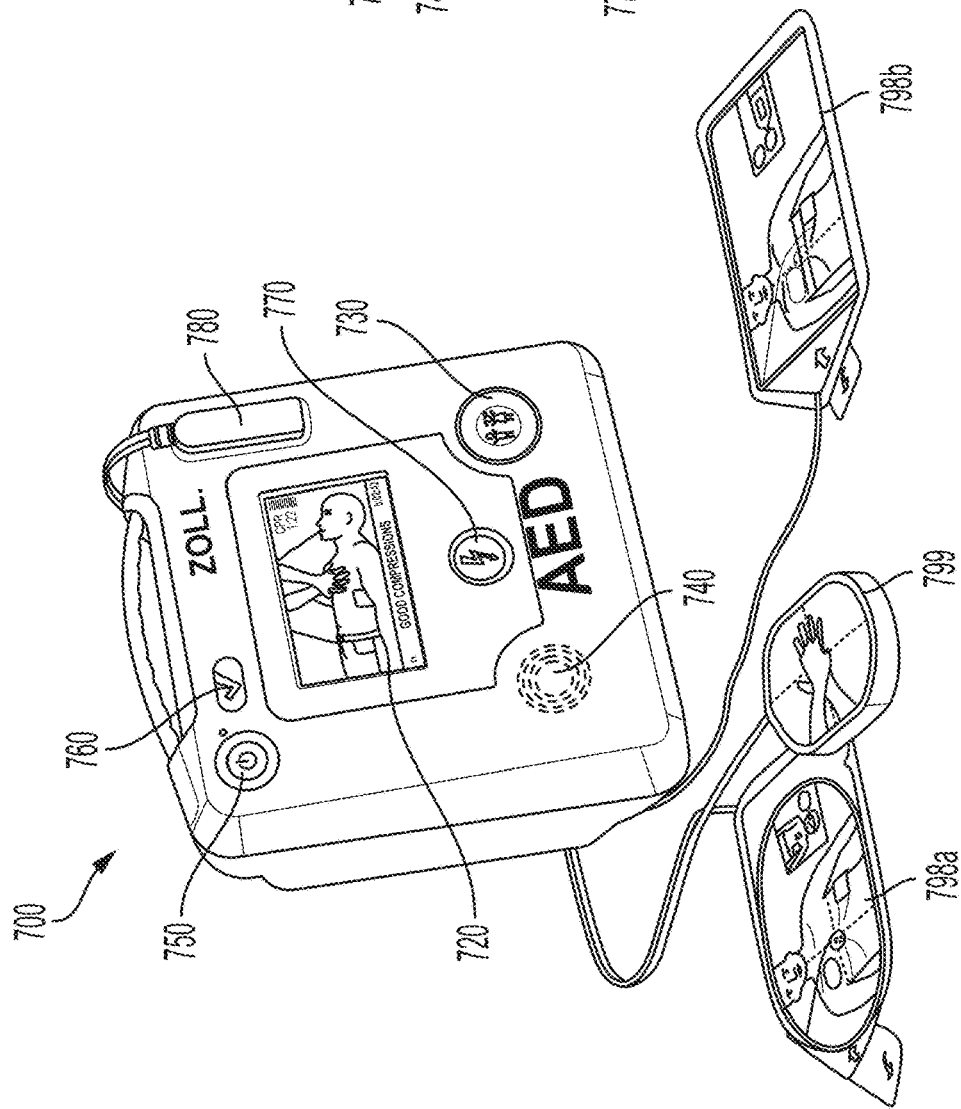

In some embodiments, as shown in FIG. 6F, barcode label 682 may be configured to be affixed to (e.g., attached by adhesive to and/or the like) top cover 676. Additionally or alternatively, as shown in FIG. 6G, main label 684 may be configured to be affixed to (e.g., attached by adhesive to and/or the like) top cover 676.

Referring now to FIGS. 7A-7I, FIGS. 7A-7I show example diagrams of an AED 700 and/or a non-clinical power adapter 797 therefor. In some embodiments, AED 700 may be the same as or similar to AED 102. In some embodiments, non-clinical power adapter 797 may be the same as or similar to non-clinical power adapter 130, non-clinical power adapter 500, and/or the non-clinical power adapter depicted in FIGS. 6A-6G.

In some embodiments, AED 700 may be capable of operating in a pediatric operating mode and an adult operating mode. AED 700 may have a housing 710, which may house and/or protect the internal components of AED 700. For example, housing 710 may be constructed to provide one or more inputs and outputs, which may include a user interface. The user interface may include a graphical display 720 which can display instructions, treatment feedback, and other information to a user which may be useful for administering resuscitative therapy (e.g., electrotherapy, CPR, and/or the like), and/or for other non-clinical and/or training features.

In some embodiments, the user interface of AED 700 may include a control 730 for changing the operating mode of AED 700. For example, control 730 may switch the operating mode between an adult operating mode and a pediatric operating mode. In some embodiments, control 730 may provide the ability for AED 700 to switch between adult and pediatric operating modes dynamically during the resuscitation process. The resuscitation process may include various activities performed and/or treatments delivered to a patient during the course of resuscitation (e.g. determining the patient's state of consciousness, contacting a local emergency number, placing electrodes on the patient, analyzing the patient's ECG, detecting a shockable rhythm, delivering a defibrillation shock, performing CPR, etc.). For example, as the rescuer begins resuscitative therapy, AED 700 may be set to adult operating mode by default; however, it might not be until further into the resuscitation process that the rescuer recognizes that AED 700 should be switched to the pediatric operating mode. Accordingly, the rescuer may switch AED 700 setting from adult operating mode to pediatric operating mode at any time during the resuscitation process, and AED 700 may be able to instantly accommodate the switch and seamlessly continue instructions for the resuscitative process.

In some embodiments, AED 700 may have an indicator 735 for providing to the user an indication (e.g., illumination, audible sound, display, etc.) of the current operating mode in use.

In some embodiments, AED 700 may include speaker 740. For example, speaker 740 may provide auditory instructions and/or other feedback to a user during treatment.

In some embodiments, AED 700 may include a switch 750 for turning AED 700 into an on or off state. Additionally or alternatively, AED 700 may include a readiness indicator 760 which may report (e.g., indicate) whether AED 700 needs maintenance or other repair such that it is unfit for current use.

In some embodiments, AED 700 may include control 770 (e.g., a button, switch, and/or the like) for activating treatment (e.g., electrotherapy, a defibrillating shock and/or the like). For example, control 770 may include a shock button.

In some embodiments, AED 700 may include electrode connector 780. For example, electrode connector 780 may receive signals from sensors (e.g., electrodes 798*a* and 708*b*, chest compression sensor 799, and/or the like), e.g., regarding one or more physiological parameters of the patient. Such physiological parameters (e.g., ECG signal) may be analyzed by the processor according to an appropriate algorithm to make a determination of whether a defibrillating shock should be administered to the patient. Additionally or alternatively, electrode connector 780 may communicate signals such as a defibrillating shock. For example, a cable leading to defibrillating electrodes 798*a* and 798*b* may be interfaced with the electrode connector 780.

In some embodiments, AED 700 may include several internal components that enable the AED to be used for defibrillation of multiple kinds of patients. Additionally or alternatively, AED 700 may include a processor (e.g., computer processor and/or the like) as described herein. For example, the processor may be configured to determine in which operating mode the AED should be delivering treatment.

In some embodiments, the processor may be configured to determine whether adult electrodes (e.g., electrodes 798*a* and 798*b* and/or the like) are connected to electrode connector 780 and subsequently ensure that the operating mode of the AED is in the adult operating mode. For example, if adult-specific electrodes (e.g., CPR-D-Padz®, CPR Stat-Padz®, and/or Stat-Padz® provided by ZOLL Medical Corp. and/or the like) are connected to AED 700 (e.g., electrode connector 780 thereof), the processor may sense that adult-specific electrodes are being employed and deactivate the control 730 that would otherwise allow a user to switch AED 700 from adult operating mode to pediatric operating mode. Additionally or alternatively, if AED 700 is set to pediatric operating mode and adult-specific electrodes are connected to AED 700, the processor may then automatically switch the AED to adult operating mode.

In some embodiments, the processor may be configured to determine whether pediatric electrodes (e.g., electrodes 798*a* and 798*b* and/or the like) are connected to the electrode connector 780 and subsequently change the operating mode to the pediatric operating mode. For example, if pediatric-specific electrodes (e.g., Pedi-Padz® provided by ZOLL Medical Corp. and/or the like) are connected to AED 700, the processor may determine that pediatric-specific electrodes are being employed and automatically switch the AED from adult operating mode to pediatric operating mode. Additionally or alternatively, the processor may also deactivate the control 730 so that a user is unable to switch the AED from pediatric operating mode to adult operating mode as long as the pediatric-specific electrodes are connected thereto. In some embodiments, when the pediatric-specific electrodes are connected, the processor may also transmit a signal so that the indicator 735 provides an indication to the user that the AED is in pediatric operating mode.

In some embodiments, the processor may be configured to determine whether the electrode assembly connected to the electrode connector 780 is capable of both pediatric and adult treatment (e.g., Uni-Padz® provided by ZOLL Medical Corp. and/or the like) and/or to enable the operating mode to be changed using control 730. Additionally or alternatively, when the electrode assembly configured for both adult and pediatric treatment is connected to AED 700 (e.g., electrode connector 780 thereof), the processor may recognize this capability and allow the control 730 to toggle between adult and pediatric operating mode at any point during resuscitation.

In some embodiments, the internal components of AED 700 (e.g., in addition to the processor and/or the like) may include one or more capacitors. For example, the capacitors can be charged during use of AED 700. Additionally or alternatively, the capacitors can be quickly discharged though an external electrode assembly (e.g., electrodes 798*a* and 798*b* and/or the like), interfaced with AED 700 via the electrode connector 780, to provide a therapeutic electric shock. In some embodiments, the capacitors can discharge in such a way as to correctly deliver an appropriate electric shock having a desired level of energy (e.g., pre-configuration default set to 120-200 J for an adult patient, 50-85 J for a pediatric patient, and/or the like) to the patient during treatment. Additionally or alternatively, the capacitors can provide electric shock to the patient at different levels of intensity/energy. For example, the levels of intensity/energy can be controlled by the processor. In some embodiments, the energy configuration of AED 700 may change between adult and pediatric modes, for example, by changing the energy level of the defibrillation shock, by controlling the average current delivered during the defibrillation shock, and/or the like. Additionally or alternatively, the energy configuration of AED 700 may be mode-specific, e.g., depending on whether the AED is in the adult operating mode or the pediatric operating mode. For example, the level of defibrillation shock energy may be based on the amount of stored charge provided to the capacitors via a charging current or voltage. For example, when storing charge for a defibrillating shock, a greater amount of charge may be stored within the capacitor(s) when AED 700 is set to adult operating mode as compared to when AED 700 is set to pediatric operating mode. In some embodiments, once the capacitor(s) are sufficiently charged, the stored charge may be at least partially discharged (e.g., by the presence of discharge circuits, resistors, other dissipating elements, and/or the like, which may be located between the capacitor(s) and the defibrillating electrode(s) 798*a* and 798*b*, so as to reach the desired level of defibrillation shock energy. For example, a greater resistance may be provided upon discharge when AED 700 is set to pediatric operating mode as compared to when AED 700 is set to adult operating mode, to reduce the total energy delivered during a therapeutic shock than would otherwise be the case. In some embodiments, the user may configure the defibrillation shock energy, as described herein. In some embodiments, the defibrillation shock energy can be determined by the operating mode of the AED, as described herein. In some embodiments, the defibrillation current delivered to the patient may be controlled during shock delivery to deliver a current sufficient for defibrillating a pediatric patient versus that sufficient to defibrillate an adult patient, as described herein.

In some embodiments, in addition to changing the energy configuration of AED 700 between an adult and pediatric operating mode, the analysis configuration may also be different in the two different modes. For example, AED 700 may exhibit mode-specific analysis configurations, e.g., depending whether AED 700 is in an adult operating mode or a pediatric operating mode. For example, in the pediatric operating mode, a shock analysis algorithm specific for pediatric patients may be used. The pediatric shock analysis algorithm may be calibrated to analyze a child's ECG signal (e.g., rather than an adult's EGC signal) such that AED 700 may make a more accurate determination of whether a shock should be delivered to the pediatric patient. In some embodiments, AED 700 may measure the ECG baseline content, QRS rate, width and variability, amplitude, temporal regularity, and/or the like and determine whether a shockable rhythm exists. For example, for a pediatric patient, one or more of the measured values may be different for a shockable rhythm than for the adult patient. Additionally or alternatively, in the pediatric operating mode, analysis of data from chest compression sensors and/or ventilation sensors may be adapted for pediatric patients.

In some embodiments, each operating mode of AED 700 may include various configurations of the AED for delivering treatment. For example, the configuration(s) may include hardware settings, software settings, characteristics of treatment, selection of instructions to be delivered to the user, or any other setting which changes functionality of AED 700. In some embodiments, the operating mode of AED 700 may be the configuration which optimizes the AED to deliver treatment to a particular type of patient. For example, types of patients may include adult patients, pediatric patients, and/or the like. In some embodiments, AED 700 may be optimized in a number of ways. For example, the user configuration parameters may be changed between the pediatric and adult operating modes such that the instructions on display 720 are adjusted for each stage of treatment to be relevant to a pediatric patient when AED 700 is operating in pediatric operating mode, or relevant to an adult patient when AED 700 is operating in the adult operating mode. In some embodiments, the adult operating mode may be set to the default user configuration, which may be modified for a pediatric patient when the pediatric operating mode is enabled.

In some embodiments, the level of the electric shock delivered can be changed.

In some embodiments, in addition to adult and pediatric operating modes, which may be examples of clinical modes related to treatment of a patient, AED 700 may operate in other non-clinical modes and/or sub-modes, which may be related non-treatment functionality such as configuration, diagnostics, training, and/or the like, as described herein. For example, AED 700 may operate in a battery mode, a basic configuration mode (e.g., intended for basic life support personnel), an advanced configuration mode (e.g., intended for advanced life support personnel), a training mode, and/or the like, as described herein. For the purpose of illustration, battery mode may be a mode where AED 700 tests a new battery pack inserted into AED 700. In some embodiments, AED 700 may operate in a fully-automatic mode wherein the AED automatically delivers shock therapy treatment to a patient without waiting for input from the user to deliver the shock. Additionally or alternatively, AED 700 may operate in a semi-automatic mode wherein AED 700 may wait for user input to deliver the shock, such as the press of control 770 (e.g., a shock button), before AED 700 delivers shock therapy treatment to a patient. In some embodiments, other sub-modes may include one or more professional modes (e.g., for basic or advanced life support personnel), a non-professional mode (e.g. a lay rescuer mode), and/or the like. In some embodiments, when operating in one or more of the professional modes (e.g., basic life support mode), for example, AED 700 may display different information to the user who is presumed to be a more sophisticated user than a typical user. For example, professional mode may include more feedback regarding the quality of CPR administered to the patient and fewer instructions than in the non-professional mode. In some embodiments, AED 700 can initialize to either a professional mode or non-professional mode by default, depending on pre-configured user settings. For example, the user may desire to configure AED 700 to initialize in professional mode for various reasons, such as location of AED 700 (e.g., close proximity to basic life support professionals) and/or the intended user of the particular AED 700. Additionally or alternatively, the professional mode may be called a basic life support mode. In some embodiments, the professional mode may be a sub-mode of the adult or pediatric operating modes, such that when AED 700 is in adult operating mode, AED 700 can operate in a professional mode or non-professional mode. Additionally or alternatively, when AED 700 is in pediatric operating mode, AED 700 may operate in a professional mode or non-professional mode.

In some embodiments, various resuscitative treatments may include, for example, any stage required for the defibrillation and/or care of a patient using AED 700, such as initializing AED 700, preparing the electrode assembly (e.g., electrodes 798*a* and 798*b*, chest compressions sensor 799, and/or the like) for use, affixing the electrode assembly (e.g., electrodes 798*a* and 798*b*, chest compressions sensor 799, and/or the like) to the patient, measuring vitals of the patient, applying an electric shock, performance and analysis of CPR, and so on.

In some embodiments, housing 710 of AED 700 may house and protect the internal components of AED 700. In some embodiments, the corners of AED 700 (e.g., the corners of housing 710) may be rounded, truncated, beveled, and/or otherwise structured so that the housing 710 is free of sharp edges and, hence, may be easy and safe for a person to handle. In some embodiments, a handle 791 may be attached to housing 710 for AED 700 to be comfortably and conveniently carried. Various input and output components of AED 700 can be included with (e.g., flush with, embedded in, and/or the like) the exterior of housing 710 (e.g., such that the exterior of housing 710 has a smooth and/or sleek feel and/or appearance). For example, the control 730, speaker 740, power button 750, and communication port 793 (e.g., USB port and/or the like) may be seated in housing 710 such that they do not protrude outward from the exterior of housing 710 (e.g., are flush with the exterior of housing 710, form depressed features relative to the exterior of housing 710, and/or the like).

In some embodiments, housing 710 may be constructed from any suitable material(s), such as plastic and/or other rigid material(s). In some embodiments, the color(s) of housing 710 may be chosen such that a colorblind user can distinguish labels marking AED 700 as such from housing 710. In some embodiments, the color(s) of housing 710 may be chosen to soothe the user and/or to avoid colors which may induce stress in the user, such as bright red (e.g., a characteristic color of warning signs and labels and/or the like). In some embodiments, color(s) of housing 710 may be chosen such that AED 700 may be recognizable and distinguishable from other medical devices (e.g., which tend to be white, black, and/or gray). For example, the colors of housing 710 may be green-yellow, and/or a label indicating that the device is an AED may be blue.

In some embodiments, AED 700 may have a user interface which includes display 720. For example, display 720 may include a full-color screen, such as an LED-backlit screen, a touchscreen, any combination thereof, and/or the like. In some embodiments, display 720 may be covered by a touch-sensitive film and/or may include other touch sensitive device(s) such that display 720 may have touch-screen functionality. In some embodiments, display 720 may be used to show instructions for treatment, warnings, a status of AED 700, and/or other information which may be relevant to treatment of the patient in a clinical operating mode and/or relevant to non-clinical operating modes. In some embodiments, display 720 may show still images of instructions for treatment. Additionally or alternatively, display 720 may show animated instructions for treatment. In some embodiments, display 720 may show real-time or near real-time feedback, measurements, any combination thereof, and/or the like based on signals provided from the electrode assembly (e.g., electrodes 798*a* and 798*b* and/or the like), other sensors (e.g., chest compression sensor 799 and/or the like), inputs of AED 700, any combination thereof, and/or the like.

In some embodiments, AED 700 may have a control 730, which may be used to change the operating mode, e.g., to or from pediatric operating mode or adult operating mode. For example, control 730 may be easily manipulated by the user to change the operating mode of AED 700 during use of AED 700. In some embodiments, control 730 may be used to change the operating mode of AED 700 at any time during use of AED 700 and/or during the resuscitation process. For example, control 730 may include a button. In some embodiments, when the button is depressed by the user, AED 700 may change its operating mode (e.g., to or from pediatric operating mode or adult operating mode). For example, the button may dynamically toggle AED 700 between an adult operating mode and a pediatric operating mode. In some embodiments, if electrodes 798*a* and 798*b* are only capable of one kind of operating mode, then control 730 may be disabled from changing the operating mode. In some embodiments, control 730 may include other types of controls, for example, a switch, touch screen activation, and/or other suitable method.

In some embodiments, indicator 735 may provide an indication to the user as to the current mode of operation of the AED 700. For example, indicator 735 may include any method of signaling to the user what the current mode of operation is such that the user may perceive the mode of operation at any time during treatment. In some embodiments, indicator 735 may be such that if the user approaches a scene of treatment after treatment has already begun, the user can immediately (e.g., with little to no delay) determine in which mode of operation the AED is currently operating. For example, as shown, indicator 735 may be located on control 730 and/or may be a part of the control 730. For the purpose of illustration, indicator 735 may be provided as a pediatric symbol and may be located directly on control 730. Additionally or alternatively, when control 730 is activated (e.g., the button is depressed and/or the like) during use of AED 700, indicator 735 may illuminate to show that the AED is operating in the pediatric operating mode. For example, indicator 735 may be illuminated whenever AED 700 is operating in pediatric operating mode. Additionally or alternatively, indicator 735 may remain free of illumination (e.g., may be turned off) whenever AED 700 is operating in the adult operating mode. As such, if there are two modes of operation, the illumination of indicator 735 or the lack of illumination of indicator 735 may be an immediate indication of the operating mode currently in use. In some embodiments, indicator 735 may include a visual indicator such as illumination of the pediatric symbol, an audio indicator such as a tone from speaker 740, a lighted display such as display 720, a verbal indicator such as a verbal instruction from the speaker 740, a haptic indicator such as a dial, switch, or other haptic indicator, and/or any other suitable manner of indication.

In some embodiments, each mode of operation for AED 700 may be different from other modes of operation. For example, a mode of operation can have one or more of a mode-specific series of instructions (e.g. instruction to a user for different stages of treatment), prompts, display images, and/or treatment measurements, as described herein. Additionally or alternatively, each mode (e.g., each clinical mode) of operation may have a treatment regimen which is appropriate for a particular class of patient. For example, AED 700 may have an adult operating mode which is used for adult patients, a pediatric operating mode which is used for pediatric patients, any combination thereof, and/or the like.

In some embodiments, the adult operating mode may be used for treatment of adult patients and/or may include a user configuration adapted for the resuscitation of adult patients. For example, display 720 of AED 700 may provide instructions and feedback information which is suitable for treatment of the adult patient, as described herein. In some embodiments, during the adult operating mode of operation, display 720 may show instructions for treatment of the adult patient with AED 700. For example, display 720 may show instructions for preparing the adult patient for treatment, placing the electrode assembly (e.g., electrodes 798a and 798b and/or chest compression sensor 799) on the adult patient, performing CPR on the adult patient, shocking the adult patient when appropriate, any other stages of treatment, relevant feedback from the electrode assembly for each of these stages, any combination thereof, and/or the like.

In some embodiments, the pediatric operating mode may be used for treatment of pediatric patients and/or may include a user configuration adapted for the resuscitation of pediatric patients. For example, the display 720 of AED 700 may provide instructions and feedback information which is suitable for treatment of pediatric patient. In some embodiments, during the pediatric operating mode of operation, display 720 may show instructions for treatment of the pediatric patient with AED 700. For example, display 720 may show instructions for preparing the pediatric patient for treatment, placing the electrode assembly (e.g., electrodes 798a and 798b and/or chest compression sensor 799) on the pediatric patient, performing CPR on the pediatric patient, shocking the pediatric patient when appropriate, relevant feedback from the electrode assembly for each of these stages, any combination thereof, and/or the like.

In some embodiments, e.g., in addition to having a mode-specific series of images on display 720 for each mode of operation, AED 700 may perform treatment which is suitable for a particular patient. For example, when operating in the adult operating mode, AED 700 may perform treatment which is suitable for an adult patient but might not be suitable for a pediatric patient. For example, the level of electric shock set by AED 700 may be higher for treatment of an adult patient than the level of electric shock set by AED 700 for treatment of a pediatric patient. In some embodiments, AED 700 system may be configured to provide escalating rectilinear biphasic defibrillation energies in varying amounts depending on whether AED 700 is set to the adult operating mode or the pediatric operating mode. For example, when set to adult operating mode, in the clinical configuration/mode, the respective defibrillation energies provided by AED 700 may be 120 J for the first defibrillation shock, 150 J for the second defibrillation shock and 200 J for the third defibrillation shock. Additionally or alternatively, when set to pediatric operating mode, the respective defibrillation energies provided by AED 700 may be 50 J for the first defibrillation shock, 70 J for the second defibrillation shock and 85 J for the third defibrillation shock. In some embodiments, for adult or pediatric operating modes, defibrillation energies provided by AED 700 may be set according to pre-configured defaults and/or may be set by a user via configuration of AED 700 during a non-clinical mode. For example, the user may configure AED 700 to deliver therapeutic shocks at energy levels other than those noted above, for the adult operating mode and/or pediatric operating mode.

In some embodiments, AED 700 may be configured to apply a defibrillating shock according to a rectilinear biphasic waveform, such as those administered by defibrillators provided by ZOLL Medical Corp. For example, depending on the mode to which the AED is set (e.g., adult operating mode or pediatric operating mode) and how the defibrillation(s) may be escalated (e.g., first, second, third shock), the rectilinear biphasic waveform may be administered so as to exhibit an appropriate level of therapeutic energy to the patient. In some embodiments, illustrative examples of electrotherapy circuits that may be suitable for administering a rectilinear biphasic waveform in accordance with the present disclosure are described in U.S. Pat. No. 5,733,370, entitled "Electrotherapy circuit and method for producing therapeutic discharge waveform immediately following sensing pulse," which is incorporated by reference herein in its entirety.

In some embodiments, illustrative examples of an AED that may be suitable for AED 700 in accordance with the present disclosure are described in U.S. Pat. No. 10,300,293, entitled "Pediatric and Adult Defibrillator," which is incorporated by reference herein in its entirety.

In some embodiments, AED 700 may include at least one communication port 793. For example, communication port 793 may include a USB port, an Ethernet port, an optical port, a coaxial port, an infrared port, any combination thereof, and/or the like. Additionally or alternatively, communication port 793 may enable AED 700 (e.g., the processor thereof) to communicate with at least one external device, as described herein.

In some embodiments, AED 700 may include at least one wireless communication interface. For example, the wireless communication interface may include a radio frequency (RF) interface, a USB interface, a Wi-Fi® interface, a Bluetooth® interface, a Zigbee® interface, a cellular network interface, and/or the like. Additionally or alternatively, the wireless communication interface may enable AED 700 (e.g., the processor thereof) to communicate with at least one external device, as described herein.

In some embodiments, housing 710 of AED 700 may device a cavity 794. For example, cavity 794 may be configured to receive battery pack 795 (e.g., may be sized and/or shaped to receive battery pack 795). Additionally or alternatively, non-clinical power adapter 797 may be configured to be received by cavity 794 (e.g., may be sized and/or shaped to be received by cavity 794). In some embodiments, cavity 794 may have an electrical connector therein. For example, the electrical connector may be configured to receive battery pack 795, as described herein. Additionally or alternatively, the non-clinical power adapter 797 may be configured to be received by the electrical connector, as described herein.

In some embodiments, battery pack 795 may include a first alignment feature and cavity 794 may include a second alignment feature corresponding to the first alignment feature. For example, the first alignment feature may include protrusion 796, and the second alignment feature may include indentation 796a, which may be configured to receive protrusion 796. Additionally or alternatively, non-clinical power adapter 796 may have a third alignment feature corresponding to the second alignment feature. For example, the third alignment feature may include protrusion 797b, which may be configured to be received by indentation 796a.

In some embodiments, power supply 797*a* may be configured to supply power to non-clinical power adapter 797, as described herein. For example, power supply 797*a* may include a DC power supply, as described herein. Additionally or alternatively, power supply 797*a* may include a voltage converter configured to convert AC input power to DC output power, as described herein.

In some embodiments, AED 700 may include carrying handle 791, as described herein. Additionally or alternatively, AED 700 may include support bar 792.

Figures 8A, 8B:
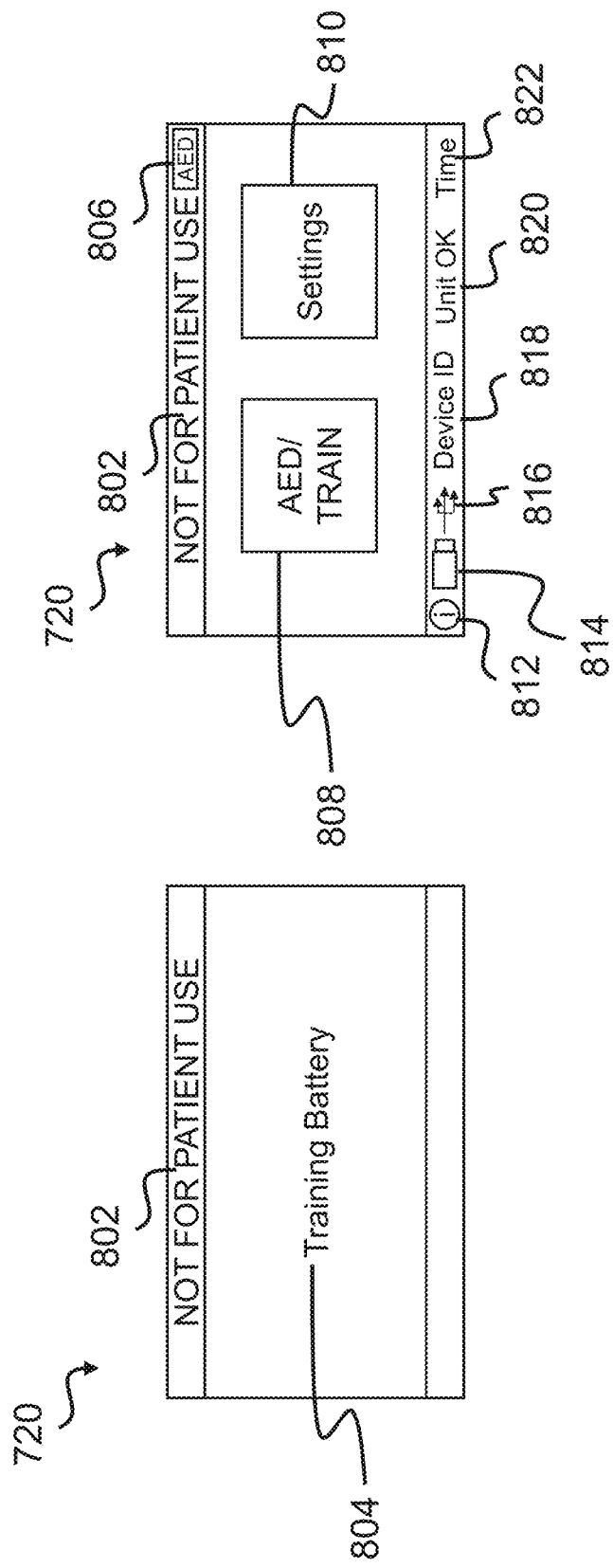
FIGS. 8A and 8B show example screenshots of a graphical user interface for display on an automated external defibrillator, according to some embodiments.

Referring now to FIGS. 8A and 8B, FIGS. 8A and 8B show example screenshots of a graphical user interface (GUI) for display on an AED. In some embodiments, the GUI may be displayed on a display (e.g., display 106, display 720, and/or the like).

In some embodiments, display 720 may display message 802 indicating that AED 700 is not for clinical use. For example, a processor of AED 700 may cause display 720 to display message 802 indicating that AED 700 is not enabled for clinical use, e.g., in response to determining that non-clinical power adapter 797 is electrically coupled to AED 700 (e.g., an electrical connector thereof).

In some embodiments, display 720 may display message 804 indicating that AED 700 is in a training mode. For example, a processor of AED 700 may cause display 720 to display message 804 indicating that AED 700 is in a training or non-clinical mode in response to determining that non-clinical power adapter 797 is electrically coupled to AED 700 (e.g., an electrical connector thereof). Additionally or alternatively, a processor of AED 700 may cause display 720 to display message 804 indicating that AED 700 is in a training or non-clinical mode in response to determining that a user selected a control (e.g., a graphical icon, such as second graphical button 808 and/or the like) to enter a clinical mode when non-clinical power adapter 797 is electrically coupled to AED 700 (e.g., an electrical connector thereof)

In some embodiments, a management screen (e.g., initial screen, home screen, operating mode selection screen, and/or the like) of the GUI displayed by display 720 (e.g., upon startup of AED 700, when non-clinical power adapter 797 is electrically coupled to AED 700, and/or the like) may include a plurality of graphical elements (e.g., messages, icons, indicators, and/or the like). For example, such graphical elements may include first graphical button 806, second graphical button 808, third graphical button 810, information icon 812, battery icon 814, USB icon 816, device identifier 818, display message 820, time indicator 822 and/or the like. For the purpose of illustration, first graphical button 806 and/or second graphical button 808 (e.g., when selected by a user) may cause AED 700 to enter a clinical mode (e.g., when battery pack 795 is connected to the electrical connector of AED 700) and/or a training or non-clinical mode (e.g., when non-clinical power adapter 797 is connected to the electrical connector of AED 700). Additionally or alternatively, third graphical button 810 (e.g., when selected by a user) may cause AED 700 to enter a configurability mode (e.g., for configuring settings of AED 700). In some embodiments, information icon 812 (e.g., when selected by a user) may cause display 720 to display information, such as expiration dates of electrodes 798*a* and 798*b*, expiration date of battery pack 795, expiration date of non-clinical power adapter 797, and/or the like. In some embodiments, battery indicator 814 may indicate remaining battery life (e.g., of battery pack 795). In some embodiments, device identifier 818 may include an identifier (e.g., unique identifier, model number, serial number, any combination thereof, and/or the like) of AED 700. In some embodiments, display message 820 may include an indication of the status of AED 700 and/or the like). In some embodiments, time indicator 822 may indicate a current time and/or the like.

Referring now to FIGS. 9A-9K, FIGS. 9A-9K show example screenshots of a GUI for display on an AED. In some embodiments, the GUI may be displayed on a display (e.g., display 106, display 720, and/or the like). In some embodiments, when the non-clinical power adapter is connected to and recognized by the AED, other than the delivery of defibrillation electrotherapy, such features (e.g., GUI displays) may remain functional when the AED enters into the non-clinical mode (e.g., for training, educational and/or other non-clinical usage purposes).

Figure 9A:
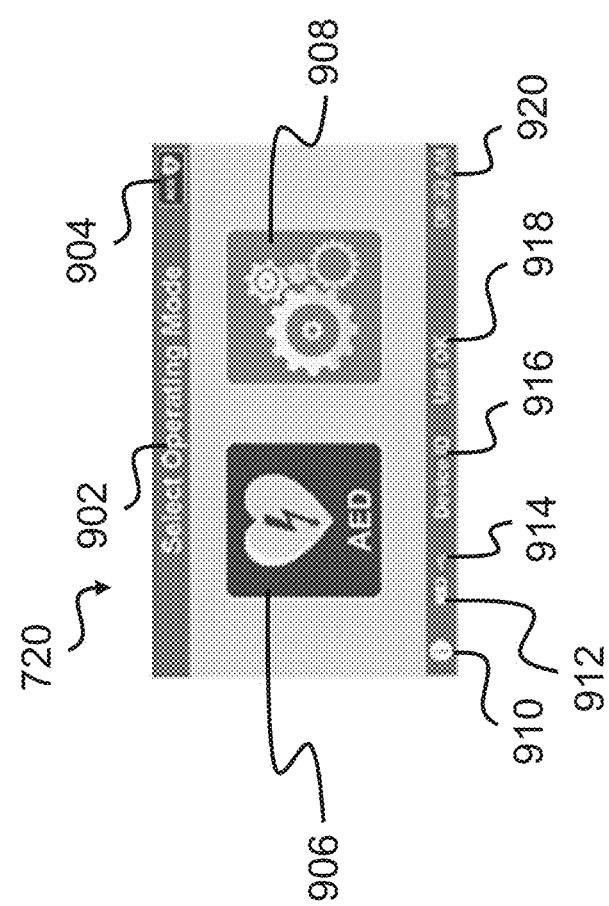
FIGS. 9A-9K show example diagrams and/or screenshots of an automated external defibrillator with a graphical user interface in use, according to some embodiments.

In some embodiments, as shown in FIG. 9A, a management screen (e.g., initial screen, home screen, operating mode selection screen, and/or the like) of the GUI displayed by display 720 (e.g., upon startup of AED 700, when battery pack 795 is electrically coupled to AED 700, and/or the like) may include a plurality of graphical elements (e.g., messages, icons, indicators, and/or the like). For example, such graphical elements may include message 902, first graphical button 904, second graphical button 906, third graphical button 908, information icon 910, battery icon 912, USB icon 914, device identifier 916, display message 918, time indicator 920 and/or the like. For the purpose of illustration, first graphical button 904 and/or second graphical button 906 (e.g., when selected by a user) may cause AED 700 to enter a clinical mode (e.g., when battery pack 795 is connected to the electrical connector of AED 700). Additionally or alternatively, third graphical button 908 (e.g., when selected by a user) may cause AED 700 to enter a configurability mode (e.g., for configuring settings of AED 700). In some embodiments, information icon 910 (e.g., when selected by a user) may cause display 720 to display information, such as expiration dates of electrodes 798*a* and 798*b*, expiration date of battery pack 795, expiration date of non-clinical power adapter 797, and/or the like. In some embodiments, battery indicator 912 may indicate remaining battery life (e.g., of battery pack 795). In some embodiments, device identifier 914 may include an identifier (e.g., unique identifier, model number, serial number, any combination thereof, and/or the like) of AED 700. In some embodiments, display message 918 may include an indication of the status of AED 700 and/or the like). In some embodiments, time indicator 920 may indicate a current time and/or the like.

Figure 9B:
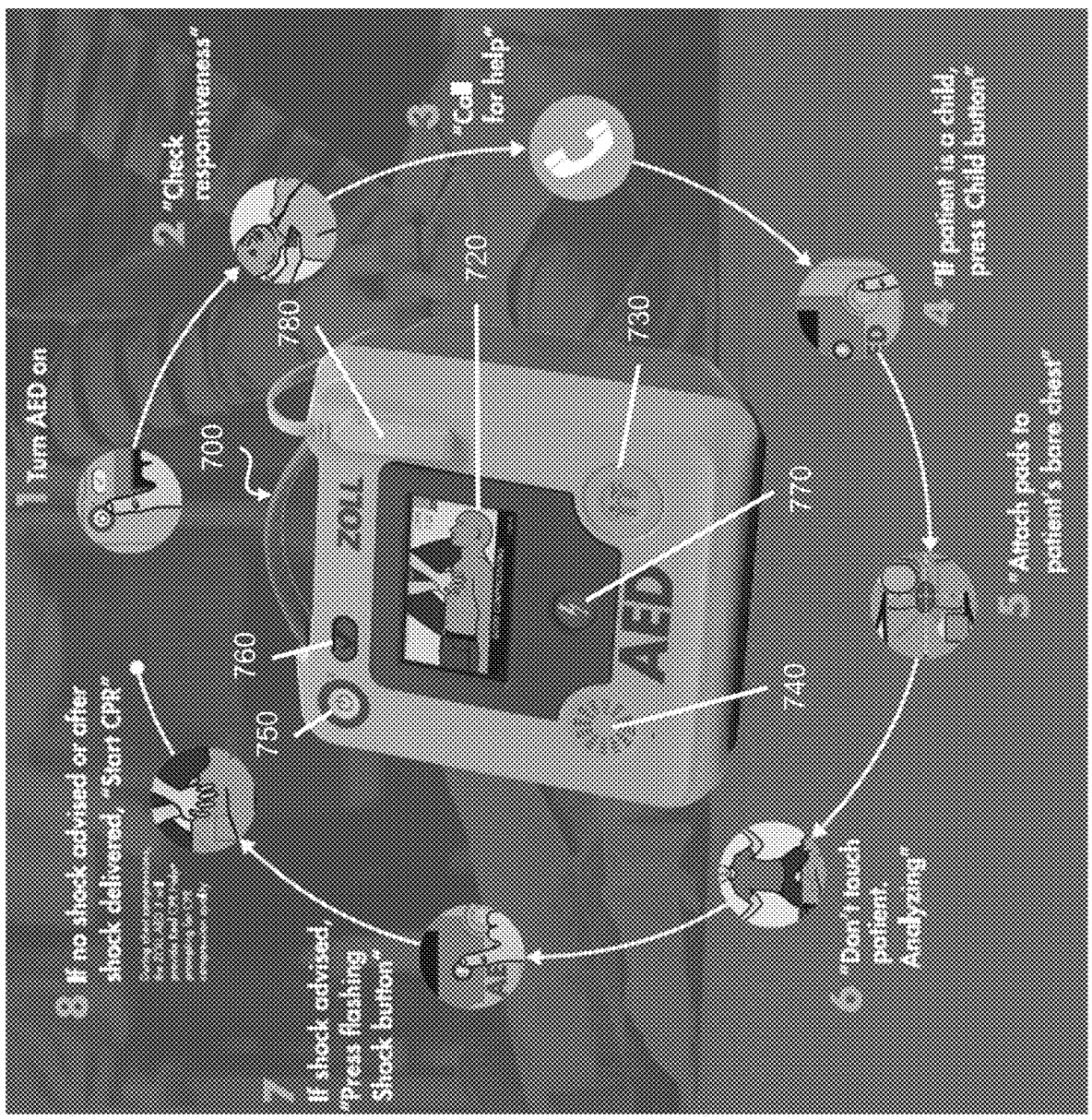
Figure 9D:
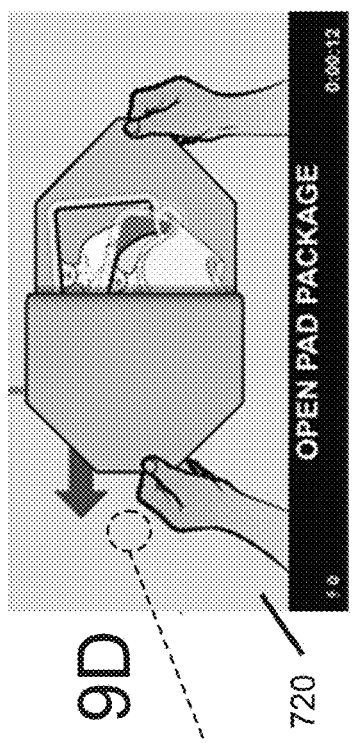
Figure 9E:
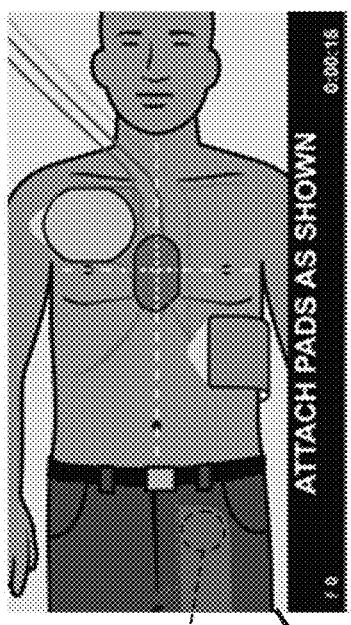
Figure 9F:
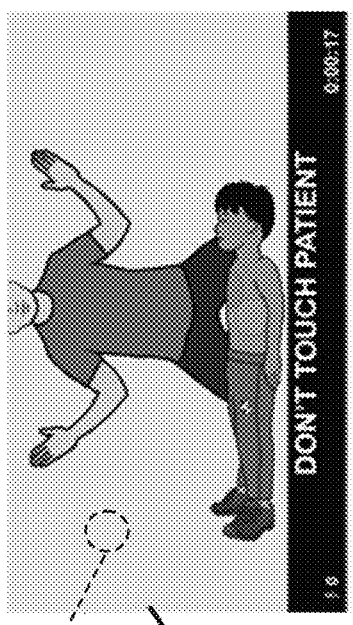

In some embodiments, as shown in FIG. 9B, a process for using AED 700 in a clinical mode may include steps 1-8. In some embodiments, at step 1, a user may turn on AED 700 (e.g., by selecting control 750 (e.g., a power button and/or the like)). Additionally or alternatively, at step 2, a user may check a patient for responsiveness (e.g., display 720 of AED 700 may display a message instructing the user to check responsiveness). Additionally or alternatively, at step 3, a user may call for help (e.g., display 720 of AED 700 may display a message instructing the user to call for help). Additionally or alternatively, at step 4, a user may determine whether to switch AED 700 from an adult mode to a pediatric mode (e.g., display 720 of AED 700 may display a message instructing the user to press control 730 (e.g., child button) if the patient is a child). Additionally or alternatively, at step 5, a user may attach pads (e.g., electrodes 798*a* and 798*b*, chest compression sensor 799, and/or the like) to the patient's bare chest (e.g., display 720 of AED 700 may display a message instructing the user to attach pads to the patient's bare chest). For example, as shown in FIG. 9D, display 720 of AED 700 may display a message (e.g., and/or a still image or animation corresponding to the message) instructing the user to open a package containing the pads, and/or, as shown in FIG. 9E, display 720 of AED 700 may display a message instructing the user to attach the pad (e.g., to the patient's bare chest) as shown in a still image or animation corresponding to the message. Additionally or alternatively, at step 6, AED 700 may analyze sensor data (e.g., ECG data and/or the like) to determine whether there is a shockable rhythm (e.g., display 720 of AED 700 may display a message instructing the user to not touch the patient while AED 700 analyzes the sensor data). For example, as shown in FIG. 9F, display 720 of AED 700 may display a message (e.g., and/or a still image or animation corresponding to the message) instructing the user not to touch the patient (e.g., while AED 700 performs the analysis). Additionally or alternatively, at step 7, AED 700 may automatically provide electrotherapy (e.g., a defibrillation shock and/or the like) to the patient if the patient has a shockable rhythm and/or the user may select control 770 to provide electrotherapy to the patient if the patient has a shockable rhythm (e.g., display 720 of AED 700 may display a message instructing the user to press control 770 (e.g., a shock button) if the patient has a shockable rhythm). Additionally or alternatively, at step 8 (e.g., if there was not a shockable rhythm or after a shock was delivered), the user may begin resuscitation (e.g., CPR and/or the like) on the patient (e.g., display 720 of AED 700 may display a message instructing the user to start CPR).

Figure 9C:
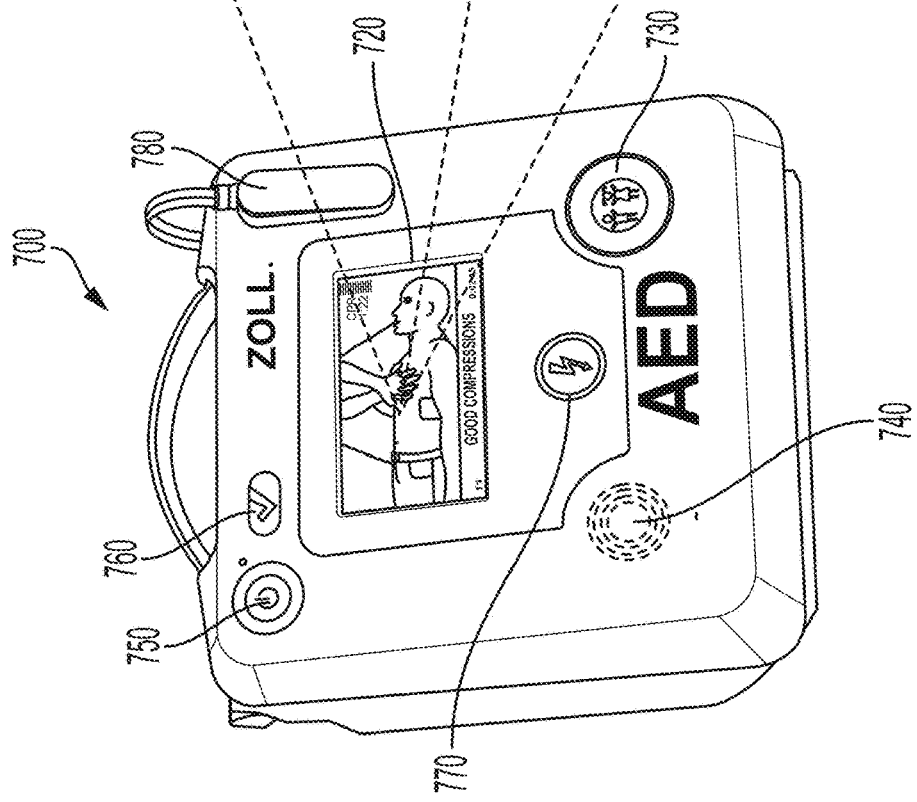
Figure 9G:
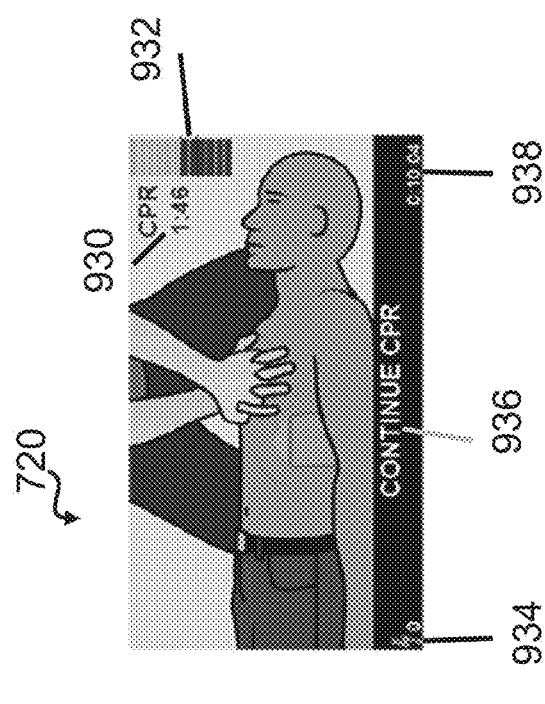
Figure 9H:
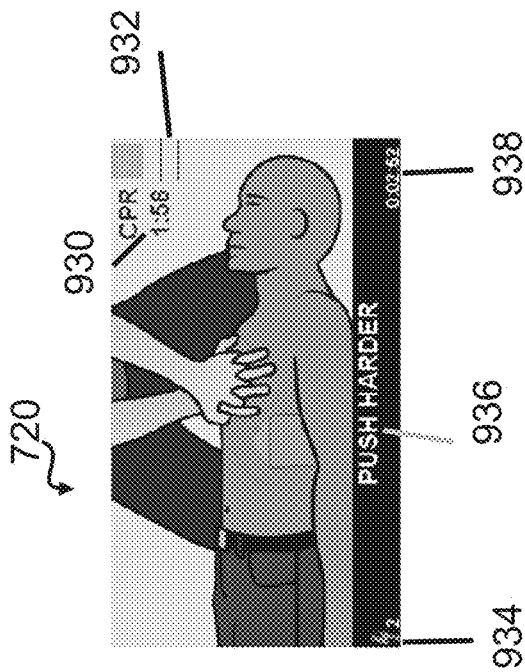
Figure 9I:
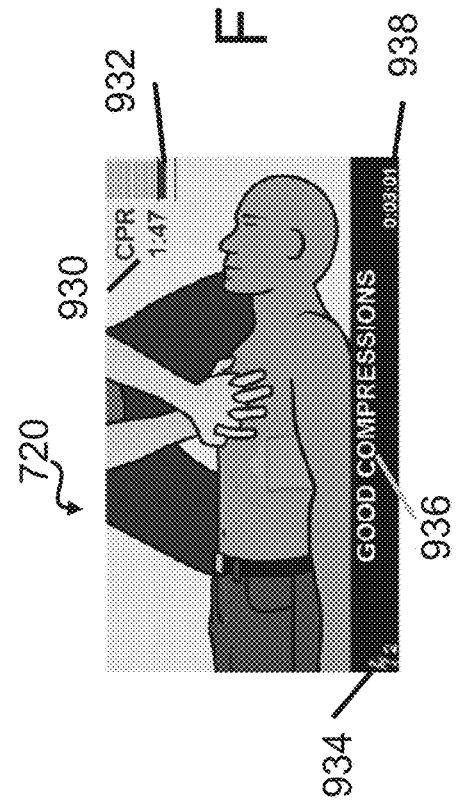

In some embodiments, while the user performs resuscitation (e.g., CPR), AED 700 may provide feedback. For example, as shown in FIGS. 9C and 9G-9I, display 720 of AED 700 may display a message (e.g., and/or a still image or animation corresponding to the message) providing such feedback. In some embodiments, as shown in FIG. 9G (e.g., in a non-professional mode, a lay rescuer mode, and/or the like), display 720 of AED 700 may display a message (e.g., and/or a still image or animation corresponding to the message) instructing the user to continue CPR (e.g., chest compressions and/or the like). In some embodiments, as shown in FIGS. 9C, 9H, and 9I (e.g., in a professional mode and/or the like), display 720 of AED 700 may display messages (e.g., and/or still images or animations corresponding to the messages) instructing the user about the quality of CPR being performed. For example, as shown in FIG. 9H, display 720 of AED 700 may display a message (e.g., and/or a still image or animation corresponding to the message) instructing the user to push harder (e.g., because depth of chest compressions is too small). For example, as shown in FIGS. 9C and 9I, display 720 of AED 700 may display a message (e.g., and/or a still image or animation corresponding to the message) instructing the user that chest compressions being performed by the user are acceptable (e.g., good, within an appropriate range for depth, and/or the like).

In some embodiments, the GUI displayed on display 720 may include a plurality of graphical elements (e.g., messages, icons, indicators, and/or the like). For example, the GUI may include countdown timer 930, depth indicator 932, shock indicator 934, prompt 936, elapsed time indicator 938, and/or the like. For example, prompt 936 may include a message instructing the user to adjust and/or maintain performance of resuscitations (e.g., chest compressions, CPR, and/or the like). Additionally or alternatively, depth indicator 932 may indicate a depth of the chest compressions (e.g., bars indicating the measured/determined depth of compressions, lines indicating a desired range of depth of the chest compressions, and/or the like). Additionally or alternatively, countdown timer 930 may indicate an amount of time to continue performance of resuscitation (e.g., CPR and/or the like). Additionally or alternatively, event time indicator 938 may indicate elapsed time of an event (e.g., a clinical event, a training event, and/or the like) during which the resuscitation (e.g., chest compressions and/or the CPR) is being performed. Additionally or alternatively, shock indicator 934 may indicate of a number of defibrillating shocks (or a number of discharges of the energy stored in capacitor(s) via an internal discharge circuit, e.g., during a non-clinical and/or training event).

Figure 9J:
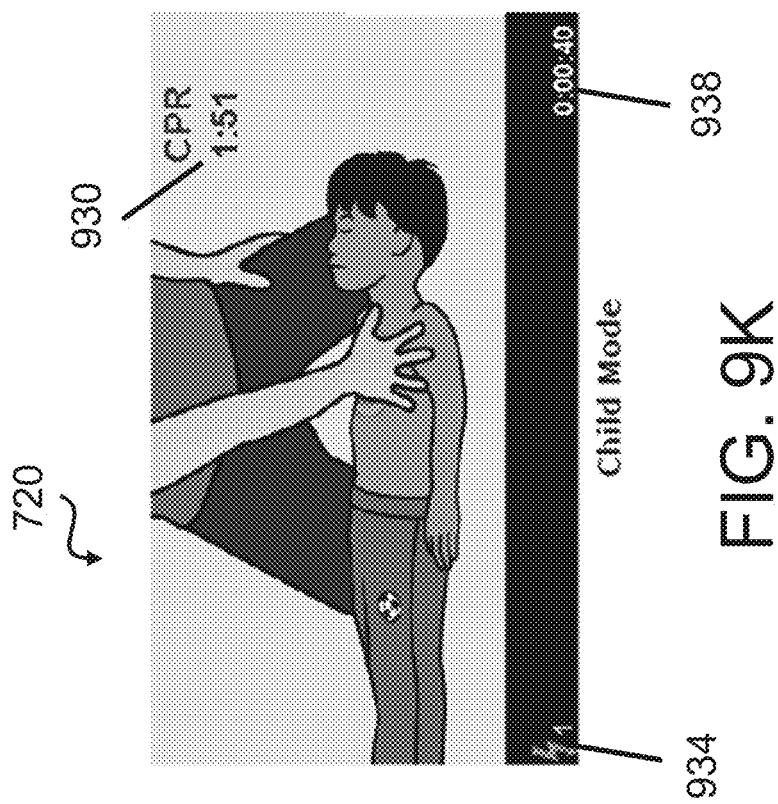
Figure 9K:
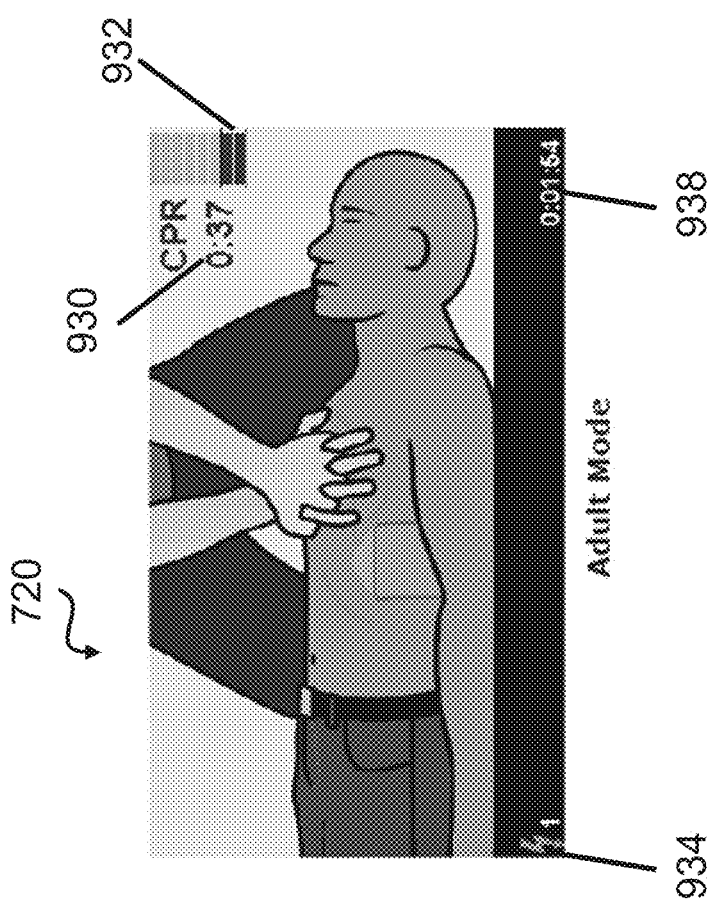

In some embodiments, the GUI displayed on display 720 may be different depending on whether AED 700 is in an adult mode or a pediatric mode. For example, as shown in FIG. 9J, the GUI displayed on display 720 may include an image (e.g., and/or animation) of an adult when in the adult mode. Additionally or alternatively, as shown in FIG. 9K, the GUI displayed on display 720 may include an image (e.g., and/or animation) of a child when in the pediatric mode.

Referring now to FIGS. 10A-10D, FIGS. 10A-10D show example screenshots of a GUI for display on an AED. In some embodiments, the GUI may be displayed on a display (e.g., display 106, display 720, and/or the like). In some embodiments, when the non-clinical power adapter is connected to and recognized by the AED, other than the delivery of defibrillation electrotherapy, such features (e.g., GUI displays) may remain functional when the AED enters into the non-clinical mode (e.g., for training, educational and/or other non-clinical usage purposes).

In some embodiments, while the user performs resuscitation (e.g., CPR), AED 700 may provide feedback. For example, as shown in FIGS. 10A-10D, the GUI displayed on display 720 may include a plurality of graphical elements (e.g., messages, icons, indicators, and/or the like).

In some embodiments, as shown in FIGS. 10A and 10B, the GUI may include depth indicator 1002, chest compression rate indicator 1004, countdown timer 1006, shock indicator 1008, prompt 1010, elapsed time indicator 1012, and/or the like. For example, prompt 1010 may include a message instructing the user to adjust and/or maintain performance of resuscitations (e.g., chest compressions, CPR, and/or the like). Additionally or alternatively, depth indicator 1002 may indicate a depth of the chest compressions (e.g., a number indicating the measured/determined depth of compressions; highlighting, coloring, and/or shading indicating the depth is outside a desired range of depth of the chest compressions; and/or the like). Additionally or alternatively, chest compression rate indicator 1004 may indicate a measured and/or determined rate of chest compressions. Additionally or alternatively, countdown timer 1006 may indicate an amount of time to continue performance of resuscitation (e.g., CPR and/or the like). Additionally or alternatively, shock indicator 1008 may indicate of a number of defibrillating shocks (or a number of discharges of the energy stored in capacitor(s) via an internal discharge circuit, e.g., during a non-clinical and/or training event). Additionally or alternatively, event time indicator 1012 may indicate elapsed time of an event (e.g., a clinical event, a training event, and/or the like) during which the resuscitation (e.g., chest compressions and/or the CPR) is being performed.

In some embodiments, as shown in FIGS. 10C and 10D, the GUI may include depth indicator 1002, chest compression rate indicator 1004, countdown timer 1006, shock indicator 1008, prompt 1010, elapsed time indicator 1012, ECG rhythm graph 1014, and/or the like. For example, prompt 1010 may include a message instructing the user to adjust and/or maintain performance of resuscitations (e.g., chest compressions, CPR, and/or the like). Additionally or alternatively, depth indicator 1002 may indicate a depth of the chest compressions (e.g., a number indicating the measured/determined depth of compressions; highlighting, coloring, and/or shading indicating the depth is outside a desired range of depth of the chest compressions; and/or the like). Additionally or alternatively, chest compression rate indicator 1004 may indicate a measured and/or determined rate of chest compressions (e.g., a number indicating the measured/determined rate of compressions; highlighting, coloring, and/or shading indicating the rate is outside a desired range of depth of the chest compressions; and/or the like). Additionally or alternatively, countdown timer 1006 may indicate an amount of time to continue performance of resuscitation (e.g., CPR and/or the like). Additionally or alternatively, shock indicator 1008 may indicate of a number of defibrillating shocks (or a number of discharges of the energy stored in capacitor(s) via an internal discharge circuit, e.g., during a non-clinical and/or training event). Additionally or alternatively, event time indicator 1012 may indicate elapsed time of an event (e.g., a clinical event, a training event, and/or the like) during which the resuscitation (e.g., chest compressions and/or the CPR) is being performed. Additionally or alternatively, ECG rhythm graph 1014 may include a graph (e.g., line graph and/or the like) indicating the measured/determined ECG rhythm of a patient.

In some embodiments, prompt 1010 may include a message instructing the user about the quality of resuscitation (e.g., chest compressions, CPR, and/or the like) being performed. For example, as shown in FIGS. 10A and 10C, display 720 of AED 700 may display a prompt 1010 including a message instructing the user to push harder (e.g., because depth of chest compressions is too small). For example, as shown in FIGS. 10B and 10D, display 720 of AED 700 may display a prompt 1010 including a message instructing the user that chest compressions being performed by the user are acceptable (e.g., good, within an appropriate range for depth, and/or the like).

Figure 11:
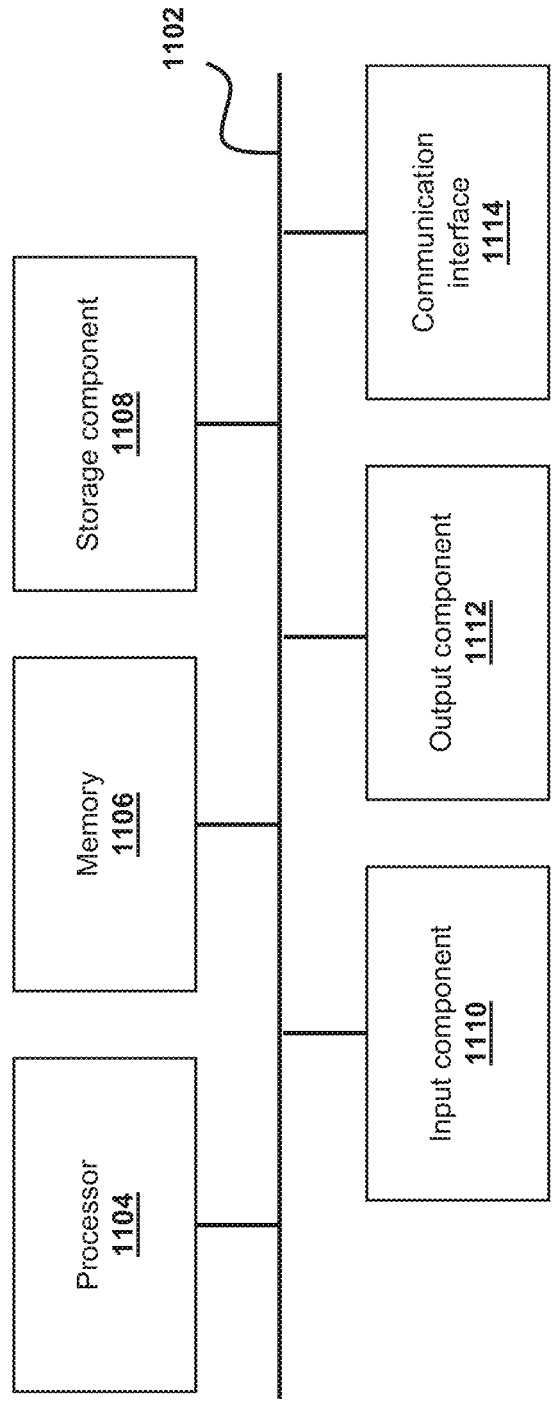
FIG. 11 shows an example block diagram of a computing device, according to some embodiments.

Referring now to FIG. 11, FIG. 11 is a diagram of example components of a device 1100. Device 1100 may correspond to one or more devices of AED 102 and/or external device 150. In some embodiments, AED 102 and/or external device 150 may include at least one device 1100 and/or at least one component of device 1100. As shown in FIG. 11, device 1100 may include bus 1102, processor 1104, memory 1106, storage component 1108, input component 1110, output component 1112, and communication interface 1114.

Bus 1102 may include a component that permits communication among the components of device 1100. In some embodiments, processor 1104 may be implemented in hardware, software, firmware, and/or any combination thereof. For example, processor 1104 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like), and/or the like, which can be programmed to perform a function. Memory 1106 may include random access memory (RAM), read-only memory (ROM), and/or another type of dynamic or static storage device (e.g., flash memory, magnetic memory, optical memory, and/or the like) that stores information and/or instructions for use by processor 1104.

Storage component 1108 may store information and/or software related to the operation and use of device 1100. For example, storage component 1108 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 1110 may include a component that permits device 1100 to receive information, such as via user input (e.g., a touch screen display, a keyboard, a keypad, a mouse, a button, a switch, a microphone, a camera, and/or the like). Additionally or alternatively, input component 1110 may include a sensor for sensing information (e.g., a global positioning system (GPS) component, an accelerometer, a gyroscope, an actuator, and/or the like). Output component 1112 may include a component that provides output information from device 1100 (e.g., a display, a speaker, one or more light-emitting diodes (LEDs), and/or the like).

Communication interface 1114 may include a transceiver-like component (e.g., a transceiver, a receiver and transmitter that are separate, and/or the like) that enables device 1100 to communicate with other devices, such as via a wired connection, a wireless connection, or a combination of wired and wireless connections. Communication interface 1114 may permit device 1100 to receive information from another device and/or provide information to another device. For example, communication interface 1114 may include an Ethernet interface, an optical interface, a coaxial interface, an infrared interface, a radio frequency (RF) interface, a USB interface, a Wi-Fi® interface, a Bluetooth® interface, a Zigbee® interface, a cellular network interface, and/or the like.

Device 1100 may perform one or more processes described herein. Device 1100 may perform these processes based on processor 1104 executing software instructions stored by a computer-readable medium, such as memory 1106 and/or storage component 1108. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 1106 and/or storage component 1108 from another computer-readable medium or from another device via communication interface 1114. When executed, software instructions stored in memory 1106 and/or storage component 1108 may cause processor 1104 to perform one or more processes described herein. Additionally or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 11 are provided as an example. In some embodiments, device 1100 may include additional components, fewer components, different components, or differently arranged components than those shown in FIG. 11. Additionally or alternatively, a set of components (e.g., one or more components) of device 1100 may perform one or more functions described as being performed by another set of components of device 1100.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising", "including", "carrying", "having", "containing", "involving", "holding", "composed of", and the like are to be understood to be open-ended, i.e., to mean including but not limited to. Only the transitional phrases "consisting of" and "consisting essentially of" shall be closed or semi-closed transitional phrases, respectively.

As used herein, the terms "right", "left", "top", and derivatives thereof shall relate to the present disclosure as it is oriented in the drawing figures. However, it is to be understood that embodiments of the present disclosure can assume various alternative orientations and, accordingly, such terms are not to be considered as limiting. Also, it is to be understood that embodiments of the present disclosure can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other types of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is currently claimed:

1. An automated external defibrillator, comprising:
    an electrical connector configured to receive a battery pack;
    at least one capacitor configured to store energy and an electrotherapy delivery circuit configured to deliver the energy externally as electrotherapy to a patient;
    at least one discharge circuit configured to internally discharge energy stored in the at least one capacitor, wherein the energy is not provided to the patient when internally discharged;
    a non-clinical power adapter configured to be received by the electrical connector; and
    at least one processor configured to:
        determine whether the non-clinical power adapter is electrically coupled to the electrical connector,
        determine whether the automated external defibrillator recognizes the non-clinical power adapter, and
        enable power to be supplied to the automated external defibrillator from the non-clinical power adapter if the automated external defibrillator recognizes the non-clinical power adapter,
    wherein enabling power to be supplied to the automated external defibrillator from the non-clinical power adapter comprises enabling the automated external defibrillator to operate in a non-clinical mode, and
    wherein enabling the automated external defibrillator to operate in a non-clinical mode comprises:
        disabling delivery of energy externally as electrotherapy;
        charging the at least one capacitor to a predetermined threshold that is less than a minimum energy setting for clinical use; and
        discharging the stored energy from the at least one capacitor internally through the at least one discharge circuit.

2. The automated external defibrillator of claim 1, wherein discharging the stored energy from the at least one capacitor internally through the at least one discharge circuit comprises discharging the stored energy from the at least one capacitor internally through the at least one discharge circuit in response to a control on an exterior of the automated external defibrillator.

3. The automatic external defibrillator of claim 1, wherein the predetermined threshold comprises at least one of less than 50 J, less than 20 J, less than 10 J, less than 5 J, less than 2 J, 0.1 J to 5 J, or 0.1 J to 2 J.

4. The automated external defibrillator of claim 1, further comprising a plurality of electrical components other than the at least one capacitor, wherein enabling the automated external defibrillator to operate in a non-clinical mode comprises enabling power to be supplied to the plurality of electrical components from the non-clinical power adapter.

5. The automated external defibrillator of claim 4, wherein enabling power to be supplied to the plurality of electrical components comprises operating the plurality of electrical components as the plurality of electrical components operate in a clinical mode.

6. The automated external defibrillator of claim 1, wherein the at least one processor is further configured to:
    disable the power being supplied to the automated external defibrillator from the non-clinical power adapter if the automated external defibrillator does not recognize the non-clinical power adapter.

7. The automated external defibrillator of claim 1, wherein determining whether the automated external defibrillator recognizes the non-clinical power adapter comprises determining whether the automated external defibrillator is compatible with the non-clinical power adapter.

8. The automated external defibrillator of claim 7, wherein determining whether the automated external defibrillator is compatible with the non-clinical power adapter comprises determining whether software of the automated external defibrillator recognizes the non-clinical power adapter.

9. The automated external defibrillator of claim 8, wherein determining whether software of the automated external defibrillator recognizes the non-clinical power adapter comprises determining whether a version of the software installed on the automated external defibrillator recognizes the non-clinical power adapter.

10. The automated external defibrillator of claim 7, wherein determining whether the automated external defibrillator is compatible with the non-clinical power adapter comprises at least one of:
    determining whether software of the automated external defibrillator is compatible with the non-clinical power adapter;
    determining whether hardware of the automated external defibrillator is compatible with the non-clinical power adapter; or
    any combination thereof.

11. The automated external defibrillator of claim 10, wherein determining whether the software of the automated external defibrillator is compatible with the non-clinical power adapter comprises determining whether a version of the software installed on the automated external defibrillator is compatible with the non-clinical power adapter.

12. The automated external defibrillator of claim 10, wherein determining whether the hardware of the automated external defibrillator is compatible with the non-clinical power adapter comprises determining whether pins of the electrical connector are compatible with the non-clinical power adapter.

13. The automated external defibrillator of claim 1, wherein the non-clinical power adapter comprises a memory storing at least one identifier of the non-clinical power adapter, and wherein determining whether the non-clinical power adapter is electrically coupled to the electrical connector comprises reading the at least one identifier from the memory.

14. The automated external defibrillator of claim 1, wherein the non-clinical power adapter is configured to supply power having a first voltage and a first current, and wherein at least one of the first voltage or the first current is different than a second voltage or a second current, respectively, of power supplied by the battery pack.

15. The automated external defibrillator of claim 14, wherein determining whether the non-clinical power adapter is electrically coupled to the electrical connector comprises detecting that the at least one of the first voltage or the first current is different than the second voltage or the second current, respectively.

16. An automated external defibrillator, comprising:
an electrical connector configured to receive a battery pack;
at least one capacitor configured to store energy and an electrotherapy delivery circuit configured to deliver the energy externally as electrotherapy to a patient;
at least one discharge circuit configured to internally discharge energy stored in the at least one capacitor, wherein the energy is not provided to the patient when internally discharged;
a non-clinical power adapter configured to be received by the electrical connector;
a communication line connecting the electrical connector and a switching element of the non-clinical power adapter and an input/output (I/O) line connecting the switching element and a voltage regulator of the non-clinical power adapter; and
at least one processor configured to:
determine whether the non-clinical power adapter is electrically coupled to the electrical connector,
determine whether the automated external defibrillator recognizes the non-clinical power adapter,
enable power to be supplied to the automated external defibrillator from the non-clinical power adapter if the automated external defibrillator recognizes the non-clinical power adapter, and
disable the power being supplied to the automated external defibrillator from the non-clinical power adapter if the automated external defibrillator does not recognize the non-clinical power adapter,
wherein disabling the power being supplied to the automated external defibrillator from the non-clinical power adapter comprises communicating with the switching element via the communication line to set the I/O line to a first logical voltage, and wherein enabling power to be supplied to the automated external defibrillator from the non-clinical power adapter comprises communicating with the switching element via the communication line to maintain the I/O line at a second logical voltage.

17. The automated external defibrillator of claim 16, wherein the voltage regulator is configured to supply power from the non-clinical power adapter to the automated external defibrillator when the I/O line is set to the second logical voltage and to stop supplying power from the non-clinical power adapter to the automated external defibrillator when the I/O line is set to the first logical voltage.

18. The automated external defibrillator of claim 17, wherein the switching element comprises a battery monitor circuit, wherein the battery monitor circuit is configured to disable the voltage regulator by setting the I/O line to the first logical voltage.

19. The automated external defibrillator of claim 16, wherein enabling power to be supplied to the automated external defibrillator from the non-clinical power adapter comprises enabling the automated external defibrillator to operate in a non-clinical mode.

20. The automated external defibrillator of claim 19, wherein enabling the automated external defibrillator to operate in a non-clinical mode comprises:
disabling delivery of energy externally as electrotherapy;
charging the at least one capacitor to a predetermined threshold that is less than a minimum energy setting for clinical use; and
discharging the stored energy from the at least one capacitor internally through the at least one discharge circuit.

21. The automated external defibrillator of claim 20, wherein discharging the stored energy from the at least one capacitor internally through the at least one discharge circuit comprises discharging the stored energy from the at least one capacitor internally through the at least one discharge circuit in response to a control on an exterior of the automated external defibrillator.

22. The automatic external defibrillator of claim 20, wherein the predetermined threshold comprises at least one of less than 50 J, less than 20 J, less than 10 J, less than 5 J, less than 2 J, 0.1 J to 5 J, or 0.1 J to 2 J.

23. The automated external defibrillator of claim 20, further comprising a plurality of electrical components other than the at least one capacitor, wherein enabling the automated external defibrillator to operate in a non-clinical mode comprises enabling power to be supplied to the plurality of electrical components from the non-clinical power adapter.

24. The automated external defibrillator of claim 23, wherein enabling power to be supplied to the plurality of electrical components comprises operating the plurality of electrical components as the plurality of electrical components operate in a clinical mode.

25. The automated external defibrillator of claim 16, wherein determining whether the automated external defibrillator recognizes the non-clinical power adapter comprises determining whether the automated external defibrillator is compatible with the non-clinical power adapter.

26. The automated external defibrillator of claim 25, wherein determining whether the automated external defibrillator is compatible with the non-clinical power adapter comprises determining whether software of the automated external defibrillator recognizes the non-clinical power adapter.

27. The automated external defibrillator of claim 26, wherein determining whether software of the automated external defibrillator recognizes the non-clinical power adapter comprises determining whether a version of the software installed on the automated external defibrillator recognizes the non-clinical power adapter.

28. The automated external defibrillator of claim 25, wherein determining whether the automated external defibrillator is compatible with the non-clinical power adapter comprises at least one of:
determining whether software of the automated external defibrillator is compatible with the non-clinical power adapter;
determining whether hardware of the automated external defibrillator is compatible with the non-clinical power adapter; or
any combination thereof.

29. The automated external defibrillator of claim 28, wherein determining whether the software of the automated external defibrillator is compatible with the non-clinical power adapter comprises determining whether a version of the software installed on the automated external defibrillator is compatible with the non-clinical power adapter.

30. The automated external defibrillator of claim 28, wherein determining whether the hardware of the automated external defibrillator is compatible with the non-clinical power adapter comprises determining whether pins of the electrical connector are compatible with the non-clinical power adapter.

31. The automated external defibrillator of claim 16, wherein the non-clinical power adapter comprises a memory storing at least one identifier of the non-clinical power adapter, and wherein determining whether the non-clinical power adapter is electrically coupled to the electrical connector comprises reading the at least one identifier from the memory.

32. The automated external defibrillator of claim 16, wherein the non-clinical power adapter is configured to supply power having a first voltage and a first current, and wherein at least one of the first voltage or the first current is different than a second voltage or a second current, respectively, of power supplied by the battery pack.

33. The automated external defibrillator of claim 32, wherein determining whether the non-clinical power adapter is electrically coupled to the electrical connector comprises detecting that the at least one of the first voltage or the first current is different than the second voltage or the second current, respectively.

34. An automated external defibrillator, comprising:
an electrical connector configured to receive a battery pack;
at least one capacitor configured to store energy and an electrical delivery circuit configured to deliver the energy externally as electrotherapy to a patient;
at least one discharge circuit configured to internally discharge energy stored in the at least one capacitor, wherein the energy is not provided to the patient when internally discharged;
a non-clinical power adapter configured to be received by the electrical connector; and
at least one processor configured to determine whether the non-clinical power adapter is electrically coupled to the electrical connector, and in response to the determination:
disable delivery of energy externally as electrotherapy,
charge the at least one capacitor to a predetermined threshold that is less than a minimum energy setting for clinical use; and
discharge the stored energy from the at least one capacitor internally through the at least one discharge circuit.

35. The automatic external defibrillator of claim 34, wherein the predetermined threshold comprises at least one of less than 50 J, less than 20 J, less than 10 J, less than 5 J, less than 2 J, 0.1 J to 5 J, or 0.1 J to 2 J.

36. The automated external defibrillator of claim 34, further comprising a plurality of electrical components other than the at least one capacitor, wherein the at least one processor is further configured to enable power to be supplied to the plurality of electrical components from the non-clinical power adapter.

37. The automated external defibrillator of claim 34, wherein discharging the stored energy from the at least one capacitor internally through the at least one discharge circuit comprises discharging the stored energy from the at least one capacitor internally through the at least one discharge circuit in response to a first control on an exterior of the automated external defibrillator.

38. The automated external defibrillator of claim 37, wherein the first control comprises a shock button, wherein the shock button comprises a light, and wherein the energy stored in the at least one capacitor enables the light to turn on before the button is pressed and the energy stored by the at least one capacitor is discharged through the discharge circuit in response to the shock button being pressed.

39. The automated external defibrillator of claim 38, further comprising a second control, wherein the at least one processor is further configured to switch from an adult mode to a pediatric mode in response to the second control.

40. The automated external defibrillator of claim 34, further comprising a display on an exterior of the automated external defibrillator, wherein the at least one processor is further configured to, in response to determining the non-clinical power adapter is electrically coupled to the electrical connector, display a message indicating that the automated external defibrillator is not enabled for clinical use on the display.

41. The automated external defibrillator of claim 40, further comprising a speaker, wherein the at least one processor is further configured to, in response to determining the non-clinical power adapter is electrically coupled to the electrical connector, play an announcement indicating that the automated external defibrillator is not enabled for clinical use from the speaker.

* * * * *

UNITED STATES PATENT AND TRADEMARK OFFICE
CERTIFICATE OF CORRECTION

PATENT NO. : 12,233,275 B2
APPLICATION NO. : 17/672066
DATED : February 25, 2025
INVENTOR(S) : Kenneth R. Alleca Page 1 of 1

It is certified that error appears in the above-identified patent and that said Letters Patent is hereby corrected as shown below:

In the Claims

Column 66, Line 18, Claim 3, delete "automatic" and insert -- automated --

Column 68, Line 38, Claim 22, delete "automatic" and insert -- automated --

Column 70, Line 12, Claim 35, delete "automatic" and insert -- automated --

Signed and Sealed this
Thirteenth Day of May, 2025

Coke Morgan Stewart
*Acting Director of the United States Patent and Trademark Office*